(12) United States Patent
Fadeev et al.

(10) Patent No.: US 8,354,274 B2
(45) Date of Patent: Jan. 15, 2013

(54) SYNTHETIC SURFACES FOR CULTURING CELLS IN CHEMICALLY DEFINED MEDIA

(75) Inventors: Andrei Gennadyevich Fadeev, Elmira, NY (US); Jennifer Gehman, Painted Post, NY (US); Zara Melkoumian, Painted Post, NY (US); David Michael Weber, Corning, NY (US); Yue Zhou, Horseheads, NY (US)

(73) Assignee: Geron Corporation, Menlo Park, CA (US)

( * ) Notice: Subject to any disclaimer, the term of this patent is extended or adjusted under 35 U.S.C. 154(b) by 712 days.

(21) Appl. No.: 12/362,924

(22) Filed: Jan. 30, 2009

(65) Prior Publication Data

US 2009/0191627 A1     Jul. 30, 2009

Related U.S. Application Data

(60) Provisional application No. 61/062,890, filed on Jan. 30, 2008, provisional application No. 61/062,937, filed on Jan. 30, 2008.

(51) Int. Cl.
*C12N 5/071* (2010.01)
*C12N 11/00* (2006.01)
*C12N 11/08* (2006.01)

(52) U.S. Cl. .......................... 435/366; 435/174; 435/180

(58) Field of Classification Search .................. 435/366, 435/174, 180

See application file for complete search history.

(56) References Cited

U.S. PATENT DOCUMENTS

| | | | |
|---|---|---|---|
| 4,022,754 A * | 5/1977 | Howes et al. | 526/264 |
| 4,578,079 A | 3/1986 | Ruoslahti et al. | 523/11 |
| 4,792,525 A | 12/1988 | Ruoslahti et al. | 435/240.243 |
| 4,908,236 A | 3/1990 | Pitt et al. | 427/245 |
| 5,278,063 A | 1/1994 | Hubbell et al. | 435/240.243 |
| 5,330,911 A | 7/1994 | Hubbell et al. | 435/240.243 |
| 5,480,953 A | 1/1996 | Sugaya et al. | 526/320 |
| 5,643,561 A | 7/1997 | Katsuen et al. | 424/78.17 |
| 5,691,203 A | 11/1997 | Katsuen et al. | 435/402 |
| 5,695,997 A | 12/1997 | Ruoslahti et al. | 435/375 |
| 5,916,875 A | 6/1999 | Ruoslahti et al. | 514/12 |
| 6,121,027 A | 9/2000 | Clapper et al. | 435/180 |
| 6,306,922 B1 | 10/2001 | Hubbell et al. | 522/71 |
| 6,316,522 B1 | 11/2001 | Loomis et al. | 523/105 |
| 6,514,734 B1 | 2/2003 | Clapper et al. | 435/180 |
| 7,067,194 B2 | 6/2006 | Mao et al. | 428/429 |
| 7,384,984 B2 | 6/2008 | Lewandowski et al. | 514/772.1 |
| 7,402,339 B2 | 7/2008 | Schmidt et al. | 428/407 |
| 2003/0029418 A1 | 2/2003 | Deschamps et al. | 123/376 |
| 2003/0083389 A1 | 5/2003 | Kao et al. | 516/98 |
| 2003/0215946 A1 | 11/2003 | Nair et al. | 435/395 |
| 2005/0019747 A1 | 1/2005 | Anderson et al. | 435/4 |
| 2005/0036980 A1 | 2/2005 | Chaney et al. | 424/78.27 |
| 2005/0059150 A1 | 3/2005 | Guarino et al. | 435/370 |
| 2005/0136536 A1 | 6/2005 | Anderson et al. | 435/366 |
| 2005/0265980 A1 | 12/2005 | Chen et al. | 424/93.7 |
| 2005/0276858 A1 | 12/2005 | Kao et al. | 424/487 |
| 2005/0281857 A1 | 12/2005 | Heyer et al. | 424/423 |
| 2006/0100369 A1 | 5/2006 | Kao et al. | 525/54.1 |
| 2006/0127878 A1 | 6/2006 | Salomon et al. | 435/4 |
| 2006/0134050 A1 | 6/2006 | Griffith et al. | 424/70.16 |
| 2006/0263878 A1 | 11/2006 | Mochitate | 435/366 |
| 2007/0026518 A1 | 2/2007 | Healy et al. | 435/325 |
| 2007/0029924 A1 | 2/2007 | Ushifusa et al. | 313/496 |
| 2007/0167354 A1 | 7/2007 | Kennedy et al. | 514/8 |
| 2007/0269886 A1 | 11/2007 | Qian et al. | 435/366 |
| 2009/0043079 A1 | 2/2009 | Chen et al. | 530/402 |
| 2009/0081797 A1 * | 3/2009 | Fadeev et al. | 436/86 |
| 2010/0099160 A1 * | 4/2010 | Jiang et al. | 435/180 |

FOREIGN PATENT DOCUMENTS

| | | |
|---|---|---|
| EP | 0614923 B1 | 1/2000 |
| JP | 01-309682 | 12/1989 |
| JP | 2002-191353 | 7/2002 |
| JP | 2006-042794 | 2/2006 |
| JP | 2006-174826 | 7/2006 |
| WO | 98/31734 | 7/1998 |
| WO | 02/06373 A1 | 1/2002 |
| WO | 02/062961 A2 | 8/2002 |
| WO | 02/062969 A2 | 8/2002 |
| WO | 03/029418 A2 | 4/2003 |
| WO | 2004/037164 A2 | 5/2004 |
| WO | 2006/105278 A2 | 10/2006 |
| WO | 2007/012144 | 2/2007 |
| WO | 2007/104107 A1 | 9/2007 |
| WO | 2008/118392 A2 | 10/2008 |

OTHER PUBLICATIONS

Anderson, Daniel G., Levenberg, Shulamit, Langer, Robert, Nanoliter-scale synthesis of arrayed biomaterials and application to human embryonic stem cells, Nature Biotechnology,, vol. 22, No. 7, Jul. 2004, 863-866.

Barber, T.A., Harbers, G.M., Park, S., Gilbert, M., Healy, K.E., "Ligand Density Characterization of Peptide-Modified Biomaterials," Biomaterials, 26(34), 6897-6905 (2005).

Barber, T.A., Golledge, S.L., Castner, D.G, and Healy, K.E., "Peptide-modified p(AAm-co-EG/AAc) IPNS Grafted to Bulk Titanium Modulate Osteoblast Behavior In Vitro," J. Biomed. Mater. Res., 64A, 38-47 (2003).

(Continued)

*Primary Examiner* — Karen Cochrane Carlson
*Assistant Examiner* — Natalie Moss
(74) *Attorney, Agent, or Firm* — Susan S. Wilks

(57) ABSTRACT

Synthetic surfaces capable of supporting culture of eukaryotic cells including stem cells and undifferentiated human embryonic stem cells in a chemically defined medium include a swellable (meth)acrylate layer and a polypeptide conjugated to the swellable (meth)acrylate layer. The swellable (meth)acrylate layer may be formed by polymerizing monomers in a composition that includes a carboxyl group-containing (meth)acrylate monomer, a cross-linking (di- or higher-functional) (meth)acrylate monomer, and a hydrophilic monomer capable of polymerizing with the carboxyl group-containing (meth)acrylate monomer and the cross-linking (meth)acrylate monomer. The swellable (meth)acrylate layer has an equilibrium water content in water of between about 5% and about 70%. The conjugated peptide may include an RGD amino acid sequence.

10 Claims, 21 Drawing Sheets

OTHER PUBLICATIONS

Bearinger, J.P., Castner, D.G., and Healy, K.E., "Biomolecular Modification of P(AAm-co-EG/AA) IPNs Supports Osteoblast Adhesion and Phenotypic Expression," J. Biomaterials Science:Polymer Ed., 9(7), 629-652 (1998).

Bearinger, J.P., Castner, D.G., Chen, J., Hubchak, S., Golledge, S.L., and Healy, K.E., "P(AAm-co-EG) Interpenetrating Polymer Networks Grafted to Oxide Surfaces: Surface Characterization, Protein Adsorption, and Cell Detachment Studies," Langmuir, 13(19), 5175-5183 (1997).

Braam, Stefan R., et al., Recombinant Vitronectin Is a Functionally Defined Substrate that Supports Human Embryonic Stem Cell Self Renewal Via AVB5 Integrin, Stem Cells express, Jul. 3, 2008, 1-20.

Brandley, B.K., et al., "Covalent Attachment of an Arg-Gyl-Asp Sequence Peptide to Derivatizable Polyacrylamide Surfaces: Sequence Peptide to Derivatizable Polyacrylamide Surfaces: Support of Fibroblast Adhesion and Long-Term Growth", Analytical Biochemistry, vol. 172, 1988, 270-278.

Drumheller PD, Herbert CB, Hubbell JA; "Bioactive Peptides and Surface Design", Interfacial Phenomena and Bioproducts, J.L. Brash et al., Marcel Dekker, Inc, 1996, pp. 273-310.

Cruise GM, Scharp DS, and Hubbell JA. Characterization of permeability and network structure of interfacially photopolymerized poly-(ethylene glycol) diacrylate hydrogels. Biomaterials 19: 1287-1294, 1998.

Dawson, Eileen, et al., "Biomaterials for stem cell differentiation", Advanced Drug Delivery Reviews, vol. 60, 2008, 215-228.

Drumheller, Paul D., Elbert, Donald L., Hubbell, Jeffrey A., Multifunctional Poly(ethylene glycol) Semi-Interpenetrating Polymer Networks as Highly Selective Adhesive Substrates for Bioadhesive Peptide Grafting, Biotechnology and Bioengineering, vol. 43, pp. 772-780, (1994).

Drumheller PD and Hubbell JA. Polymer networks with grafted cell adhesion peptides for highly biospecific cell adhesive substrates. Anal Biochem 222: 380-388, 1994.

Drumheller P.D. and Hubbell J.A.: Surface immobilization of adhesion ligands for investigations of cell/substrate interactions. In: The Biomedical Engineering Handbook, J.D. Bronzino Ed., CRC and IEEE Press 1583-1596, 1995.

Fittkau MH, Zilla P, Bezuidenhout D, Lutolf MP, Human P, Hubbell JA, and Davies N. The selective modulation of endothelial cell mobility on RGD peptide containing surfaces by YIGSR peptides. Biomaterials 26: 167-174, 2005.

Harbers G.M., Gamble L.J., Irwin E.F., Castner D.G., Healy K.E., "Development and Characterization of a High-Throughput System for Assessing Cell-Surface Receptor-Ligand Engagement," Langmuir, 21(18), 8374-84 (2005).

Harbers G.M., Healy, K.E., "The Effect of Ligand Type and Density on Osteoblast Adhesion, Proliferation, and Matrix Mineralization," J. Biomed. Mater. Res. Part A, 75A, 855-869 (2005).

Healy, K.E., Rezania, A., and Stile, A., "Designing Biomaterials to Direct Biological Responses," Annals of the New York Academy of Sciences, 875, 24-35 (1999).

Healy, K.E., "Molecular Engineering of Materials for Bioreactivity," Current Opinion in Solid State and Materials Science, 4, 381-387 (1999).

Heggli M, Tirelli N, Zisch A, and Hubbell JA. Michael-type addition as a tool for surface functionalization. Bioconjug Chem 14: 967-973, 2003.

Hern DL and Hubbell JA. Incorporation of adhesion peptides into nonadhesive hydrogels useful for tissue resurfacing. J Biomed Mater Res 39: 266-276, 1998.

Hubbell JA. Biomaterials in tissue engineering. Biotechnology (NY) 13: 565-576, 1995.

Hubbell JA, Massia SP, and Drumheller PD. Surface-grafted cell-binding peptides in tissue engineering of the vascular graft. Ann NY Acad Sci 665: 253-258, 1992.

Huebsch, N., Gilbert, M., Healy, K.E., "Analysis of Sterilization Protocols for Peptide-Modified Hydrogels," J. Biomed. Mater. Res. Part B, 74B(1), 440-447 (2005).

Irwin, E.F., Ho, J.E., Kane, S.R., Healy, K.E., "Analysis of Interpenetrating Polymer Networks via Quartz Crystal Microbalance with Dissipation Monitoring," Langmuir, 21(12), 5529-5536 (2005).

Kim, S.-Y., Chung, E., Gilbert, M., and Healy, K.E., "Synthetic MMP-13 Degradable ECMs Based on Poly(N-isopropyl acrylamide-co-Acrylic acid) Semi-Interpenetrating Polymer Networks I. Degradation and Cell Migration," J. Biomed. Mater. Res. Part A, 75(1), 73-88 (2005).

Kim, S.-Y., and Healy, K.E., "Synthesis and Characterization of Injectable Poly(N-isopropylacrylamide-co-Acrylic acid) Hydrogels with Proteolytically Degradable Cross-links," Biomacromolecules, 4, 1214-1223 (2003).

Li Y, Powell S, Brunette E, Lebkowski J, Mandalam R. Expansion of human embryonic stem cells in defined serum-free medium devoid of animal-derived products. Biotechnol Bioeng. 91(6):688-98, 2005.

Li, Y.J., Chung, E.H., Rodriguez, R.T., Firpo, M.T., Healy, K.E., "Hydrogels as Artificial Matrices for Human Embryonic Stem Cell Self-Renewal," J. Biomed. Mater. Res. Part A, 79(1), 1-5 (2006).

Lu J, Hou R, Booth C, Yang S, Snyder M. Defined culture conditions of human embryonic stem cells. PNAS USA. 103(15):5688-93, 2006.

Ludwig TE, Levenstein ME, Jones JM, Berggren WT, Mitchen ER, Frane JL, Crandall LJ, Daigh CA, Conard KR, Piekarczyk MS, Lianas RA, Thomson JA. Derivation of human embryonic stem cells in defined conditions. Nat Biotechnol. 24(2):185-7, 2006.

Lutolf MP and Hubbell JA. Synthetic biomaterials as instructive extracellular microenvironments for morphogenesis in tissue engineering. Nat Biotechnol 23: 47-55, 2005.

Lutolf MP and Hubbell JA. Synthesis and physicochemical characterization of end-linked poly(ethylene glycol)-co-peptide hydrogels formed by Michael-type addition. Biomacromolecules 4: 713-722, 2003.

Massia SP and Hubbell JA. An RGD spacing of 440 nm is sufficient for integrin alpha V beta 3-mediated fibroblast spreading and 140 nm for focal contact and stress fiber formation. J Cell Biol 114: 1089-1100, 1991.

Massia SP, Rao SS, and Hubbell JA. Covalently immobilized laminin peptide Tyr-Ile-Gly-Ser-Arg (YIGSR) supports cell spreading and co-localization of the 67-kilodalton laminin receptor with alpha-actinin and vinculin. J Biol Chem 268: 8053-8059, 1993.

Massia SP and Hubbell JA. Human endothelial cell interactions with surface-coupled adhesion peptides on a nonadhesive glass substrate and two polymeric biomaterials. J Biomed Mater Res 25: 223-242, 1991.

Massia SP and Hubbell JA. Immobilized amines and basic amino acids as mimetic heparin-binding domains for cell surface proteoglycan-mediated adhesion. J Biol Chem 267: 10133-10141, 1992.

Massia SP and Hubbell JA. Vascular endothelial cell adhesion and spreading promoted by the peptide REDV of the IIICS region of plasma fibronectin is mediated by integrin alpha 4 beta 1. J Biol Chem 267: 14019-14026, 1992.

Model, M., and Healy, K.E., "Quantification of the Surface Density of a Fluorescent Label with the Optical Microscope," J. Biomed. Mater. Res., 50, 90-96 (2000).

Park, S., and Healy, K.E., "Nanoparticulate DNA Packaging Using Terpolymers of Poly(lysine-g-lactide-b-ethylene glycol)," Bioconjugate Chemistry, 14(2), 311-319 (2003).

Park, S., Bearinger, J.P., Lautenschlager, E.P., Castner, D.G., Healy, K.E., "Surface Modification of Poly(ethylene terephthalate) Anigoplasty Balloons with a Hydrophilic Poly(acrylamide-co-ethylene glycol) Interpenetrating Network Coating," J. Biomed. Mater. Res., 53(5), 568-576 (2000).

Pratt, A.B., et al., Synthetic Extracellular Matrices for In Situ Tissue Engineering, Biotechnology and Bioengineering, vol. 86, No. 1, Apr. 5, 2004, 27-36.

Rezania, A., Thomas, C.H., and Healy, K.E., "A Probabilistic Approach to Measure the Strength of Bone Cell Adhesion to Chemically Modified Surfaces," Annals of Biomedical Engineering, 25, 190-203 (1997).

Rezania, A., Johnson, B., Lefkow, A.R., and Healy, K.E., "Bioactivation of Metal Oxide Surfaces: I. Surface Characterization and Cell Response," Langmuir, 15, 6931-6939 (1999).

Rezania, A., and Healy, K.E., "Biomimetic Peptide Surfaces that Regulate Adhesion, Spreading, Cytoskeletal Organization, and Mineralization of the Matrix Deposited by Osteoblast-like Cells," Biotechnology Progress, 15(1), 19-32 (1999).

Rezania, A., and Healy, K.E., "Biomolecular Surface Engineering of Materials for Controlling Bone Cell Adhesion and Spreading," Mat. Res. Soc. Symp. Proc., 530, 99-103 (1998).

Rezania, A., and Healy, K.E., "Integrins Subunits Responsible for Adhesion of Human Osteoblast-Like Cells to Biomimetic Peptide Surfaces," J. Ortho. Res., 17(4), 615-623 (1999).

Rezania, A., Thomas, C.H., and Healy, K.E., "The Detachment Strength and Morphology of Bone Cells Contacting Materials Modified with a Peptide Sequence Found within Bone Sialoprotein," J. Biomedical Materials Res., 37(1), 9-19 (1997).

Rezania, A., and Healy, K.E., "The Effect of Peptide Surface Density on Mineralization of a Matrix Deposited by Osteogenic Cells," J.Biomed. Mater. Res., 52, 595-600 (2000).

Saha et al., Journal of Biomedical Materials Research Part A, Biomimetric interfacial interpenetration polymer networks control neural stem cell behavior, (2007), 81(1):240-249.

Skottman H and Hovatta O. Culture conditions for human embryonic stem cells. Reproduction. 132(5):691-8, 2006.

Stile, R. A., Shull, K.R., and Healy, K. E., "Axisymmetric Adhesion Test to Examine the Interfacial Interactions between Biologically-Modified Networks and Models of the Extracellular Matrix," Langmuir, 19, 1853-1860 (2003).

Stile R.A., Chung E., Burghardt, W.R., Healy, K.E., "Poly(N-isopropylacrylamide)-based Semi-Interpenetrating Polymer Networks for Tissue Engineering Applications. Effects of Linear Poly(acrylic acid) Chains on Rheology," J. Biomater. Sci. Polym. Ed., 15(7), 865-878 (2004).

Stile, R.A., and Healy, K.E., "Poly(N-isopropylacrylamide)-based Semi-Interpenetrating Polymer Networks for Tissue Engineering Applications Effects of Linear Poly(acrylic acid) Chains on Phase Behavior," Biomacromolecules, 3, 591-600 (2002).

Stile, R.A., Burghardt, W.R., and Healy, K.E., "Synthesis and Characterization of Injectable Poly(N-isopropylacrylamide)-based Hydrogels that Support Tissue Formation In Vitro," Macromolecules, 32, 7370-7379 (1999).

Stile, R.A., and Healy, K.E., "Thermo-Responsive Peptide-Modified Hydrogels for Tissue Regeneration," Biomacromolecules, 2, 185-194 (2001).

Stojkovic P. Lako M. Przyborski S. Stewart R. Armstrong L. Evans J. Zhang X. Stojkovic M. Human-serum matrix supports undifferentiated growth of human embryonic stem cells. Stem Cells. 23(7):895-902, 2005.

Thomas, C.H., L'Hoest, J-B., Castner, D.G., McFarland, C.D., and Healy, K.E., "Materials Designed to Control and Examine the Function of Single Cells," Mat. Res. Soc. Symp. Proc., 530, 55-58 (1998).

Whang, K., Goldstick, T.K., Healy, K.E., "A Biodegradable Polymer Scaffold for Delivery of Osteotropic Factors," Biomaterials, 21, 2545-2551 (2000).

* cited by examiner

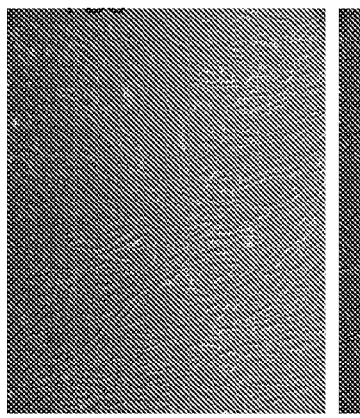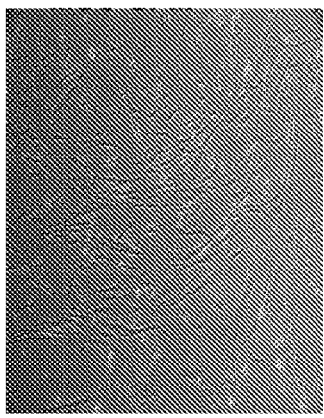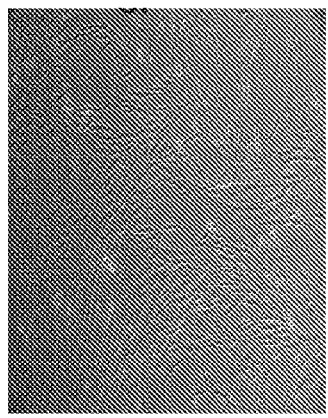
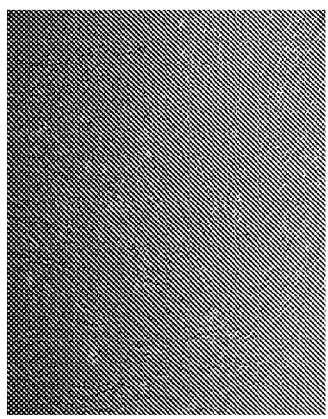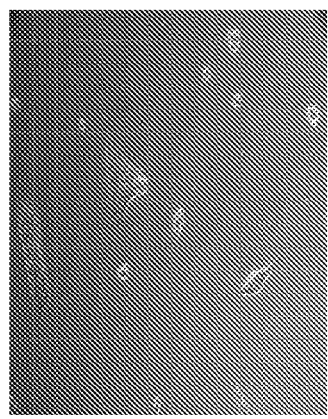
FIG. 17A     FIG. 17B     FIG. 17C

US 8,354,274 B2

SYNTHETIC SURFACES FOR CULTURING CELLS IN CHEMICALLY DEFINED MEDIA

RELATED APPLICATION(S)

This application claims the benefit of U.S. Provisional Application Ser. No. 61/062,890 filed Jan. 30, 2008 and entitled "Synthetic Surfaces for Culturing Undifferentiated Stem Cells in Chemically Defined Media" and U.S. Provisional Application Ser. No. 61/062,937 filed Jan. 30, 2008 and entitled "Stem Cell Article and Screening."

FIELD

The present disclosure relates to cell culture articles, and more particularly to articles for supporting the culture of undifferentiated stem cells in a chemically defined medium.

BACKGROUND

Pluripotent stem cells such as human embryonic stem cells (hESCs) have the ability to differentiate into any of the three germ layers, giving rise to any adult cell type in the human body. This unique property provides a potential for developing new treatments for a number of serious cell degenerative diseases, such as diabetes, spinal chord injury, heart diseases and the like. However there remain obstacles in the development of such hESC-based treatments. Such obstacles include obtaining and maintaining adequate numbers of undifferentiated hESCs in cell and tissue culture and controlling their differentiation in order to produce specific cell types. Stem Cell Cultures, such as hESC cell cultures are typically seeded with a small number of cells from a cell bank or stock and then amplified in the undifferentiated state until differentiation is desired for a given therapeutic application. To accomplish this, the hESC or their differentiated cell populations are currently cultured in the presence of surfaces or media containing animal-derived components, such as feeder layers, fetal bovine serum, or MATRIGEL™. These animal-derived additions to the culture environment expose the cells to potentially harmful viruses or other infectious agents which could be transferred to patients or compromise general culture and maintenance of the hESCs. In addition, such biological products are vulnerable to batch variation, immune response and limited shelf-life.

While undifferentiated stem cells have been grown in chemically defined media on animal-derived surfaces such as MATRIGEL™ and proteins such as serum proteins or extracellular matrix proteins, to date, a completely animal product free system employing a chemically defined medium and a synthetic non-protein surface has not been identified for long-term culturing of undifferentiated stem cells.

BRIEF SUMMARY

The present disclosure describes synthetic surfaces that may be useful in the culture of eukaryotic cells including stem cells and undifferentiated stem cells in chemically defined media. Undifferentiated stem cells may remain undifferentiated for 5, 7, 10 or more passages when cultured on the synthetic substrates.

In various embodiments, a cell culture article includes a substrate having a surface. A swellable (meth)acrylate layer is disposed on the surface of the substrate. The swellable (meth)acrylate layer is formed from a composition that includes a carboxyl group-containing (meth)acrylate monomer, a cross-linking (di- or higher-functional) (meth)acrylate monomer, and a hydrophilic monomer capable of polymerizing with the carboxyl group-containing (meth)acrylate monomer and the cross-linking (meth)acrylate monomer. The swellable (meth)acrylate layer has an equilibrium water content in water of between about 5% and about 70%. A peptide is conjugated to the swellable (meth)acrylate layer. The peptide contains an RGD amino acid sequence. The cell culture article may support culture and maintenance of undifferentiated stem cells, such as human embryonic stem cells, in a chemically defined medium.

In various embodiments, a method for producing a cell culture article includes disposing monomers on a substrate surface of the cell culture article. The monomers disposed on the surface include a carboxyl group-containing (meth)acrylate monomer, a cross-linking (meth)acrylate monomer, and a hydrophilic monomer capable of polymerizing with the carboxyl group-containing (meth)acrylate monomer and the cross-linking (meth)acrylate monomer. The method further includes polymerizing the monomers on the substrate surface to form a swellable (meth)acrylate layer having an equilibrium water content in water of between about 5% and about 70%. The method also includes conjugating to the swellable (meth)acrylate layer a peptide which may be an RGD-containing polypeptide.

One or more of the various embodiments presented herein provide one or more advantages over prior surfaces for culturing stem cells, particularly undifferentiated stem cells. For example, the synthetic surfaces reduce potential contamination issues associated with surfaces having components obtained from or derived from animal sources. Such surfaces may also provide for improved shelf life compared to those surfaces with biological components. The ability to culture undifferentiated stem cells in chemically-defined media further reduces potential contamination issues. In addition, there will likely be less batch to batch variation in the performance capability of the synthetic surfaces or chemically defined media, resulting in improved reproducibility of culture results and expectations. These and other advantages will be readily understood from the following detailed descriptions when read in conjunction with the accompanying drawings

BRIEF DESCRIPTION OF THE DRAWINGS

FIGS. 17A-C are images comparing the survival/proliferation of human mesenchymal stem cells (hMSC) on SAP-BSP peptide-acrylate with standard TCT plastic cell culture ware on day 7 post-seeding.

Figure 1A:
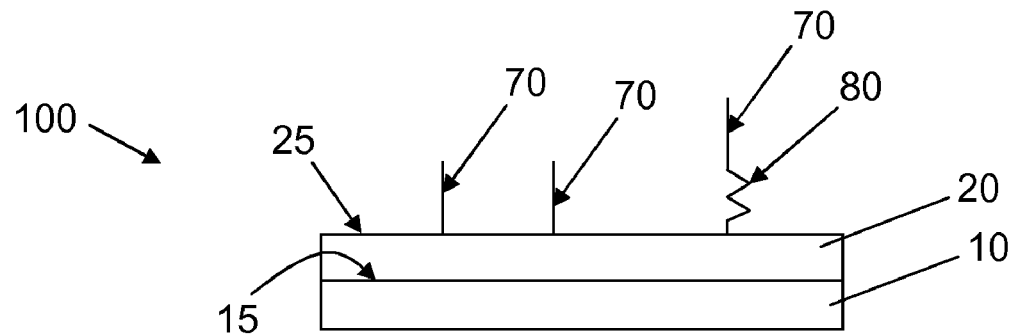
FIGS. 1A-B are schematic diagrams of side views of synthetic swellable (meth)acrylate layer coated articles.
Figure 1B:
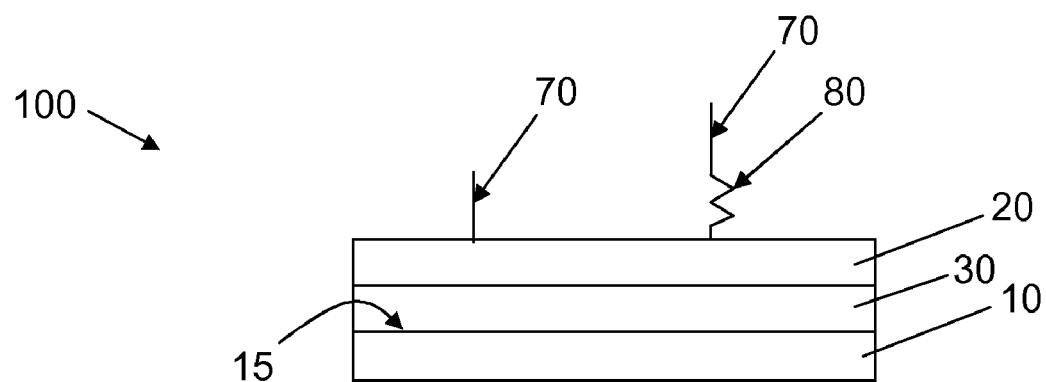
Figure 2A:
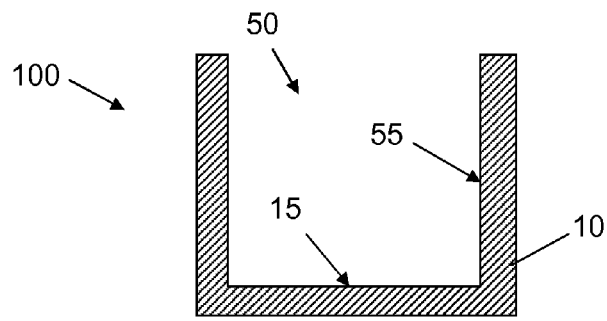
FIG. 2A-C are schematic diagrams of cross sections of cell culture articles having a well. Uncoated (2A); coated surface (2B); and coated surface and side walls (2C).

The drawings depicted in FIGS. 1-2 are not necessarily to scale. Like numbers used in the FIGS. 1-2 refer to like components. However, it will be understood that the use of a number to refer to a component in a given figure is not intended to limit the component in the other figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "providing" an article in the context of a method means producing, purchasing, fabricating, supplying or otherwise obtaining the article so that the article may be used in the method.

Peptide sequences are referred to herein by their one letter and by their three letter codes. These codes may be used interchangeably.

As used herein, "monomer" means a compound capable of polymerizing with another monomer, (regardless of whether the "monomer" is of the same or different compound than the other monomer), which compound has a molecular weight of less that about 1000 Dalton. In many cases, monomers will have a molecular weight of less than about 400 Dalton.

As used herein, "synthetic coating" or "synthetic polymeric layer" means a layer of polymer material disposed on a cell culture substrate. The polymeric coating does not include animal-derived materials or ingredients. For example, a synthetic coating does not have proteins isolated from an animal source. In embodiments, swellable (meth)acrylate layers (SA layers) as described herein provide a synthetic coating. In embodiments, a suitable adhesion polypeptide or combinations of polypeptides may be conjugated to the synthetic coating layer forming swellable(meth)acrylate-peptide conjugated layers (SAP layers).

As used herein "peptide" and "polypeptide" mean a sequence of amino acids that may be chemically synthesized or may be recombinantly derived, but that are not isolated as entire proteins from animal sources. For the purposes of this disclosure, peptides and polypeptides are not whole proteins. Peptides and polypeptides may include amino acid sequences that are fragments of proteins. For example peptides and polypeptides may include sequences known as cell adhesion sequences such as RGD. In some embodiments, the peptides of the present invention are between three and 30 amino acids in length. In some embodiments, the peptides of the present invention are 15mers, 12mers, 10mers or the like. In embodiments, peptides may include linker sequences such as KGG (LysGlyGly) or KYG (LysTyrGly) which provide a Lys residue which may provide a functional group for conjugation of the peptide. Peptides may be acetylated (e.g. Ac-LysGlyGly) or amidated (e.g. SerLysSer-NH$_2$) to protect them from being broken down by, for example, exopeptidases. It will be understood that these modifications are contemplated when a sequence is disclosed. In additional embodiments, peptides may be conjugated to spacer moieties such as PEO. PEO may be present as, for example, PEO$_4$ or PEO$_{12}$ or any length spacer.

As used herein, a "(meth)acrylate monomer" means a compound having at least one ethylenically unsaturated moiety (an acrylate moiety or a methacrylate moiety). "Poly(meth)acrylate", as used herein, means a polymer formed from one or more monomers including at least one (meth)acrylate monomer.

The term "hydrogel" has been used to describe cell culture surfaces. "Hydrogel" has been variously defined to include a gel or gelatin that can absorb water in an amount greater than or equal to 30% or up to 10,000% of its dry weight. When contacted with water, hydrogels swell but do not dissolve. The term "hydrogel" is a very broad term, describing a wide range of materials, having a wide range of water swelling and water absorbing characteristics.

As used herein, "swellable (meth)acrylate" or "SA" means a polymer matrix made from at least one ethylenically unsaturated monomer (acrylate or methacrylate monomers) having at least some degree of cross linking, and also having water absorbing or water swelling characteristics. Swellable (meth) acrylates may be synthetic. That is, they do not contain ingredients that are derived from animals or animal extracts. Swellable (meth)acrylates may be conjugated to polypeptides or proteins ("swellable (meth)acrylate-polypeptide", "SA-polypeptide" or "SAP"). Polypeptides or peptides are fragments of proteins and may be synthesized, making them synthetic, non-animal-derived materials. Proteins may be isolated from animal-derived material. This SA and SAP material may be referred to as a layer, a coating, a surface, a material, or any other term known in the art to refer to a surface suitable for cell culture. The particular polypeptide sequence may be further identified. For example, a SAP surface may be conjugated with a RGD-containing polypeptide and may be identified as SAP-RGD. Or, a SAP surface may be conjugated to a particular RGD-containing peptide, for example KGGNGEPRGDTYRAY (SEQ ID NO:4), incorporates the RGD adhesion epitope of Bonesialo protein (BSP) from mouse may be conjugated to a swellable (meth)acrylate polymer (SAP) to form an SAP-BSP coating. In embodiments of the present disclosure, the term "swellable (meth) acrylate" represents a range of cross-linked acrylate or methacrylate materials which absorb water, swell in water, and do not dissolve in water. This water-absorbing characteristic can be described and measured by equilibrium water content (EWC) as shown by Formula 1:

$$EWC(\%) = [(Wgel - Wdry)/(Wgel)]*100. \quad \text{Formula 1}$$

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. Accordingly, a SA surface formed from a mixture of monomers comprising a hydrophilic monomer, a cross-linking monomer and a carboxyl group-containing monomer may be formed from a mixture consisting essentially of, or consisting of, a hydrophilic monomer, a cross-linking monomer and a carboxyl group-containing monomer.

The present disclosure describes, inter alia, articles having synthetic surfaces for culturing undifferentiated stem cells. The surfaces may support proliferation and maintenance of undifferentiated stem cells in chemically defined media.

1. Cell Culture Article

Referring to FIG. 1A, a schematic diagram of a side view of an article 100 for culturing cells is shown. The article 100 includes a base material substrate 10 having a surface 15. A swellable (meth)acrylate coating layer 20 is disposed on the surface 15 of the substrate or base material 10. While not shown, it will be understood that swellable (meth)acrylate coating 20 may be disposed on a portion of substrate or base material 10. The substrate or base material 10 may be any material suitable for culturing cells, including a ceramic substance, a glass, a plastic, a polymer or co-polymer, any combinations thereof, or a coating of one material on another. Such substrate or base materials 10 include glass materials such as soda-lime glass, pyrex glass, vycor glass, quartz glass; silicon; plastics or polymers, including dendritic polymers, such as poly(vinyl chloride), poly(vinyl alcohol), poly (methyl methacrylate), poly(vinyl acetate-co-maleic anhydride), poly(dimethylsiloxane) monomethacrylate, cyclic olefin polymers, fluorocarbon polymers, polystyrenes, polypropylene, polyethyleneimine; copolymers such as poly (vinyl acetate-co-maleic anhydride), poly(styrene-co-maleic anhydride), poly(ethylene-co-acrylic acid) or derivatives of these or the like.

As used herein, "cyclic olefin copolymer" means a polymer formed from more than one monomer species, where at least one of the monomer species is a cyclic olefin monomer and at least one other monomer species is not a cyclic olefin monomer species. In many embodiments, cyclic olefin copolymers are formed from ethylene and norbonene monomers. Cyclic olefin copolymer resins are commercially available with trade name of TOPAS® from Boedeker Plastics, Inc.

Examples of articles 100 suitable for cell culture include single and multi-well plates, such as 6, 12, 96, 384, and 1536 well plates, jars, petri dishes, flasks, multi-layered flasks, beakers, plates, roller bottles, slides, such as chambered and multichambered culture slides, tubes, cover slips, bags, membranes, hollow fibers, beads and microcarriers, cups, spinner bottles, perfusion chambers, bioreactors, CellSTACK® and fermenters.

Swellable (meth)acrylate (SA) coating 20 provides a surface 25 on which one or more polypeptides 70 may be conjugated. Of course, the one or more polypeptides 70 may also be conjugated to the SA layer 20 at locations beneath the surface 25. As used herein, "conjugated" means covalently bound. Covalent binding of polypeptide 70 to SA layer 20 may occur through a linker. The polypeptide 70 may be cyclic or linear, or may contain portions that are cyclic and portions that are linear.

For the purposes of this disclosure "peptide" and "polypeptide" can be used interchangeably. Any suitable SA coating 20 may be applied to or formed on the surface 15 of the substrate 10. In various embodiments, the SA coating comprises, consists essentially of, or consists of, reaction products of one or more hydrophilic (meth)acrylate monomer, one or more di- or higher-functional (meth)acrylate monomer ("cross-linking" (meth)acrylate monomer), and one or more carboxyl group-containing monomers. Any suitable hydrophilic (meth)acrylate monomer may be employed. Examples of suitable hydrophilic (meth)acryate monomers include 2-hydroxyethyl methacrylate, di(ethylene glycol)ethyl ether methacrylate, ethylene glycol methyl ether methacrylate, and the like. In various embodiments, hydrophilic monomers other than (meth)acrylates may be used to form the SA coating. These other hydrophilic monomers may be included in addition to, or in place of, hydrophilic (meth)acrylate monomers. Such other hydrophilic monomers should be capable of undergoing polymerizing with (meth)acrylate monomers in the mixture used to form the swellable (meth)acrylate layer 20. Examples of other hydrophilic monomers that may be employed to form the SA coating include 1-vinyl-2-pyrrolidone, acrylamide, 3-sulfopropyldimethyl-3-methylacrylamideopropyl-ammonium, and the like. Regardless of whether a (meth)acrylate monomer or other monomer is employed, a hydrophilic monomer, in various embodiments, has a solubility in water of 1 gram or more of monomer in 100 grams of water. Any suitable di- or higher-functional (meth)acrylate monomer, such as tetra(ethylene glycol) dimethacrylate or tetra(ethylene glycol) diacrylate, may be employed as a cross-linking monomer. Any suitable (meth)acrylate monomer having a carboxyl functional group available for conjugating with a polypeptide 70 after the monomer is incorporated into the SA coating 20 by polymerization may be employed. The carboxyl functional group enables conjugation of a peptide or polypeptide using NHS/EDC chemistry. Examples of suitable carboxyl group-containing (meth)acrylate include 2-carboxyethyl acrylate and acrylic acid.

In various embodiments, the SA layer 20 is formed from monomers comprising (by percent volume): hydrophilic (meth)acrylate monomer (~60-90), carboxyl group-containing (meth)acrylate monomer (~10-40), and cross-linking (meth)acrylate monomer (~1-10), respectively. It will be understood that the equilibrium water content (EWC) of the SA layer may be controlled by the monomers chosen to form the SA layer. For example, a higher degree of hydrophilicity and a higher percentage of the hydrophilic monomer should result in a more swellable SA layer with a higher EWC. However, this may be attenuated by increasing the percentage, or increasing the functionality, of the cross-linking monomer, which should reduce the ability of the SA layer to swell and reduce the EWC.

In various embodiments, the specific monomers employed to form the SA layer and their respective weight or volume percentages are selected such that the resulting SA layer has an EWC of between about 5% and about 70%. Due in part to the use of a carboxyl containing monomer in the SAs of various embodiments described herein, the EWC may be pH dependent. For example, the EWC of particular SAs may be higher in phosphate buffer (pH 7.4) than in distilled, deionized water (pH ~5). In various embodiments, the EWC of an SA layer in distilled, deionized water is the EWC (in water) of SAs of the present invention may range between 5% and 70%, between 5% and 60%, between 5% and 50%, between 5 and 40%, between 5% and 35%, between 10% and 70%, between 10% and 50% between 10 and 40%, between 5% and 35%, between 10% and 35% or between 15% and 35% in water. In further embodiments, after the swellable (meth)acrylates have been conjugated with peptides (SAP), the EWC of embodiments of SAPs of the present invention may be, for example, between 10-40% in water (data not shown).

In cell culture, prepared surfaces are exposed to an aqueous environment for extended periods of time. Surfaces that absorb significant water, surfaces that are highly hydrogel-like, may tend to delaminate from a substrate when exposed to an aqueous environment. This may be especially true when these materials are exposed to an aqueous environment for extended periods of time, such as for 5 or more days of cell culture. Accordingly, it may be desirable for SA and SAP layers to have lower EWC measurements, so that they do not absorb as much water, to reduce the likelihood of delaminating. For example, SA surfaces having an EWC below 40% may be particularly suitable for supporting cells in culture, including human embryonic stem cells.

It will be understood that the conjugation of a polypeptide 70 to an SA layer 20 may affect the swellability and equilibrium water content (EWC) of the SA layer, generally increasing the EWC. The amount of polypeptide conjugated to SA layers tends to be variable and can change depending on the thickness of the SA layer. Accordingly, the EWC of a SA-polypeptide layers prepared in accordance with a standard protocol may be variable. For purposes of reproducibility, it may be desirable to measure the EWC of SA layers prior to conjugation with a polypeptide. With this noted, in some embodiments, after the SAs have been conjugated with polypeptides (SA-polypeptide), the EWC of embodiments of SA-polypeptide layers may be between about 10% and about 40% in water.

In various embodiments, the SA layer 20 includes polymerized (meth)acrylate monomers formed from a mixture including hydroxyethyl methacrylate, 2-carboxyethylacrylate, and tetra(ethylene glycol) dimethacrylate. In numerous embodiments, the ratio (by volume) of hydroxyethyl methacrylate, 2-carboxyethylacrylate, and tetra(ethylene glycol) dimethacrylate used to form the SA layer 20 is about 80/20/3 (v/v/v), respectively. In some embodiments, the SA is formulated using the following liquid aliquots of monomers (by volume): hydroxyethyl methacrylate (~60-90), 2-carboxyethylacrylate (~10-40), and tetra(ethylene glycol) dimethacrylate (~1-10), respectively. In numerous embodiments, the SA layer 20 consists essentially of polymerized hydroxyethyl methacrylate, 2-carboxyethylacrylate, and tetra(ethylene glycol) dimethacrylate monomers. In various embodiments, the SA layer 20 is substantially free of polypeptide crosslinkers.

In numerous embodiments, the SA is formulated using the monomers (by volume for liquid monomers or weight for solid monomers): Monomer X (80), 2-carboxyethylacrylate (20), and tetra(ethylene glycol) dimethacrylate (3). Monomer X is: Hydroxypropyl methacrylate, 2-Hydroxyethyl acrylate, 1-vinyl-2-pyrrolidone, di(ethylene glycol) ethyl ether methacrylate, acrylamide, ethylene glycol methyl ether methacrylate, or 3-sulfopropyldimethyl-3-methacrylamidopropyl-ammonium.

Any suitable polypeptide 70 may be conjugated to the SA layer 20. Preferably, polypeptide 70 includes an amino acid capable of conjugating to the SA layer 20; e.g. via the free carboxyl group formed from the carboxyl group-containing (meth)acrylate monomer. By way of example, any native or biomimetic amino acid having functionality that enables nucleophilic addition; e.g. via amide bond formation, may be included in polypeptide 70 for purposes of conjugating to SA layer 20. Lysine, homolysine, ornithine, diaminoproprionic acid, and diaminobutanoic acid are examples of amino acids having suitable properties for conjugation to a carboxyl group of the SA layer 20. In addition, the N-terminal alpha amine of a polypeptide may be used to conjugate to the carboxyl group, if the N-terminal amine is not capped. In various embodiments, the amino acid of polypeptide 70 that conjugates with the SA layer 20 is at the carboxy terminal position or the amino terminal position of the polypeptide 70.

In numerous embodiments, the polypeptide 70, or a portion thereof, has cell adhesive activity; i.e., when the polypeptide 70 is conjugated to the SA layer, the peptide allows a cell to adhere to the surface containing the SA-P layer. By way of example, the polypeptide 70 may include an amino sequence, or a cell adhesive portion thereof, of collagen, keratin, gelatin, fibronectin, vitronectin, laminin, or the like. In various embodiments, polypeptide 70 includes an amino acid sequence of $Yaa_1Xaa_nArgGlyAspXaa_mYaa_1$ (SEQ ID NO:1) (RGD) where Xaa and Yaa represent any amino acid, synthetic or naturally occurring and n and m can be any integer including 0. SA layers as described herein provide a synthetic surface to which any suitable adhesion polypeptide or combinations of polypeptides may be conjugated, providing an alternative to biological substrates or serum that have unknown components. In current cell culture practice, it is known that some cell types require the presence of a biological polypeptide or combination of peptides on the culture surface for the cells to adhere to the surface and be sustainably cultured. For example, HepG2/C3A hepatocyte cells can attach to plastic culture ware in the presence of serum. It is also known that serum can provide polypeptides that can adhere to plastic culture ware to provide a surface to which certain cells can attach. However, biologically-derived substrates and serum contain unknown components. For cells where the particular component or combination of components (peptides) of serum or biologically-derived substrates that cause cell attachment are known, those known peptides can be synthesized and applied to an SA layer as described herein to allow the cells to be cultured on a synthetic surface having no or very few components of unknown origin or composition.

In some embodiments, peptide 70 includes an amino acid sequence of $Yaa_1Xaa_nArgGlyAspXaa_mYaa_1$ (SEQ ID NO:1), where n is an integer of 0 to 4, m is an integer of 0 to 5, 1 is 0 or 1 provided that the peptide 70 includes at least one Yaa, each Xaa is independently any native or biomimetic amino acid, and Yaa is any native or biomimetic amino acid, where either Xaa or Yaa has functionality that enables nucleophilic addition; e.g. via amide bond formation, to a free carboxyl group of SA surface. In various embodiments, Xaa or Yaa may be lysine, cysteine, homocysteine, penicillamine, ornithine, diaminoproprionic acid, or diaminobutanoic acid.

In some embodiments, polypeptide 70 includes an amino acid sequence of $ZaaXaa_nArgGlyAspXaa_mBaa$ (SEQ ID NO:2), where n is an integer of 0 to 4, m is an integer of 0 to 5, each Xaa is independently any native or biomimetic amino acid, and Zaa and Baa are each independently any native or biomimetic amino acid having covalent bonds formed between atoms of their respective side chains to form a cyclic polypeptide or portion thereof. In various embodiments, Zaa and Baa are linked via a disulfide bond. For example, Zaa or Baa may be cysteine, homocysteine or penicillamine. In some embodiments, Zaa and Baa are linked via an amide bond. For example, one of Zaa and Baa is an amino acid with a side chain having a free amino group, such as lysine, ornithine, diaminoproprionic acid, or diaminobutanoic acid, and the other of Zaa and Baa is an amino acid with a side chain having a free carboxyl group, such as aspartic acid, glutamic acid, or homoglutamic acid. In some embodiments, a polypeptide 70 according to SEQ ID NO:2 may be further defined as including an amino acid sequence of $Yaa_1\ Xaa_mZaaXaa_nArgGlyAspXaa_mBaa\ Xaa_mYaa_1$ (SEQ ID NO:3), where n is an integer of 0 to 4, m is an integer of 0 to 5, 1 is 0 or 1 provided that the polypeptide includes at least one Yaa or Xaa, each Yaa and Xaa is independently any native or biomimetic amino acid, and Zaa and Baa are each independently any native or biomimetic amino acid having covalent bonds formed between atoms of their respective side chains to form a cyclic portion of the polypeptide, and Yaa or Xaa is any native or biomimetic amino acid having functionality that enables nucleophilic addition; e.g. via amide bond formation, to a free carboxyl group of SA layer. While not intending to be bound by theory, it is believed that cyclization of a polypeptide containing an RGD sequence may help maintain a conformation structure in aqueous environments to preserve biologic function relative to linear counterpart polypeptides, particularly when the polypeptides consist of relatively few amino acids; e.g. less than 10.

In some embodiments, polypeptide 70 comprises an amino acid sequence of LysGlyGlyAsnGlyGluProArgGlyAspThrTyrArgAlaTry (SEQ ID NO:4). In some embodiments, polypeptide 70 consists essentially of an amino acid sequence of AsnGlyGluProArgGlyAspThrTyrArgAlaTyr (SEQ ID NO:5). In some embodiments, peptide 70 consists essentially of an amino acid sequence of LysGlyGlyLys$^4$AsnGlyGluProArgGlyAspThrTyrArgAlaTyr Asp$^{17}$ (SEQ ID NO:6), where Lys$^4$ and Asp$^{17}$ together form an amide bond to cyclize a portion of the polypeptide. In some embodiments, peptide 70 consists essentially of an amino acid sequence of LysGlyGly Lys$^4$GluProArg GlyAspThrTyrArgAsp$^{13}$ (SEQ ID NO:7), where Lys$^4$ and Asp$^{13}$ together form an amide bond to cyclize a portion of the polypeptide. In some embodiments, polypeptide 70 consists essentially of an amino acid sequence of LysGlyGly Cys$^4$AsnGlyGluProArgGlyAspThrTyrArgAlaTyrCys$^{17}$ (SEQ ID NO:8), where Cys$^4$ and Cys$^{17}$ together form a disulfide bond to cyclize a portion of the polypeptide. In some embodiments, polypeptide 70 consists essentially of an amino acid sequence of LysGlyGly Cys$^4$GluProArgGlyAspThrTryArgCys$^{13}$ (SEQ ID NO:9), where Cys$^4$ and Cys$^{13}$ together form a disulfide bond to cyclize a portion of the polypeptide. In various embodiments, peptide 70 consists essentially of an amino acid sequence of XaaGlyGlyAsnGlyGluProArgGlyAspThrTyrArgAlaTyr (SEQ ID NO:10), wherein Xaa is any amino acid. In numerous embodiments, Xaa of SEQ ID NO:10 is lysine. In some embodiments, polypeptide 70 consists essentially of an amino acid sequence of GlyArgGlyAspSerProLys (SEQ ID NO:11).

In some embodiments, polypeptide 70 consists essentially of an amino acid sequence of LysGlyGlyAlaValThrGlyArgGlyAspSerProAlaSerSer (SEQ ID NO:12).

For any of the polypeptide sequences discussed herein, it will be understood that a conservative amino acid may be substituted for a specifically identified amino acid. A "conservative amino acid", as used herein, refers to an amino acid that is functionally similar to a second amino acid. Such amino acids may be substituted for each other in a polypeptide with a minimal disturbance to the structure or function of the polypeptide according to well known techniques. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (I), Glutamic acid (E), Asparagine (N), Glutamine (Q).

A linker or spacer 80, such as a repeating poly(ethylene glycol) linker or any other suitable linker, may be used to increase distance from polypeptide 70 to surface 25 of swellable (meth)acrylate layer 20. The linker 80 may be of any suitable length. For example, if the linker is a repeating poly(ethylene glycol) linker, the linker may contain between 2 and 10 repeating ethylene glycol units. In some embodiments, the linker is a repeating poly(ethylene glycol) linker having about 4 repeating ethylene glycol units. All, some, or none of the polypeptides 70 may be conjugated to SA layer 20 via linkers 80. A SA layer chain which provides a conjugation group may also act as spacer for conjugated peptides. Other potential linkers are polypeptide linkers such as poly(glycine) or poly(β-alanine).

Polypeptide 70 may be conjugated to the SA layer 20 at any density, preferably at a density suitable to support culture of undifferentiated stem cells or other cell types. Polypeptide 70 may be conjugated to SA layer 20 at a density of between about 1 pmol per mm$^2$ and about 50 pmol per mm$^2$ of surface 25 of SA coating 20, which can be estimated by the area of surface 15 of base material substrate 10 that is coated in embodiments where surface 15 is uniformly coated by SAP layer 20. For example, the polypeptide may be present at a density of greater than 5 pmol/mm$^2$, greater than 6 pmol/mm$^2$, greater than 7 pmol/mm$^2$, greater than 8 pmol/mm$^2$, greater than 9 pmol/mm$^2$, greater than 10 pmol/mm$^2$, greater than 12 pmol/mm$^2$, greater than 15 pmol/mm$^2$, or greater than 20 pmol/mm$^2$ of the surface 25 of the SA coating 20. It will be understood that the amount of polypeptide 70 present can vary depending on the composition of the SA layer 20, the thickness of the SA layer 20 and the nature of the polypeptide 70 itself. As discussed below in the Examples, higher densities of polypeptide 70 may be better able to support attachment and proliferation of undifferentiated stem cells in a chemically defined medium.

(Meth)acrylate monomers may be synthesized as known in the art or obtained from a commercial vendor, such as Polysciences, Inc., Sigma Aldrich, Inc., and Sartomer, Inc. Polypeptides 70 may be synthesized as known in the art (or alternatively produced through molecular biological techniques) or obtained from a commercial vendor, such as American Peptide Company, CEM Corporation, or GenScript Corporation. Linkers 80 may be synthesized as known in the art or obtained from a commercial vendor, such as discrete polyethylene glycol (dPEG) linkers available from Quanta BioDesign, Ltd.

As shown in FIG. 1B, an intermediate layer 30 may be disposed between surface 15 of base material 10 and the SA coating 20. Intermediate layer 30 may be configured to improve binding of coating 20 to substrate 10, to facilitate monomer spreading, to render portions of the surface 10 that are uncoated cytophobic to encourage cell growth on coated areas, to provide a substrate compatible with a monomer or solvent where the monomer or solvent is incompatible with the base material 10, to provide topographical features if desired through, for example, patterned printing, or the like. For example, if substrate 10 is a glass substrate, it may be desirable to treat a surface of the glass substrate with an epoxy coating or a silane coating. For various polymer base materials 10 it may be desirable to provide an intermediate layer 30 of polyamide, polyimide, polypropylene, polyethylene, or poly(meth)acrylate. While not shown, it will be understood that SA coating 20 may be disposed on a portion of intermediate layer 30. It will be further understood that intermediate layer 30 may be disposed on a portion of base material 10.

In various embodiments, surface 15 of base material 10 is treated, either physically or chemically, to impart a desirable property or characteristic to the surface 15. For example, and as discussed below, surface 15 may be corona treated or plasma treated. Examples of vacuum or atmospheric pressure plasma include radio frequency RF and microwave plasmas both primary and secondary, dielectric barrier discharge, and corona discharge generated in molecular or mixed gases including air, oxygen, nitrogen, argon, carbon dioxide, nitrous oxide, or water vapor.

SA coating layer 20, whether disposed on an intermediate layer 30 or base material 10, preferably uniformly coats the underlying substrate. By "uniformly coated", it is meant that the layer 20 in a given area, for example a surface of a well of a culture plate, completely coats the area at a thickness of about 5 nm or greater. While the thickness of a uniformly coated surface may vary across the surface, there are no areas of the uniformly coated surfaces through which the underlying layer (either intermediate layer 30 or base material 10) is exposed. Cell responses across non-uniform surfaces tend to be more variable than cell responses across uniform surfaces.

SA polymer coating layer 20 may have any desirable thickness. In various embodiments, the average thickness of the coating layer 20 is less than about 10 micrometers. For example, the average thickness may be less than about 5 micrometers, less than about 2 micrometers, less than about 1 micrometers, less than about 0.5 micrometers, between about 50 nm and about 300 nm, or about 0.1 micrometers.

The polymer material forming SA layer 20 may be crosslinked to any suitable degree. Low degree of crosslinking may result in partial or complete SA layer dissolution and lower polymerization reaction efficiency. In various embodiments, the crosslinking density of SA layer 20 is between about 0.9% and about 9%.

Figure 2B:
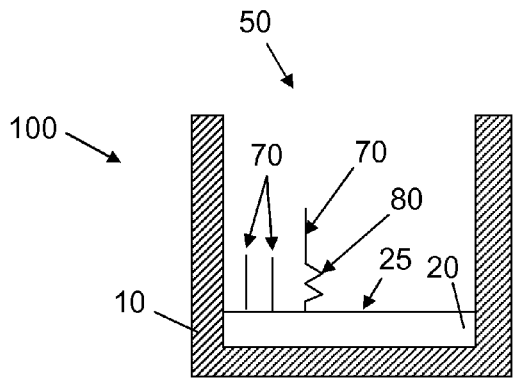
Figure 2C:
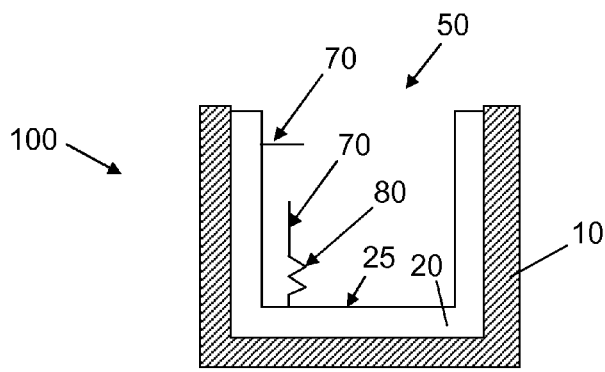

Article 100, in numerous embodiments, is cell culture ware having a surface suitable for cell culture, such as a 6, 12, 96, 384, and 1536 well plates, jars, petri dishes, flasks, multilayered flasks, beakers, plates, roller bottles, slides, such as chambered and multichambered culture slides, tubes, cover slips, bags, membranes, hollow fibers, beads and microcarriers, cups, spinner bottles, perfusion chambers, bioreactors, CellSTACK® and fermenters. In numerous embodiments these cell culture surfaces are contained in a cell culture well. Referring now to FIG. 2, article 100 formed from substrate or base material 10 may include one or more wells 50. Well 50 includes a sidewall 55 and a surface 15. Referring to FIG. 2B-C, a SA coating 20 may be disposed on surface 15 or sidewalls 55 (or, as discussed above with regard to FIG. 1 one or more intermediate layer 30 may be disposed between surface 15 or sidewall 55 and SA coating 20) or a portion thereof. As shown in FIG. 2C, 55 may be coated with SA layer 20.

In various embodiments, article 100 includes a uniformly coated layer 20 having a surface 25 with an area greater than about 5 mm$^2$. Of course, the surface 25 may be of any suitable size. When the area of the surface 15 is too small, reliable cell responses may not be readily observable because some cells, such as human embryonic stem cells, are seeded as colonies or clusters of cells (e.g., having a diameter of about 0.5 mm) and adequate surface is desirable to ensure attachment of sufficient numbers of colonies to produce a quantitative cell response. In numerous embodiments, an article 100 has a well 50 having a uniformly coated surface 15, where the surface 15 has an area greater than about 0.1 cm², greater than about 0.3 cm², greater than about 0.9 cm², or greater than about 1 cm².

2. Coating of Synthetic Swellable (meth)acrylate Layer

A synthetic swellable (meth)acrylate (SA) layer may be disposed on a surface of a cell culture article via any known or future developed process. Preferably, the synthetic SA layer provides a uniform layer that does not delaminate during typical cell culture conditions. That is, the SA layer is attached to the substrate or base material. The synthetic SA surface may be associated with or attached to the base material substrate via covalent or non-covalent interactions. Examples of non-covalent interactions that may associate the synthetic SA surface with the substrate include chemical adsorption, hydrogen bonding, surface interpenetration, ionic bonding, van der Waals forces, hydrophobic interactions, dipole-dipole interactions, mechanical interlocking, and combinations thereof.

In various embodiments, the base material substrate surface is coated according to the teachings of co-pending application Ser. No. 12/362,782, filed on even date herewith, naming Zhou et al. as inventors, and entitled CELL CULTURE ARTICLE AND SCREENING, which application is hereby incorporated herein by reference in its entirety for all purposes to the extent that it does not conflict with the disclosure presented herein.

In numerous embodiments, monomers are deposited on a surface of a cell culture article and polymerized in situ. In such embodiments, the base material will be referred to herein as the "substrate" on which the synthetic swellable (meth)acrylate material is deposited. While polymerization may be done in solution phase or in bulk phase, in embodiments of the present invention, polymerization in bulk phase, in situ polymerization, yields a cell culture surface that is a networked polymeric surface. This networked polymeric surface is not an interpenetrating polymeric network. In embodiments, the networked polymeric surface provided by in situ polymerization attaches to the substrate, does not delaminate, and survives in the aqueous environment of cell culture without delaminating for periods of time that are relevant for cell culture. In embodiments, the monomers are less than 1000 daltons.

As monomers may be viscous, it may be desirable to dilute the monomers in a suitable solvent to reduce viscosity prior to being dispensed on the surface. Reducing viscosity may allow for thinner and more uniform layers of the synthetic swellable (meth)acrylate material to be formed. One of skill in the art will be able to readily select a suitable solvent. Preferably the solvent is compatible with the material forming the cell culture article and the monomers. It may be desirable to select a solvent that is non-toxic to the cells to be cultured and that does not interfere with the polymerization reaction. Alternatively, or in addition, selection of a solvent that can be substantially completely removed or removed to an extent that it is non-toxic or no longer interferes with polymerization may be desirable. In such circumstances, it may be desirable that the solvent be readily removable without harsh conditions, such as vacuum or extreme heat. Volatile solvents are examples of such readily removable solvents.

Some solvents that may be suitable in various situations for coating articles as described herein include ethanol, isopropanol, acetyl acetate, ethyl acetate, dimethylformamide (DMF), and dimethylsulfoxide (DMSO). As described in co-pending application Ser. No. 12/362,782, filed on even date herewith, entitled CELL CULTURE ARTICLE AND SCREENING, volatile solvents, such as acetone, methanol, ethyl acetate, butanone, acetonitrile, isopropanol, and 2-butanol, and ethanol, may be particularly suitable solvents when it is desired to remove solvent prior to polymerization.

The monomers may be diluted with solvent by any suitable amount to achieve the desired viscosity and monomer concentration. Generally the monomer compositions used according to the teachings presented herein contain between about 0.1% to about 99% monomer. By way of example, the monomer may be diluted with an ethanol or other solvent to provide a composition having between about 0.1% and about 50% monomer, or from about 0.1% to about 10% monomer by volume, from about 0.1% to about 5% monomer by volume, or from about 0.1% to about 1% monomer by volume. The monomers may be diluted with solvent so that the swellable (meth)acrylate layer achieves a desired thickness. As discussed above, if the deposited monomers are too thick, a non-uniform surface may result and the coating may likely de-laminate after contact with an aqueous medium.

In various embodiments, the synthetic swellable (meth) acrylate layer is deposited on a surface of an intermediate layer that is associated with the base material via covalent or non-covalent interactions, either directly or via one or more additional intermediate layers (not shown). In such embodiments, the intermediate layer will be referred to herein as the "substrate" onto which the synthetic swellable (meth)acrylate layer is deposited.

In various embodiments, the surface of the base material is treated. The surface may be treated to improve binding of the synthetic swellable (meth)acrylate layer to the base material surface, to facilitate monomer spreading on the base material surface, or the like. Of course, the base material may be treated for similar purposes with regard to an intermediate layer. In various embodiments, the surface is plasma treated. High surface energy obtainable from such treatments may facilitate monomer spreading and uniform coating.

In addition to the monomers that form the swellable (meth) acrylate layer, a composition forming the layer may include one or more additional compounds such as surfactants, wetting agents, photoinitiators, thermal initiators, catalysts, activators, and cross-linking agents.

Any suitable polymerization initiator may be employed. One of skill in the art will readily be able to select a suitable initiator, e.g. a radical initiator or a cationic initiator, suitable for use with the monomers. In various embodiments, UV light is used to generate free radical monomers to initiate chain polymerization.

Any suitable initiator may be used. Examples of polymerization initiators include organic peroxides, azo compounds, quinones, nitroso compounds, acyl halides, hydrazones, mercapto compounds, pyrylium compounds, imidazoles, chlorotriazines, benzoin, benzoin alkyl ethers, diketones, phenones, or mixtures thereof. Examples of suitable commercially available, ultraviolet-activated and visible light-activated photoinitiators have tradenames such as IRGACURE 651, IRGACURE 184, IRGACURE 369, IRGACURE 819, DAROCUR 4265 and DAROCUR 1173 commercially available from Ciba Specialty Chemicals, Tarrytown, N.Y. and LUCIRIN TPO and LUCIRIN TPO-L commercially available from BASF (Charlotte, N.C.)

A photosensitizer may also be included in a suitable initiator system. Representative photosensitizers have carbonyl groups or tertiary amino groups or mixtures thereof. Photosensitizers having a carbonyl groups include benzophenone, acetophenone, benzil, benzaldehyde, o-chlorobenzaldehyde, xanthone, thioxanthone, 9,10-anthraquinone, and other aromatic ketones. Photosensitizers having tertiary amines include methyldiethanolamine, ethyldiethanolamine, triethanolamine, phenylmethyl-ethanolamine, and dimethylaminoethylbenzoate. Commercially available photosensitizers include QUANTICURE ITX, QUANTICURE QTX, QUANTICURE PTX, QUANTICURE EPD from Biddle Sawyer Corp.

In general, the amount of photosensitizer or photoinitiator system may vary from about 0.01 to 10% by weight.

Examples of cationic initiators include salts of onium cations, such as arylsulfonium salts, as well as organometallic salts such as ion arene systems.

In various embodiments where the monomers are diluted in solvent before being deposited on the substrate surface, the solvent is removed prior to polymerizing. The solvent may be removed by any suitable mechanism or process. In general about 80% or more, about 90% or more, about 95% or more, or about 99% or more of the solvent may be removed prior to polymerization. As described in copending application Ser. No. 12/362,782, filed on even date herewith, naming Zhou et al. as inventors, and entitled CELL CULTURE ARTICLE AND SCREENING, it has been found that removal of substantially all of the solvent prior to curing, allows for better control of curing kinetics and the amount of monomer converted. When conversion rates of the monomers are increased, waste generation and cytotoxicity are reduced.

To form the synthetic swellable (meth)acrylate surface, the monomers are polymerized. Whether polymerized in bulk phase (substantially solvent free) or solvent phase, the monomers are polymerized via an appropriate initiation mechanism. Many of such mechanisms are well known in the art. For example, temperature may be increased to activate a thermal initiator, photoinitiators may be activated by exposure to appropriate wavelength of light, or the like. According to numerous embodiments, the monomer or monomer mixture is cured using UV light. The curing preferably occurs under inert gas protection, such as nitrogen protection, to prevent oxygen inhibition. Suitable UV light combined with gas protection may increase polymer conversion, insure coating integrity and reduce cytotoxicity.

The cured synthetic swellable (meth)acrylate layer may be washed with solvent one or more times to remove impurities such as unreacted monomers or low molecular weight polymer species. In various embodiments, the layer is washed with ethanol or an ethanol-water solution, e.g. 70% ethanol, greater than 90% ethanol, greater than 95% ethanol or greater than about 99% ethanol. Washing with a 70% ethanol solvent may not only serve to remove impurities, which may be cytotoxic, but also can serve to sterilize the surface prior to incubation with cells.

Swellable (meth)acrylate layers produced in accordance with the teachings herein form a single polymeric matrix layer. While such layers may include local variations in structure and properties, the variations tend to be random, as opposed to interpenetrating networks described by others. As discussed above, in many embodiments, a swellable (meth) acrylate layer as described herein is polymerized from monomers in situ while in contact with the substrate of the cell culture article.

A polypeptide may be conjugated to the polymerized swellable (meth)acrylate layer via any suitable technique. A polypeptide may be conjugated to a polymerized swellable (meth)acrylate layer 20 via an amino terminal amino acid, a carboxy terminal amino acid, or an internal amino acid. One suitable technique involves 1-ethyl-3-[3-dimethylaminopropyl]carbodiimide hydrochloride (EDC)/N-hydroxysuccinimide (NHS) chemistry, as generally known in the art. EDC and NHS or N-hydroxysulfosuccinimide (sulfo-NHS) can react with carboxyl groups of the swellable (meth)acrylate layer to produce amine reactive NHS esters. EDC reacts with a carboxyl group of the swellable (meth)acrylate layer to produce an amine-reactive O-acylisourea intermediate that is susceptible to hydrolysis. The addition of NHS or sulfo-NHS stabilizes the amine-reactive O-acylisourea intermediate by converting it to an amine reactive NHS or sulfo-NHS ester, allowing for a two step procedure. Following activation of the swellable (meth)acrylate layer, the polypeptide may then be added and the terminal amine of the polypeptide can react with the amine reactive ester to form a stable amide bond, thus conjugating the polypeptide to the swellable (meth)acrylate layer. When EDC/NHS chemistry is employed to conjugate a polypeptide to the swellable (meth)acrylate layer, the N-terminal amino acid is preferably an amine containing amino acid such as lysine, ornithine, diaminobutyric acid, or diaminoproprionic acid. Of course, any acceptable nucleophile may be employed, such as hydroxylamines, hydrazines, hydroxyls, and the like.

EDC/NHS chemistry results in a zero length crosslinking of polypeptide 70 to swellable (meth)acrylate layer 20. Linkers or spacers, such as poly(ethylene glycol) linkers (e.g., available from Quanta BioDesign, Ltd.) with a terminal amine may be added to the N-terminal amino acid of polypeptide 70. When adding a linker to the N-terminal amino acid, the linker is preferably a N-PG-amido-PEG$_x$-acid where PG is a protecting group such as the Fmoc group, the BOC group, the CBZ group or any other group amenable to peptide synthesis and X is 2, 4, 6, 8, 12, 24 or any other discrete PEG which may be available.

In various embodiments, a 1 µM-2500 µM polypeptide fluid composition, such as a solution, suspension, or the like, is contacted with an activated swellable (meth)acrylate layer to conjugate the polypeptide. For example the polypeptide concentration may be between about 100 µM and about 2000 µM, between about 500 µM and about 1500 µM, or about 1000 µM. It will be understood that the volume of the polypeptide composition and the concentration may be varied to achieve a desired density of polypeptide conjugated to the swellable (meth)acrylate layer.

The polypeptide may be cyclized or include a cyclic portion. Any suitable method for forming cyclic polypeptide may be employed. For example and with reference to Example 4 below, an amide linkage created by cyclizing the free amino functionality on an appropriate amino-acid side chain and a free carboxyl group of an appropriate amino acid side chain. Also with reference to Example 4 below, a di-sulfide linkage may be created between free sulfydryl groups of side chains appropriate amino acids in the peptide sequence. Any suitable technique may be employed to form cyclic polypeptides (or portions thereof). By way of example, methods described in, e.g., WO1989005150 may be employed to form cyclic polypeptides. Head-to-tail cyclic polypeptides, where the polypeptides have an amide bond between the carboxy terminus and the amino terminus may be employed. An alternative to the disulfide bond would be a diselenide bond using two selenocysteines or mixed selenide/sulfide bond, e.g., as described in Koide et al, 1993, Chem. Pharm. Bull. 41(3): 502-6; Koide et al., 1993, Chem. Pharm. Bull. 41(9):1596-1600; or Besse and Moroder, 1997, Journal of Peptide Science, vol. 3, 442-453.

3. Incubating Cells on Synthetic Swellable (meth)acrylate Layer Containing Conjugated Polypeptide A cell culture article having a swellable (meth)acrylate layer with conjugated polypeptide as described above may be seeded with cells. The cells may be of any cell type. For example, the cells may be connective tissue cells, epithelial cells, endothelial cells, hepatocytes, skeletal or smooth muscle cells, heart muscle cells, intestinal cells, kidney cells, or cells from other organs, stem cells, islet cells, blood vessel cells, lymphocytes, cancer cells, primary cells, cell lines, or the like. The cells may be mammalian cells, preferably human cells, but may also be non-mammalian cells such as bacterial, yeast, or plant cells.

In numerous embodiments, the cells are stem cells which, as generally understood in the art, refer to cells that have the ability to continuously divide (self-renewal) and that are capable of differentiating into a diverse range of specialized cells. In some embodiments, the stem cells are multipotent, totipotent, or pluripotent stem cells that may be isolated from an organ or tissue of a subject. Such cells are capable of giving rise to a fully differentiated or mature cell types. A stem cell may be a bone marrow-derived stem cell, autologous or otherwise, a neuronal stem cell, or an embryonic stem cell. A stem cell may be nestin positive. A stem cell may be a hematopoeietic stem cell. A stem cell may be a multi-lineage cell derived from epithelial and adipose tissues, umbilical cord blood, liver, brain or other organ. In various embodiments, the stem cells are pluripotent stem cells, such as pluripotent embryonic stem cells isolated from a mammal. Suitable mammals may include rodents such as mice or rats, primates including human and non-human primates. In various embodiments, the swellable (meth)acrylate-polypeptide layer supports undifferentiated culture of embryonic stem cells for 5 or more passages, 7 or more passages, or 10 or more passages. Typically stems cells are passaged to a new surface after they reach about 75% confluency. The time for cells to reach 75% confluency is dependent on media, seeding density and other factors as know to those in the art. It has been found that stem cells cultured as described in the Examples below reach about 75% confluency is between about 3 days and about 7 days, generally being about 5 days.

Because human embryonic stem cells (hESC) have the ability to grown continually in culture in an undifferentiated state, the hESC for use in this invention may be obtained from an established cell line. Examples of human embryonic stem cell lines that have been established include, but are not limited to, H1, H7, H9, H13 or H14 (available from WiCell established by the University of Wisconsin) (Thompson (1998) Science 282:1145); hESBGN-01, hESBGN-02, hES-BGN-03 (BresaGen, Inc., Athens, Ga.); HES-1, HES-2, HES-3, HES-4, HES-5, HES-6 (from ES Cell International, Inc., Singapore); HSF-1, HSF-6 (from University of California at San Francisco); I 3, I 3.2, I 3.3, I 4, I 6, I 6.2, J 3, J 3.2 (derived at the Technion-Israel Institute of Technology, Haifa, Israel); UCSF-1 and UCSF-2 (Genbacev et al., Fertil. Steril. 83(5):1517-29, 2005); lines HUES 1-17 (Cowan et al., NEJM 350(13):1353-56, 2004); and line ACT-14 (Klimanskaya et al., Lancet, 365(9471):1636-41, 2005). Embryonic stem cells used in the invention may also be obtained directly from primary embryonic tissue. Typically this is done using frozen in vitro fertilized eggs at the blastocyst stage, which would otherwise be discarded.

Other sources of pluripotent stem cells include induced primate pluripotent stem (iPS) cells. iPS cells refer to cells, obtained from a juvenile or adult mammal, such as a human, that are genetically modified, e.g., by transfection with one or more appropriate vectors, such that they are reprogrammed to attain the phenotype of a pluripotent stem cell such as an hESC. Phenotypic traits attained by these reprogrammed cells include morphology resembling stem cells isolated from a blastocyst as well as surface antigen expression, gene expression and telomerase activity resembling blastocyst derived embryonic stem cells. The iPS cells typically have the ability to differentiate into at least one cell type from each of the primary germ layers: ectoderm, endoderm and mesoderm.

The iPS cells, like hESC, also form teratomas when injected into immuno-deficient mice, e.g., SCID mice. (Takahashi et al., (2007) Cell 131(5):861; Yu et al., (2007) Science 318: 5858).

Prior to seeding cells, the cells may be harvested and suspended in a suitable medium, such as a growth medium in which the cells are to be cultured once seeded onto the surface. For example, the cells may be suspended in and cultured in a serum-containing medium, a conditioned medium, or a chemically-defined medium. As used herein, "chemically-defined medium" means cell culture media that contains no components of unknown composition. Chemically defined cell culture media may, in various embodiments, contain no proteins, hydrosylates, or peptides of unknown composition. In some embodiments, conditioned media contains polypeptides or proteins of known composition, such as recombinant growth hormones. Because all components of chemically-defined media have a known chemical structure, variability in culture conditions and thus variability in cell response can be reduced, increasing reproducibility. In addition, the possibility of contamination is reduced. Further, the ability to scale up is made easier due, at least in part, to the factors discussed above. Chemically defined cell culture media are commercially available from Invitrogen (Invitrogen Corporation, 1600 Faraday Avenue, PO Box 6482, Carlsbad, Calif. 92008) as STEM PRO, a fully serum- and feeder-free (SFM) specially formulated from the growth and expansion of embryonic stem cells, Xvivo (Lonza), and Stem Cell Technologies, Inc. as mTeSR™1 maintenance media for human embryonic stem cells.

One or more growth or other factors may be added to the medium in which cells are incubated with the synthetic swellable (meth)acrylate layer conjugated to polypeptide (SAP). The factors may facilitate cellular proliferation, adhesion, self-renewal, differentiation, or the like. Examples of factors that may be added to or included in the medium include muscle morphogenic factor (MMP), vascular endothelium growth factor (VEGF), interleukins, nerve growth factor (NGF), erythropoietin, platelet derived growth factor (PDGF), epidermal growth factor (EGF), activin A (ACT) such as activin A, hematopoietic growth factors, retinoic acid (RA), interferons, fibroblastic growth factors, such as basic fibroblast growth factor (bFGF), bone morphogenetic protein (BMP), peptide growth factors, heparin binding growth factor (HBGF), hepatocyte growth factor, tumor necrosis factors, insulin-like growth factors (IGF) I and II, transforming growth factors, such as transforming growth factor-β1 (TGFβ1), and colony stimulating factors.

The cells may be seeded at any suitable concentration. Typically, the cells are seeded at about 10,000 cells/cm$^2$ of substrate to about 500,000 cells/cm$^2$. For example, cells may be seeded at about 50,000 cells/cm$^2$ of substrate to about 150,000 cells/cm$^2$. However, higher and lower concentrations may readily be used. The incubation time and conditions, such as temperature, $CO_2$ and $O_2$ levels, growth medium, and the like, will depend on the nature of the cells being cultured and can be readily modified. The amount of time that the cells are incubated on the surface may vary depending on the cell response desired.

The cultured cells may be used for any suitable purpose, including (i) obtaining sufficient amounts of undifferentiated stem cells cultured on a synthetic surface in a chemically defined medium for use in investigational studies or for developing therapeutic uses, (ii) for investigational studies of the cells in culture, (iii) for developing therapeutic uses, (iv) for therapeutic purposes, (v) for studying gene expression, e.g. by creating cDNA libraries, and (vi) for studying drug and toxicity screening.

As described in more detail in the Examples below, it has been found that the undifferentiated state of stem cells, such as embryonic stem cells, can be maintained for 5, 7, or 10 or more passages on articles having an SA-P substrate. In various embodiments, 50% or more, 60% or more, 70% or more, or 80% or more of the cells remain undifferentiated after each passage. One suitable way to determine whether cells are undifferentiated is to determine the presence of the OCT4 marker, e.g. as described in more detail below in the Examples. In various embodiments, the undifferentiated stems cells culture on SA-P surfaces for 5, 7, or 10 or more passages retain the ability to be differentiated.

In the following, non-limiting examples are presented, which describe various embodiments of the articles and methods discussed above.

EXAMPLES

Example 1

Coating Preparation

Swellable (meth)acrylate coating surfaces were prepared from UV polymerizable monomers and include a hydrophilic monomer, a carboxyl group containing monomer, and a crosslinking monomer. Table 1 shows the combination of swellable (meth)acrylate monomers employed. As shown in Table 1, formulations SA1A and SA1 have the same monomer composition. They differ from each other in that SA1A is diluted in ethanol in a 0.1% concentration v/v while SA1 is diluted in ethanol in a 0.25% v/v concentration or higher. The dilutions of monomers diluted in ethanol are shown in Table 3. Table 2 shows the chemical structures of the monomers used.

TABLE 1

Swellable (meth)acrylate formulations employed

| Formulation No. | Hydrophilic Monomer (vol. %) | Carboxyl group containing monomer (vol. %) | Crosslinking monomer (vol. %) |
|---|---|---|---|
| SA1A or SA1 | hydroxyethyl methacrylate (80) | 2-carboxyethyl acrylate (20) | Tetra(ethylene glycol) dimethacrylate (3) |
| SA3 | hydroxyethyl methacrylate (60) | 2-carboxyethyl acrylate (40) | Tetra(ethylene glycol) dimethacrylate (3) |
| SA5 | poly(ethylene glycol)(600) dimethacrylate (80) | 2-carboxyethyl acrylate (20) | |
| SA11 | hydroxyethyl methacrylate (90) | 2-carboxyethyl acrylate (10) | Tetra(ethylene glycol) dimethacrylate (3) |
| SA12 | hydroxyethyl methacrylate (70) | 2-carboxyethyl acrylate (30) | Tetra(ethylene glycol) dimethacrylate (3) |
| SA13 | Hydroxypropyl methacrylate(80) | 2-carboxyethyl acrylate (20) | Tetra(ethylene glycol) dimethacrylate (3) |
| SA14 | 2-Hydroxyethyl acrylate(80) | 2-carboxyethyl acrylate (20) | Tetra(ethylene glycol) dimethacrylate (3) |
| SA15 | 1-vinyl-2-pyrrolidone(80) | 2-carboxyethyl acrylate (20) | Tetra(ethylene glycol) dimethacrylate (3) |
| SA16 | Hydroxyethyl methacrylate (80) | 2-Carboxyethyl acrylate (20) | Tetra(ethylene glycol) dimethacrylate (1) |
| SA17 | Hydroxyethyl methacrylate (80) | 2-Carboxyethyl acrylate (20) | Tetra(ethylene glycol) dimethacrylate. (10) |
| SA18 | Di(ethylene glycol) ethyl ether methacrylate(80) | 2-carboxyethyl acrylate (20) | Tetra(ethylene glycol) dimethacrylate (3) |
| SA19 | Acrylamide(80) | 2-carboxyethyl acrylate (20) | Tetra(ethylene glycol) dimethacrylate (3) |
| SA20 | Ethylene glycol methyl ether methacrylate(80) | 2-carboxyethyl acrylate (20) | Tetra(ethylene glycol) dimethacrylate (3) |
| SA21 | 3-sulfopropyldimethyl-3-methacrylamidopropyl-ammonium(80) | 2-carboxyethyl acrylate (20) | Tetra(ethylene glycol) dimethacrylate (3) |
| SA22 | Di(ethylene glycol) ethyl ether methacrylate(40) Hydroxyethyl methacrylate(40) | 2-Carboxyethyl acrylate (20) | Tetra(ethylene glycol) dimethacrylate. (3) |
| SA23 | Acrylamide (40) Hydroxyethyl methacrylate(40) | 2-Carboxyethyl acrylate (20) | Tetra(ethylene glycol) dimethacrylate. (3) |
| SA24 | Ethylene glycol methyl ether methacrylate (40) 2-Hydroxyethyl methacrylate (40) | 2-Carboxyethyl acrylate (20) | Tetra(ethylene glycol) dimethacrylate. (3) |

TABLE 1-continued

Swellable (meth)acrylate formulations employed

| Formulation No. | Hydrophilic Monomer (vol. %) | Carboxyl group containing monomer (vol. %) | Crosslinking monomer (vol. %) |
|---|---|---|---|
| SA25 | 3-sulfopropyldimethyl-3-methacrylamidopropyl-ammonium inner salt (40) Hydroxyethyl methacrylate (40) | 2-Carboxyethyl acrylate (20) | Tetra(ethylene glycol) dimethacrylate. (3) |

TABLE 2

Structures of Monomers 2-hydroxyethyl methacrylate

2-Carboxyethyl acrylate

Tetra(ethylene glycol) dimethacrylate

Tetra(ethylene glycol) diacrylate poly(ethylene glycol)(600) dimethacrylate

Hydroxypropyl methacrylate

2-Hydroxyethyl acrylate 1-vinyl-2-pyrrolidone

Di(ethylene glycol) ethyl ether methacrylate

TABLE 2-continued

Structures of Monomers

Acrylamide

Ethylene glycol methyl ether methacrylate 3-sulfopropyldimethyl-3-methacrylamidopropyl-ammonium Isobutyl acrylate Briefly, the monomers were diluted in ethanol to the concentration of (0.1%) or 0.25% by volume, and Durocur 1173 (3% volume/monomer volume) photoinitiator was added. The diluted monomer swellable (meth)acrylate formulations were added to a well of a plasma treated cyclic olefin copolymer 96 well plate (provided by Corning Life Science Development group) at a volume of 2 μL using BioTek Precision Pipetting System.

Each well received a predetermined swellable (meth)acrylate monomer formulation, with some wells being coated with MATRIGEL™ as a positive control. The coatings were applied to result in an average thickness of 0.5 micrometers or less. Unless stated otherwise, the resulting swellable (meth)acrylate coatings had an average thickness of about 0.1 micrometers. For the wells coated with swellable (meth)acrylate monomer formulations, the ethanol solvent was removed by evaporation at room temperature for 3 hours in a fume hood. The coatings were then cured with 13 mW/cm² pulsed (100 Hz) UV light (Xenon RC-801) for 1 min in $N_2$ purged box (with fused silica window).

For a number of the swellable (meth)acrylate formulations, a well of a 96-well plate was coated with 5 microliters of 0.1 v/v % ethanol solution of acrylic monomers or 2 microliters of 0.25 v/v % ethanol solution of acrylic monomers, resulting in 5 nanoliters of monomers per well (0.3165 cm²) and a coating thickness of 0.13-0.20 micrometers. The various formulations and concentrations and volumes employed are listed in Table 3 below.

TABLE 3

Swellable (meth)acrylate formulations and concentrations/volumes applied

| Formulation No. | 0.1% at 5 microliters | 0.25% at 2 microliters |
|---|---|---|
| SA1A | X | |
| SA1 | | X |
| SA3 | | X |
| SA5 | | X |
| SA11 | | X |
| SA12 | | X |

TABLE 3-continued

Swellable (meth)acrylate formulations and concentrations/volumes applied

| Formulation No. | 0.1% at 5 microliters | 0.25% at 2 microliters |
|---|---|---|
| SA13 | | X |
| SA14 | | X |
| SA15 | | X |
| SA16 | | X |
| SA17 | | X |
| SA18 | | X |
| SA19 | | X |
| SA20 | | X |
| SA21 | | X |
| SA22 | | X |
| SA23 | | X |
| SA24 | | X |
| SA25 | | X |

Example 2

Polypeptide Conjugation to Swellable (meth)acrylate Surface

In a series of experiments designed to evaluate polypeptide conjugation to the swellable (meth)acrylate coatings prepared as described above, a mixture of polypeptides (Ac-ArgGlyGlySerAspProIleTyrLys-NH₂ (SEQ ID NO:27)/Rhod-GlyArgGlyAspSerProIleIleLys-NH₂(SEQ ID NO:28)) was conjugated to a swellable (meth)acrylate coating of Formulation SA1A (see Tables 1, 2 and 3) comprising 1-ethyl-3-[3-dimethylaminopropyl]carbodiimide hydrochloride (EDC)/ N-hydroxysuccinimide (NHS) chemistry. Briefly, 50 μL of 0.1 mM EDC and 0.05 mM NHS solution in DMF were dispensed into a well of 96-well cyclic olefin copolymer plate coated with swellable (meth)acrylate formulation. The activation of carboxyl groups was allowed to proceed for 1-1.5 h, and then the activating solution was aspirated. Immediately after that, 50 μL of polypeptide solution in 25 mM phosphate buffer pH 7.4 were dispensed into the well and the reaction between well surface NHS esters and peptide primary amine groups was carried out at ambient condition for 1.5h and then the peptide solution was aspirated. Immediately after that, 50 μL of 1M ethanolamine, pH 8.0-8.5 in water were dispensed into the well and the blocking reaction was carried out at ambient condition for 1.5 h. Then, the blocking solution was aspirated and the well was washed with phosphate buffer, 1% SDS solution, and finally deionized water. Fluorescence was quantified using a Tecan microarray scanner. Alternatively, the polypeptides were quantified with the QuantiPro BCA assay kit available from Sigma-Aldrich. The peptide solution contained 1000 μM, 100 μM, 50 μM, 10 μM, 5 μM, 1 μM, or 0 μM total peptide.

TABLE 4

Peptides conjugated to swellable (meth)acrylate surfaces and tested in hESC culture

| Peptide ID | | Peptide sequence |
|---|---|---|
| (SEQ ID NO:1) | RGD | Yaa$_l$Xaa$_n$ArgGlyAspXaa$_m$Yaa$_l$ |
| (SEQ ID NO:2) | cyclic | ZaaXaa$_n$ArgGlyAspXaa$_m$Baa |
| (SEQ ID NO:3) | (cyclic with conjugation sites) | Yaa$_l$Xaa$_m$ZaaXaa$_n$ArgGlyAspXaa$_m$Baa Xaa$_m$Yaa$_l$ |
| (SEQ ID NO:4) | BSP (mouse) | LysGlyGlyAsnGlyGluProArgGlyAspThrTyr ArgAlaTyr |
| (SEQ ID NO:5) | BSP (mouse) | AsnGlyGluProArgGlyAspThrTyrArgAlaTyr |
| (SEQ ID NO:6) | cyclic BSP | LysGlyGlyLys$^4$AsnGlyGluProArgGlyAsp ThrTyrArgAlaTyrAsp$^{17}$, Lys$^4$-Asp$^{17}$ amide cycle |
| (SEQ ID NO:7) | cyclic BSP | LysGlyGlyLys$^4$GluProArgGlyAspThrTyrArgAsp$^{13}$, Lys$^4$-Asp$^{13}$ amide cycle |
| (SEQ ID NO:8) | cyclic BSP | LysGlyGlyCys$^4$AsnGlyGluProArgGlyAspThrTyrArg AlaTyrCys$^{17}$, Cys$^4$-Cys$^{17}$ disulfide bonded cycle |
| (SEQ ID NO:9) | cyclic BSP | LysGlyGlyCys$^4$GluProArgGlyAspThrTyrArg Cys$^{13}$ Cys$^4$-Cys$^{13}$ disulfide bonded cycle |
| (SEQ ID NO:10) | BSP (mouse) | XaaGlyGlyAsnGlyGluProArgGlyAspThrTyr ArgAlaTyr |
| (SEQ ID NO:11) | short FN (s-FN) (human) | GlyArgGlyAspSerProLys |
| (SEQ ID NO:12) | Long FN (l-FN) (human) | LysGlyGlyAlaValThrGlyArgGlyAspSerProAla SerSer |
| (SEQ ID NO:13) | CYR61 (mouse laminin) | LysGlyGlyGlyGlnLysCysIleValGlnThrThrSerTrpSer GlnCysSerLysSer |
| (SEQ ID NO:14) | Human thrombospondin 1 | LysTyrGlyLeuAlaLeuGluArgLysAspHisSerGly |
| (SEQ ID NO:15) | SN (mouse laminin) | LysGlyGlySerIleAsnAsnAsnArgTrpHisSerIleTyrIleThr ArgPheGlyAsnMetGlySer |
| (SEQ ID NO:16) | AG32 (mouse laminin) | LysGlyGlyThrTrpTyrLysIleAlaPheGlnArgAsnArgLys |
| (SEQ ID NO:17) | C68 (mouse laminin) | LysGlyGlyThrSerIleLysIleArgGlyThrTyrSerGluArg |
| (SEQ ID NO:18) | C28 (mouse laminin) | LysTyrGlyThrAspIleArgValThrLeuAsnArgLeuAsnThrPhe |
| (SEQ ID NO:19) | C64 (mouse laminin) | LysTyrGlySerGluThrThrValLysTyrIlePheArgLeuHisGlu |
| (SEQ ID NO:20) | A208 (IKVAV) (mouse laminin) | LysTyrGlyAlaAlaSerIleLysValAlaValSerAlaAspArg |
| (SEQ ID NO:21) | C16 (mouse laminin) | LysTyrGlyLysAlaPheAspIleThrTyrValArgLeuLysPhe |
| (SEQ ID NO:22) | AG73 with LysTyrGly linker | LysTyrGlyArgLysArgLeuGlnValGlnLeuSerIleArgThr |

TABLE 4-continued

Peptides conjugated to swellable (meth)acrylate surfaces and tested in hESC culture

| Peptide ID | | Peptide sequence |
|---|---|---|
| (SEQ ID NO:23) | RNIA with linker | LysGlyGlyArgAsnIleAlaGluIleIleLysAspIle |
| (SEQ ID NO:24) | AG-73 | ArgLysArgLeuGlnValGlnLeuSerIleArgThr |
| (SEQ ID NO:25) | RNIA peptide | ArgAsnIleAlaGluIleIleLysAspIle |
| (SEQ ID NO:26) | C16 (mouse laminin) | LysAlaPheAspIleThrTyrValArgLeuLysPhe |
| (SEQ ID NO:27) | Synthetic peptide (scrambled RGD) | ArgGlyGlySerAspProIleTyrLys |
| (SEQ ID NO:28) | Labeled RGD | GlyArgGlyAspSerProIleIleLys |
| (SEQ ID NO:29) | VN (human) | LysGlyGlyProGlnValThrArgGlyAspValPheThrMetPro |
| (SEQ ID NO:30) | RGE | GlyArgGlyGluSerProIleTyrLys |
| (SEQ ID NO:31) | BSP (modified) | LysGlyGlyAsnGlyGluProArgGlyAspThrArgAlaTyr |

Many of these sequences have a Lys-Gly-Gly (KGG) amino acid sequence at the N-terminus. The Lys amino acid has a side chain containing an amino group and is used for conjugating the peptide to the activated (meth)acrylate coating. The Gly-Gly amino acids were used to serve as a spacer designed to project the putative RGD epitope away from the coated surface to enable optimal bio-specific interaction of the peptide with the cell surface receptors. It is conceivable that the linker sequence is not required or a shorter sequence can be used. Alternatively or in addition, non-amino acid based linkers (such as poly ethylene oxide linkers or the like) may be used as spacers (see, for example, FIG. 6). It will be understood that this sequence may be present or absent in embodiments of the peptide sequences of the present invention.

Figure 3:
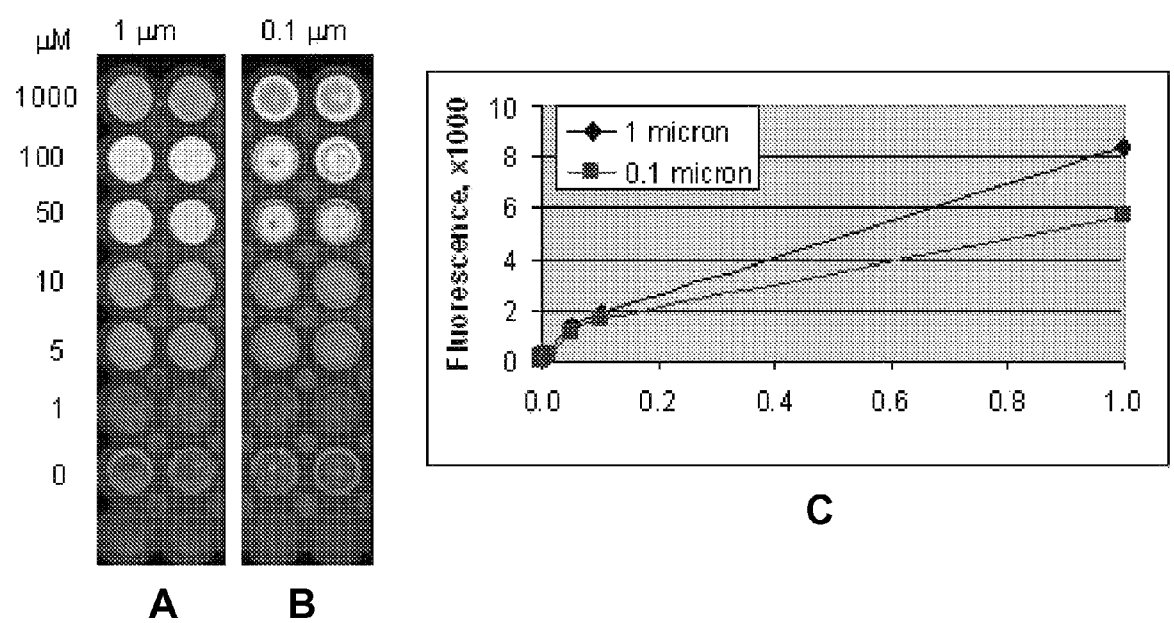
FIG. 3A is an image of fluorescence intensity of polypeptide conjugated to 1 micrometer thick layers of swellable (meth)acrylate coating in a multi-well plate.
FIG. 3B is an image of fluorescence intensity of polypeptide conjugated to 0.1 micrometer thick layers of swellable (meth)acrylate coating in a multi-well plate.
FIG. 3C is a graph of polypeptide concentration vs. fluorescence intensity for polypeptides coated on 1 micrometer or 0.1 micrometer thick surfaces.

FIG. 3 shows fluorescence data regarding the ability of a mixture of peptides (Ac-ArgGlyGlySerAspProIleTyrLys-NH$_2$ (SEQ ID NO:27)/Rhod-GlyArgGlyAspSer-ProIleIleLys-NH$_2$ (SEQ ID NO:28)) to conjugate to a swellable (meth)acrylate coating of Formulation SA1A prepared as described above. FIG. 3A is an image of the fluorescence intensity of peptide conjugated to average approximately 1 micrometer thick layers of the swellable (meth) acrylate coating, in increasing concentrations of peptide from 0 to 1000 μM. FIG. 3B is an image of the fluorescence intensity of peptide conjugated to average approximately 0.1 micrometer thick layers of the swellable (meth)acrylate coating in increasing concentrations of peptide from 0 to 1000 μM. FIG. 3C is a graph of peptide concentration (0 to 1 mM) vs. fluorescence intensity for peptides coated on the 1 micrometer or 0.1 micrometer thick surfaces. As shown in FIG. 3, the amount of peptide conjugated to the coating increases with peptide concentration in conjugation buffer. Fluorescence intensities for the swellable (meth)acrylate coatings of two thicknesses, 1 μm and 0.1 μm, to which peptides were conjugated using the same protocol, suggest that peptides are immobilized at the surface of the coating, rather than evenly through the bulk of the swellable (meth) acrylate. If evenly through the bulk of the swellable (meth) acrylate, one would expect an order of magnitude difference in fluorescence intensities for these two coatings.

Figure 4:
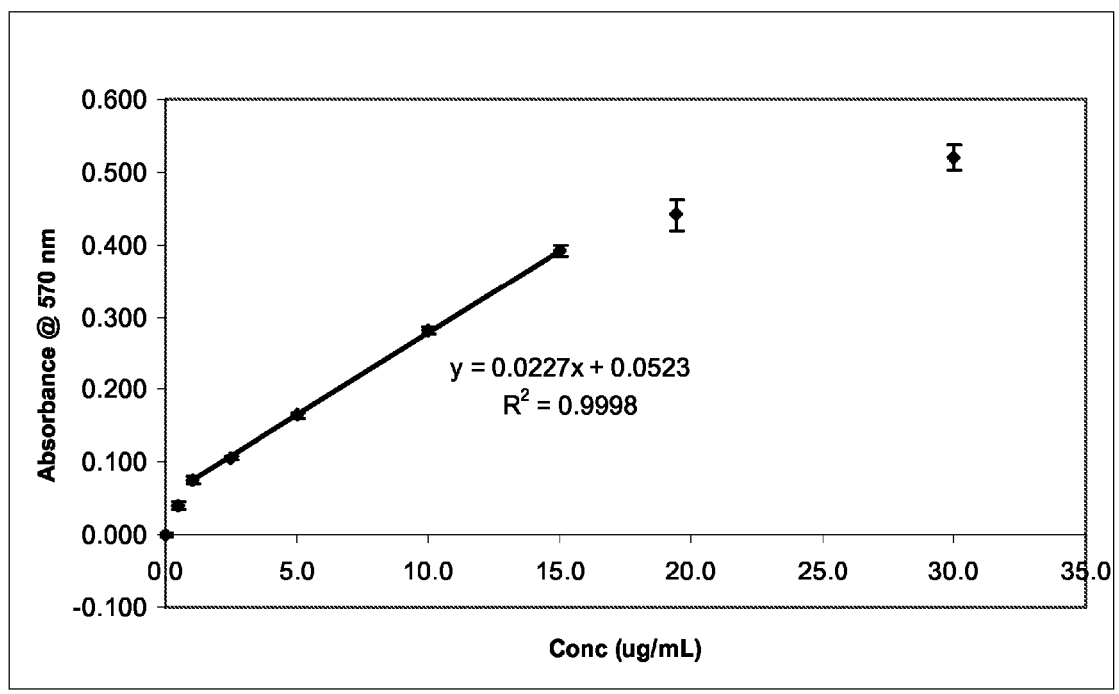
FIG. 4 is a graph of polypeptide concentration vs. absorbance at 570 nm for data obtained from a QuantiPro BCA assay.

FIG. 4 shows the results of the QuantiPro BCA assay described in EXAMPLE 2. Analyzing the peptide conjugated swellable (meth)acrylate resulted in an absorbance at 0.076 AU at 570 nm. Linearity was observed between 1 and 15 μg/ml (as shown by the line in the figure). Although the resulting data was close to the limit of detection (1 μg/mL), the resulting density corresponded well to the density obtained from fluorescence experiments (5.6 pmol/mm$^2$ for BCA and 8.6 pmol/mm$^2$ for fluorescence).

Example 3

HT-1080 Cell Adhesion and Proliferation Assays

To evaluate ability of a polypeptide conjugated to embodiments of swellable (meth)acrylate using these conjugation methods to enable cell adhesion and proliferation, peptides Ac-LysTyrGlyArgLysArgLeuGlnValGlnLeuS erIleArgThr-NH$_2$ (SE Q ID NO:22) (AG-73, an adhesive peptide) and Ac-GlyArgGlyGluSerProIleTyrLys-NH$_2$ (SEQ ID NO:30) (RGE, a negative control) were conjugated to swellable (meth)acrylate (as described above) and adhesion of HT-1080 human fibrosarcoma cells to the swellable (meth)acrylate was evaluated. Briefly, Laminin (5 μg/mL, Sigma-Aldrich) control wells were coated for 1 hour at room temperature. All wells were blocked with 1% bovine serum albumin (BSA) in phosphate buffered saline (PBS) for 1 hour at 37° C. Wells were washed briefly with PBS before incubation with 0.1% BSA in Iscove's Modified Dulbecco's Medium (IMDM) prior to cell seeding. HT-1080 human fibrosarcoma cells (ATCC number: CCL-121) were grown in IMDM (Lonza) with 10% FBS (Lonza) to 90% confluency at standard cell culture conditions. Cells were trypsinized and allowed to recover in IMDM with 10% FBS for 30 minutes at 37° C., 5% CO$_2$. After recovery, cells were washed and resuspended in 0.1% BSA in IMDM and seeded on peptide-conjugated plates at a density of 30,000 cells/well. Cell adhesion was allowed to take place for 1 hour at standard cell culture conditions. The media was aspirated from the wells and adherent cells were fixed and stained in 50 μL of 0.2% crystal violet in 20% methanol for 8 minutes at room temperature. Cellular absorption of crystal violet was quantified through addition of 1% SDS in $H_2O$ for 5 minutes prior to absorbance measurement at 570 nm. For this assay, after polypeptide conjugation the remaining NHS esters on the swellable (meth)acrylate were reacted with ethanolamine or aminopropyl morpholine to reduce uptake of crystal violet dye by the swellable (meth) acrylate.

Figure 5:
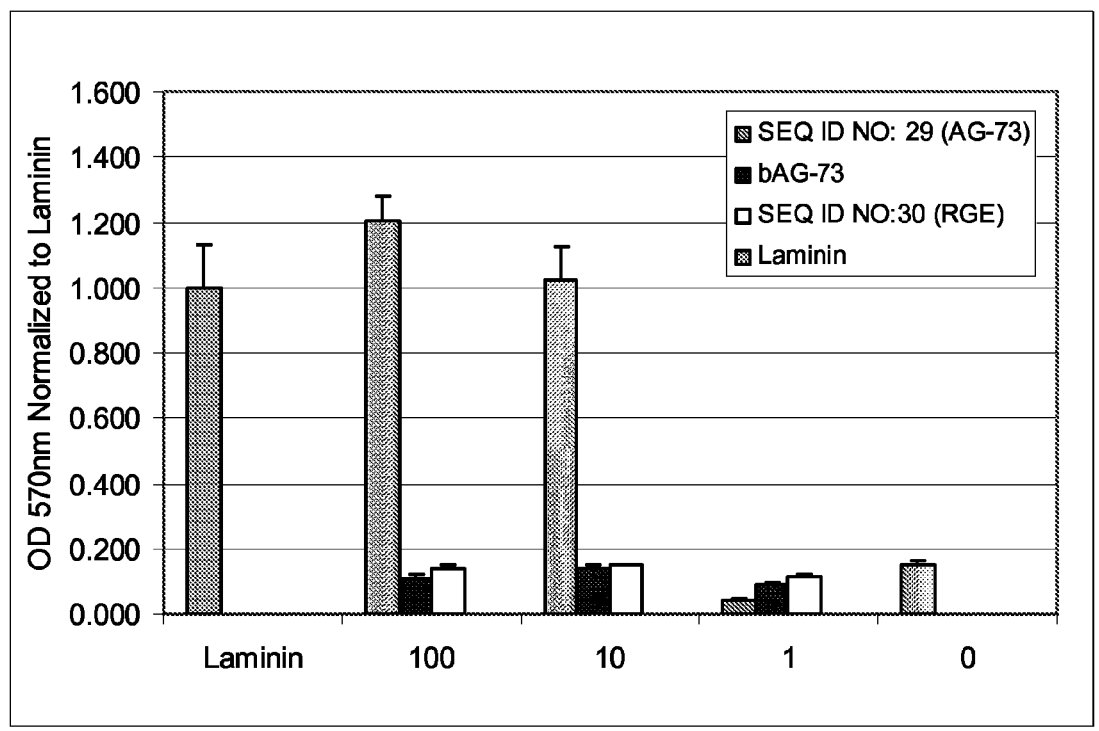
FIG. 5 is a graph of polypeptide concentration vs. absorbance at 570 nm normalized to laminin, showing a results from an assay designed to determine the adherence of HT-1080 cells to various substrates.

FIG. 5 shows the results from the HT-1080 adhesion assay, showing adhesion of HT-1080 cells to embodiments of SAP surfaces of the present invention, as described in Example 3. The relative number of adherent cells on swellable(meth) acrylate-peptide surfaces was normalized to that of cells on Laminin (via OD570 nm). The peptides were tested at 100 μm AG-73 (SEQ ID NO:24), 10, 1 and 0 μM concentrations. OD570 nm measurements were taken, and the readings were normalized to Laminin adherence. "AG-73" is SAP-AG-73 (SEQ ID NO:24). "bAG-73" is SAP-AG-73 (SEQ ID NO:24) which was blocked with ethanolamine prior to polypeptide conjugation. "RGE" is SAP-RGE (SEQ ID NO:30). RGE is a non-adhesive peptide.

HT-1080 cells adhered specifically to adhesive peptide Ac-LysTyrGlyArgLysArgLeuGlnValGlnLeuSerIleArgThr-$NH_2$ (SEQ ID NO:22) (AG-73) and did not adhere to surfaces (1) that were blocked with ethanolamine prior to peptide conjugation (shown as bAG-73, or blockedAG-73) or (2) where a non-adhesive peptide Ac-GlyArgGlyGluSerProIle-TyrLys-$NH_2$ (SEQ ID NO:30) (RGE) was conjugated. 100 μM peptide solution and 10 μM AG-73 peptide solution resulted in an adhesive surface, while 1 μM AG-73 peptide solution did not result in cell adhesive surface. Very few cells adhered to SAP-bAG-73, indicating that AG-73 does not non-specifically adsorb to the synthetic polymeric surface.

Example 4

Assays for Culture of Undifferentiated Stem Cells

Cell adhesive peptides were selected for use with hESCs as listed in Table 4. This list of polypeptides contains peptides which have been shown to target the two important cellular receptor classes of integrins and heparan sulfate proteoglycans (HSPGs). These peptides also encompass sequences from the various domains and chains of laminin. Also, cell adhesive peptides from other proteins have been included.

To screen the peptides shown in Table 4 for their ability to provide satisfactory cell culture surfaces for adhesive properties toward undifferentiated hESCs, peptides were conjugated to a swellable (meth)acrylate of formulation SA1A (see Tables 1, 2 and 3) using 1000 μM solutions. Peptides were purchased from GenScript Corporation. All peptides were amidated at the C-terminus. To the N-terminus of selected peptides, spacers of repeating units of polyethylene glycol (PEG) were added. For example, $PEO_4$ refers to four repeating units of ethylene glycol and $PEO_{12}$ refers to 12 repeating units of ethylene glycol. The spacers contained a terminal amine. The spacers were added to the polypeptides by Gen-Script Corporation.

Ac-LysGlyGlyAsnGlyGluProArgGl-yAspThrTyrArgAlaTyr-$NH_2$ (SEQ ID NO:4) (the BSP sequence), was conjugated to the swellable (meth)acrylate coating of Formulation SA1, SA1A and SA5 as described above in varying concentrations of peptide (1000 μM, 100 μM, 10 μM, 1 μM, and 0 μM).

All experimental plates were sterilized prior to the cell seeding by spraying with 70% ETOH, drying in a laminar hood, and washing five times with 200 μl Dulbecco's Phosphate Buffered Saline (DPBS). H7 hES cells were seeded on peptide conjugated swellable (meth)acrylate (SAP) surfaces at a density of 35,000 cells/well (96-well plate) in 100 μl of chemically defined medium Xvivo10 (Lonza, Cat #04-743Q) and supplemented with 80 ng/ml basic fibroblast growth factor (bFGF) (R&D systems, Cat #234-FSE/CF) and 0.5 ng/ml transforming growth factor-β1 (TGFβ1) (R&D systems, Cat. #240B). MATRIGEL™ (MG)-coated wells were used as positive control for adhesion of undifferentiated hES cells. Cells were cultured for 48 hrs under standard cell culture conditions (37° C. with 5% $CO_2$) and then were fixed and processed for AttoPhos assay to measure alkaline phosphatase activity, which is a known marker for undifferentiated hES cells, and/or BCIP staining as described below.

Example 5

AttoPhos Screening

AttoPhos screening was performed as follows. Briefly, at the end of incubation time, cells were rinsed with 150 μl of DPBS and fixed with 4% paraformaldehyde for 10 min at room temperature (70 μl/well of 96-well plate). The cells were washed once with 150 μl of DPBS, and treated for 10 min with 100 μl of AttoPhos fluorescent substrate for alkaline phosphatase (Promega) (diluted 1:3 in DPBS) protected from light. AttoPhos fluorescent intensity at 485/535 nm was obtained using Victor 3 microplate reader (Perklin Elmer). AttoPhos fluorescent intensity for experimental surfaces was expressed as % of MATRIGEL™ control.

Example 6

BCIP/NBT Staining (5-Bromo-4-chloro-3-indolyl phosphate (BCIP)/Nitroblue tetrazolium (NBT) staining of hES cells for colony morphology assessment was performed as follows. Briefly, after obtaining AttoPhos fluorescent intensity readings, cells were washed with 150 μl DPBS and processed for BCIP staining to assess cell colony morphology. Seventy μl of BCIP/NBT was added to each well and incubated for 20-30 min. (to achieve desirable color intensity) at room temperature with a mild agitation. At the end of the staining, cells were washed once with 150 μl DPBS and either scanned or analyzed with light microscopy. H7 hES colony morphology on experimental surfaces was compared to the colony morphology on MATRIGEL™ (positive control).

Figure 6:
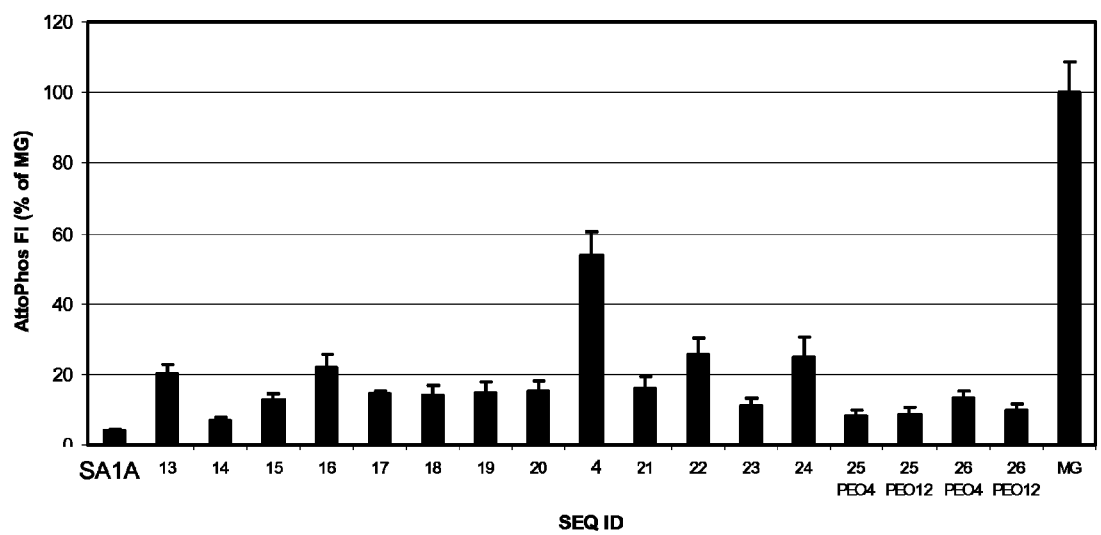
FIG. 6 is a graph illustrating the relative number of undifferentiated hESC (by AttoPhos fluorescence intensity) cultured in a chemically defined medium on swellable (meth) acrylate substrates having particular conjugated polypeptides.
Figure 7:
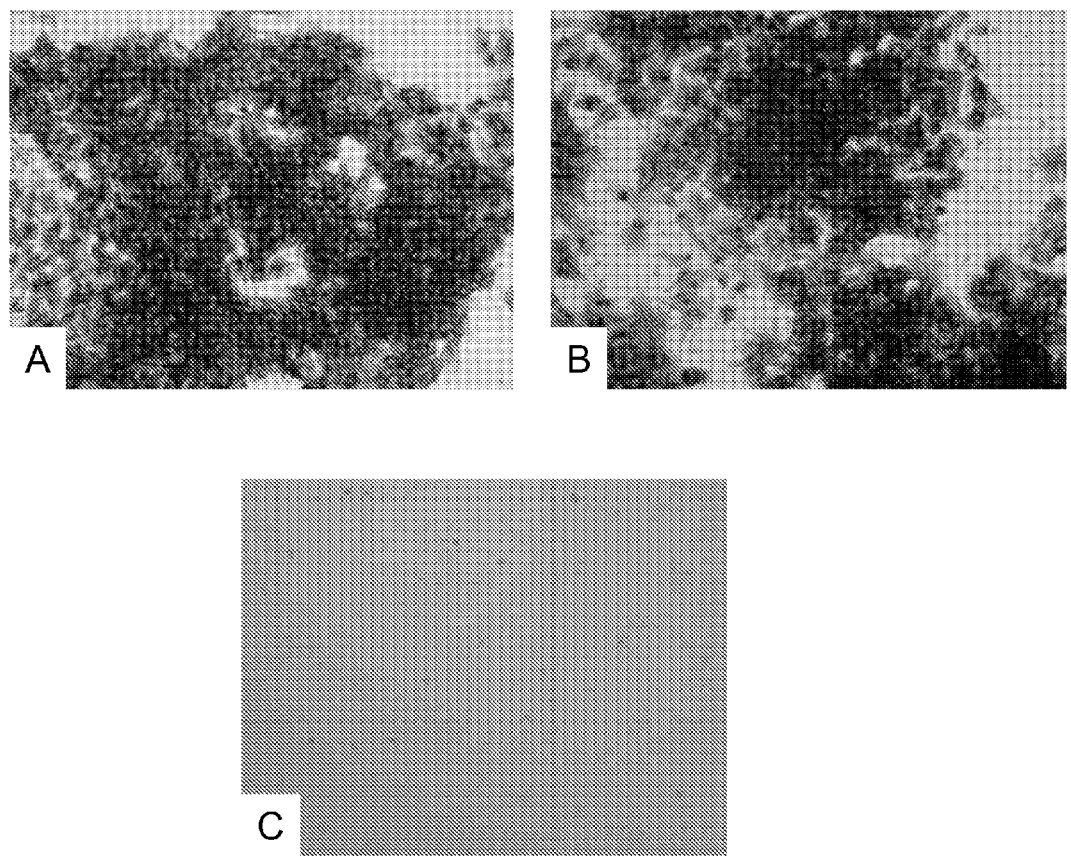
FIGS. 7A-C are images of colonies of undifferentiated human embryonic stem cells cultured in a chemically defined medium on a MATRIGEL™ substrate (A), a swellable (meth)acrylate with conjugated peptide (SEQ ID NO:4) (as identified in FIG. 6) (B), or swellable (meth)acrylate alone (C).
Figure 8:
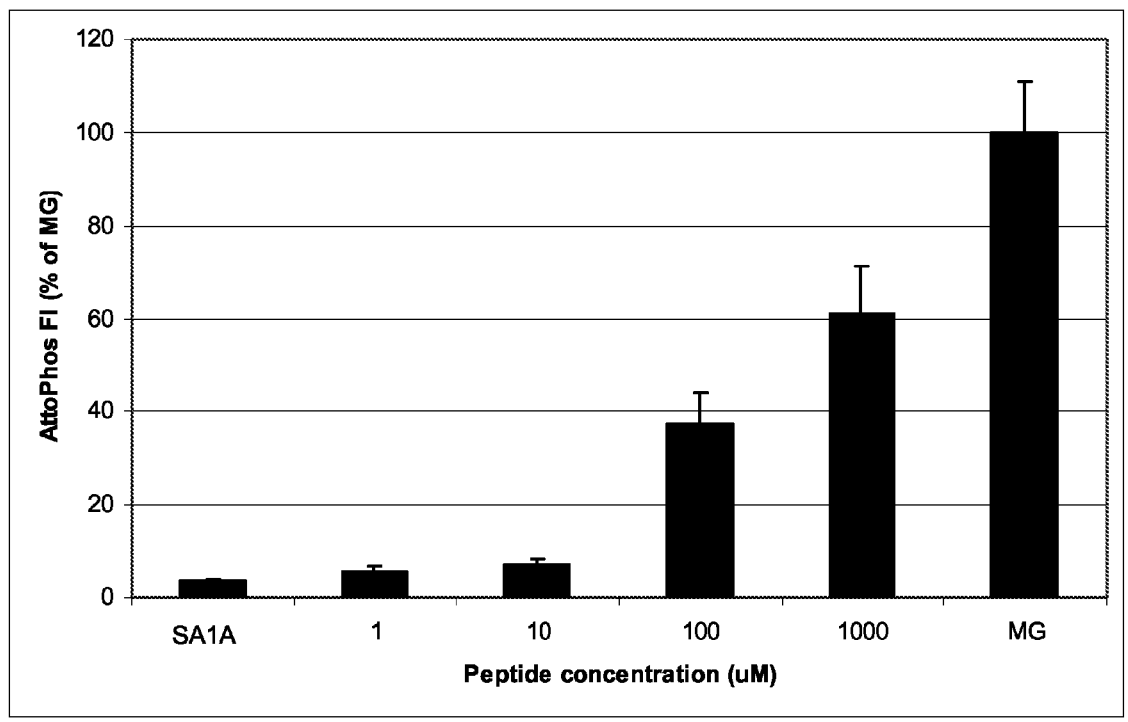
FIG. 8 is a graph illustrating the relative number of undifferentiated human embryonic stem cells (by AttoPhos fluorescence intensity) cultured in a chemically defined medium on a swellable (meth)acrylate conjugated with varying concentrations of peptide (SEQ ID NO:4) (as identified in FIG. 6).

FIG. 6 shows the results from the screening assay for peptide support of undifferentiated stem cells using Formulation SA1A. Ac-KGGNGEPRGDTYRAY-$NH_2$ (SEQ ID NO:4), the BSP sequence demonstrated a significant ability to support undifferentiated stem cells (56-60% AttoPhos fluorescence intensity (FI)) compared to MATRIGEL™ control. Some peptides were conjugated to PEO spacers/linkers (SEQ ID NO:25 and SEQ ID NO:26) as follows: $NH_2PEO_4$-ArgAs-nIleAlaGluIleIleLysAspIle-$NH_2$ (SEQ ID NO:25) or $NH_2$-$PEO_4$-LysAlaPheAspIleThrTyrValArgLeuLysPhe-$NH_2$ SEQ ID NO:26) where the PEO could be $PEO_4$ or $PEO_{12}$. As shown in FIG. 7, colonies of stem cells cultured on the surface containing Ac-KGGNGEPRGDTYRAY-$NH_2$ (SEQ ID NO:4), the BSP sequence (FIG. 7B) demonstrated similar colony morphology to MATRIGEL™ (FIG. 7A) as assessed by BCIP staining of the cells. Growth of stem cells was not observed on the swellable (meth)acrylate substrate (formulation no. 1) alone (FIG. 7C). FIG. 8 shows AttoPhos measurements, expressed as a percentage of MATRIGEL™ performance, for SA1 formulation, with increasing peptide concentration at 1, 10, 100 and 1000 µM. As shown in FIG. 8, adhesion and growth of undifferentiated stem cells on swellable (meth)acrylate formulation SA1A surfaces containing Ac-KGGNGEPRGDTYRAY-NH$_2$ (SEQ ID NO:4), the BSP sequence was peptide concentration dependent. Together, these data suggest that Ac-KGGNGEPRGD-TYRAY-NH$_2$ (SEQ ID NO:4), the BSP sequence, conjugated using 1000 µM concentration, can support adhesion and growth of undifferentiated H7 hES cells under chemically defined medium condition.

Figure 9:
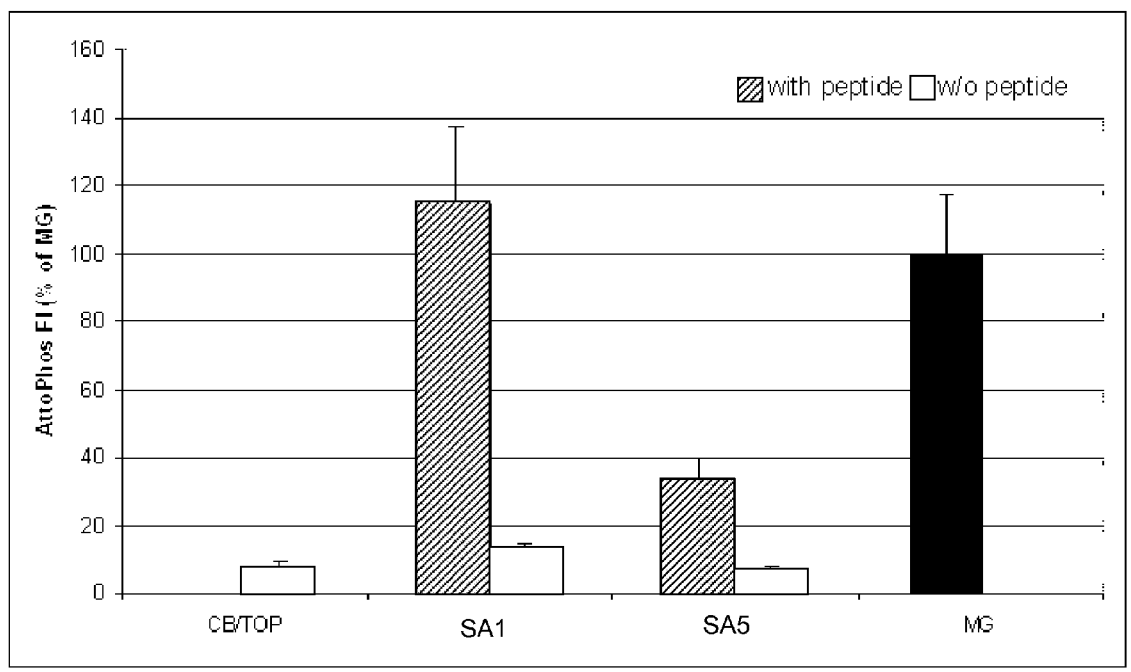
FIG. 9 is a graph illustrating the relative number of undifferentiated human embryonic stem cells (by AttoPhos fluorescence intensity) cultured in a chemically defined medium cultured on embodiments of swellable (meth)acrylate substrates.

Referring now to FIG. 9, the way in which the swellable (meth)acrylate coating is prepared and the components of the swellable (meth)acrylate affect the ability of Ac-KG-GNGEPRGDTYRAY-NH$_2$ (SEQ ID NO:4), the BSP sequence to support growth of undifferentiated stem cells. CB/TOP is uncoated cyclic olefin copolymer cell culture ware (plasma treated TOPAS®). SA1A is a swellable (meth) acrylate formulation with and without conjugated Ac-KG-GNGEPRGDTYRAY-NH$_2$ (SEQ ID NO:4) (as identified in FIG. 6). SA5 an alternative swellable (meth)acrylate formulation shown in Table 1 with or without conjugated Ac-KG-GNGEPRGDTYRAY-NH$_2$ (SEQ ID NO:4). MG is MATRIGEL™ control. As shown in FIG. 9, Formulation SA5 did not provide a coating that supported undifferentiated hES cell culture in the presence of chemically defined media comparable to that shown by MATRIGEL™. Without being limited by theory, this could be because there may be a significant amount of poly(ethylene glycol) 600 without carboxyethyl acrylate copolymerized at the ends, possibly creating a brush layer on the SA surface, instead of a network of polymers. As shown in FIG. 9, Ac-KGGNGEPRGDTYRAY-NH$_2$ (SEQ ID NO:4), the BSP sequence conjugated to Formulation SA1 resulted in comparable AttoPhos FI as compared to MATRIGEL™ control. This is in contrast to Formulation SA1A, which showed about 60% of MATRIGEL™ AttoPhos FI with conjugated Ac-KGGNGEPRGDTYRAY-NH$_2$ (SEQ ID NO:4), the BSP sequence (as shown in FIG. 6 and FIG. 8). As discussed above, the components of Formulations SA1 and SA1A were essentially identical, with only the manner in which the coating layers were prepared differing (SA1A: 0.1% at 5 microliters; SA1: 0.25% at 2 microliters). The thickness of the coating may be important. For example, in embodiments, it may be important to maintain the SA coating thickness below 0.5 µm. Accordingly, the manner in which the swellable (meth)acrylate substrate is prepared, as well as the chemical composition and swellable (meth)acrylate structure can affect the ability of a peptide-conjugated swellable (meth)acrylate surface to support culture of undifferentiated stem cells in a chemically defined medium.

Example 7

Figure 10:
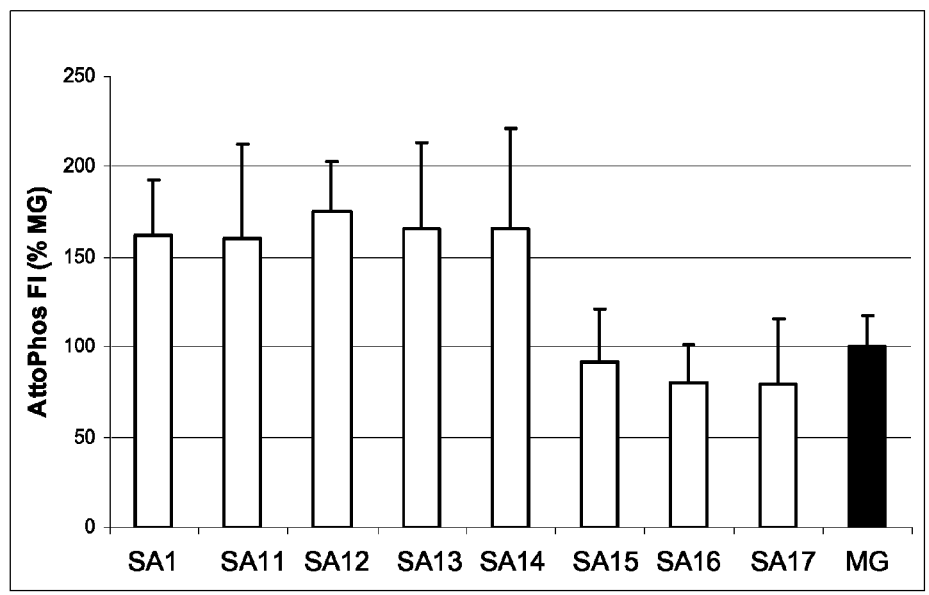
FIGS. 10A and 10B are bar graphs illustrating the relative number of undifferentiated H7 hES cells (by AttoPhos fluorescence intensity) under chemically defined medium condition on embodiments of swellable (meth)acrylate formulations after conjugated with peptide Ac-KGGNGEPRGDTYRAY-NH$_2$ (SEQ ID NO:4).
Figure 10:
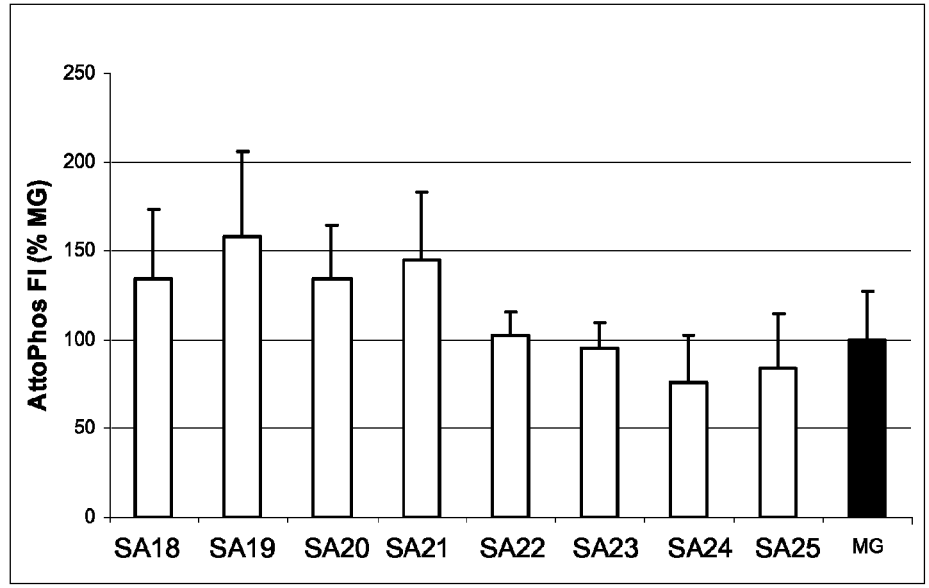

Testing of Additional SA Coatings Conjugated to Ac-KGGNGEPRGDTYRAY-NH$_2$ (SEQ ID NO:4) the BSP Sequence Additional swellable (meth)acrylate layers (SA layers or coatings) conjugated to Ac-KGGNGEPRGDTYRAY-NH$_2$ (SEQ ID NO:4), the BSP sequence were prepared and tested according to the EXAMPLES above. FIG. 10A and FIG. 10B are bar graphs of AttoPhos measurements of attachment and growth of undifferentiated H7 hES cells under chemically defined medium condition on different swellable (meth)acrylate formulations after conjugated with peptide Ac-KG-GNGEPRGDTYRAY-NH$_2$ (SEQ ID NO:4). The AttoPhos fluorescent intensity (FI) for cells on all screened surfaces was normalized to FI of cells on MATRIGEL™ (FIG. 10). All of the swellable (meth)acrylate formulations reported in FIG. 10A and FIG. 10B demonstrated similar or higher AttoPhos FI compared to MATRIGEL™ control and similar to MATRIGEL™ colony morphology as assessed by BCIP staining of the cells (data not shown).

For the swellable (meth)acrylate formulations reported in FIG. 10, the network was polymerized from either highly hydrophilic monomer such as acrylamide or mildly hydrophilic monomer such as hydroxypropyl methacrylate. The ratio of hydrophilic monomer ranged from 60 to 90%. The ratio of carboxyl-group containing functional monomer ranged from 10% to 30%. The ratio of cross-linking monomers ranged from 1% to 10%. After conjugated with BSP-RGD peptide Ac-KGGNGEPRGDTYRAY-NH$_2$ (SEQ ID NO:4), all of the tested formulations supported similar or higher hESC attachment than the positive control, MATRIGEL™, in chemically defined, animal free condition.

Example 8

Testing of Additional Peptides Conjugated to SA1

In the EXAMPLES above, Ac-KGGNGEPRGDTYRAY-NH$_2$ (SEQ ID NO:4), the BSP peptide, was shown to support culture of undifferentiated hESCs in chemically-defined, animal-free conditions when conjugated to a swellable (meth) acrylate polymer layer. Ac-KGGNGEPRGDTYRAY-NH$_2$ (SEQ ID NO:4), the BSP peptide incorporated the RGD adhesion epitope of Bonesialo protein (BSP) from mouse. Additional RGD containing peptides have been identified. However, not all RGD sequences may result in the same level of cell culture performance for every cell type. Some cell types may culture better on different specific peptides. The sequences flanking the RGD motif may significantly influence the degree of cell adhesion and influence the post adhesion differentiation processes. Without being limited by theory, it may be that integrin mediated cell adhesion may incorporate multiple cellular events of cell attachment including cell spreading with stress fibers and focal adhesions. Without being limited by theory, it may be that peptide conjugated (meth)acrylate scaffolds allow for these integrin mediated cell binding events. In this Example, the impact of conjugating different RGD containing peptides to embodiments of the SA coating are explored. Specifically, data showing the response of undifferentiated stem cells to embodiments of RGD peptides where the RGD epitope is derived from the human fibronectin protein conjugated to (meth) acrylate coatings are presented.

Fibronectin is a cell adhesive protein. A polypeptide having the cell-attaching activity of fibronectin and incorporating the RGD epitope was previously identified (see, e.g. U.S. Pat. No. 4,661,111). In this EXAMPLE, a 15 mer sequence (SEQ ID NO:12) (designated as long-FN or 1-FN) from the human fibronectin sequence was conjugated to the SA1 SA coating. The impact of a shorter, commercially available (American Peptide Co., Inc.) 7-mer fibronectin sequences (SEQ ID NO:11) (designated as short-FN or s-FN) conjugated to SA1 was also investigated. Without being limited by theory, it may be that short peptides are expected to have limited conformational stability and may result in reduced cell adhesion properties. The s-FN polypeptide is a 6-mer sequence derived from human fibronectin where an additional Lys amino residue at the C-terminus. In addition to being half the size of the 15-mer epitope 1-FN, this 6-mer s-FN peptide will attach via the C-terminus and thus change the orientation of the RGD epitope on the surface of the cell culture vessel.

In addition, due to the differences in the location of the conjugating amino acid residue within the peptides the 1-FN and s-FN RGD sequences present the RGD epitope to extracellular integrins in two different and opposing orientations.

Figure 11:
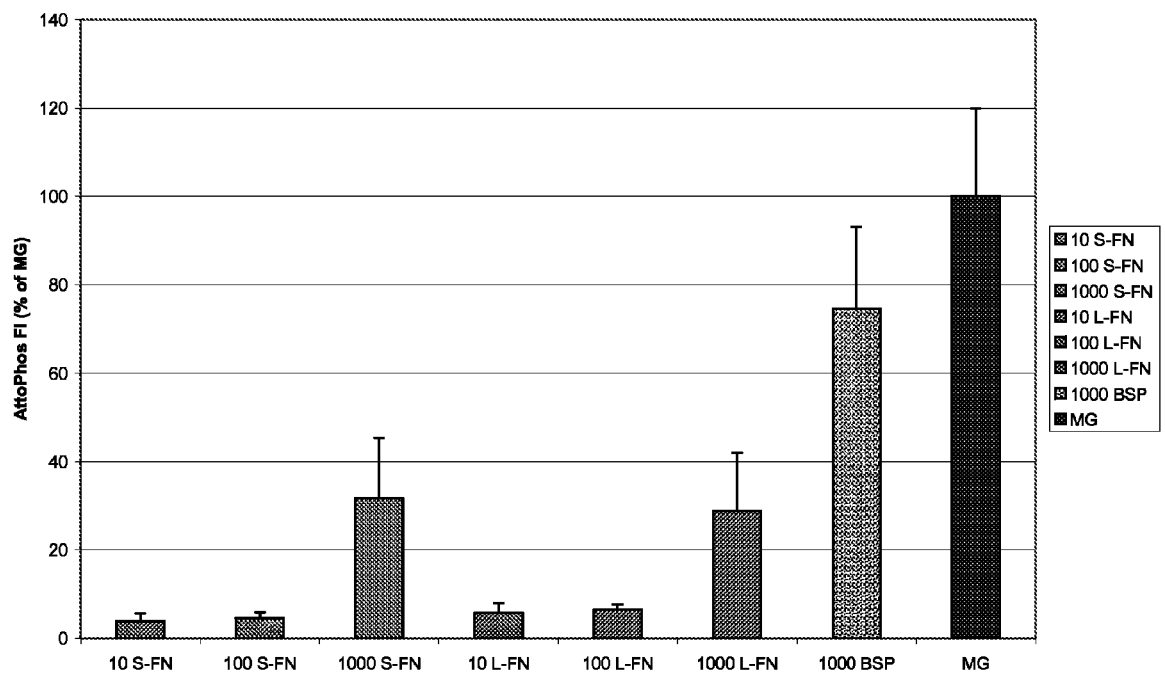
FIG. 11 is a bar graph illustrating the relative number of undifferentiated H7 hES cells (by AttoPhos fluorescence intensity) cultured on 10-, 100- and 1000-concentrations of 1-FN (SEQ ID NO:12), s-FN (SEQ ID NO:11) and Ac-KG-GNGEPRGDTYRAY-NH$_2$ (SEQ ID NO:4) conjugated to embodiments of swellable (meth)acrylate coatings.

In this EXAMPLE, the 1-FN (SEQ ID NO:12), s-FN (SEQ ID NO:11) and Ac-KGGNGEPRGDTYRAY-NH$_2$ (SEQ ID NO:4), the BSP peptides were conjugated to a (meth)acrylate layer made from Formulation SA1 as described in the EXAMPLES above. AttoPhos studies were performed as described in EXAMPLE 5. The results are shown in FIG. 11. FIG. 11 is a bar graph showing Attophos staining of hESCs grown on gradients of fibronectin conjugated swellable (meth)acrylate. S-FN is the 7-mer fibronectin peptide conjugated acrylate. L-Fn is the 15-mer fibronectin peptide conjugated acrylate. 10-, 100- and 1000-reflect the input peptide concentration (μM) for creating these coatings.

As shown in FIG. 11, the short fibronectin sequence (s-FN) is comparable in performance to the long fibronectin sequence, 1-FN. While the BSP sequence appeared to better support the culture of undifferentiated stem cells (relative to the fibronectin sequences), it may be that any amino acid sequences of the form Yaa$_1$Xaa$_n$ArgGlyAspXaa$_m$Yaa$_1$ (SEQ ID NO:1) where Xaa and Yaa are any naturally occurring or synthetic amino acid and where at least one Xaa or Yaa has a functionality that enables nucleophillic addition/amide bond formation with the surface carboxyl groups, would be acceptable choices for peptide based cell culture scaffolds.

Example 9

Testing of Additional Peptides Conjugated to SA1:Cyclic Peptides

In the EXAMPLES above 15-mer Ac-KGGNGEPRGD-TYRAY-NH$_2$ (SEQ ID NO:4), the BSP peptide was shown to support culture of undifferentiated hESCs in chemically-defined, animal-free conditions when conjugated to a swellable (meth)acrylate polymer layer. Without being limited by theory, it may be that short flexible peptides do not maintain their native conformation in aqueous media very well. The issue of conformational instability may be most prevalent in very short peptides. To mimic the pseudo-beta turn like conformation of the putative RGD epitope in the native protein, strategies have been developed for peptide cyclization using very short peptides such as pentamers or octamers. In this EXAMPLE, cyclic 13 and 17-mer RGD peptides are conjugated to embodiments of SA coatings.

In addition, poly ethylene oxide (PEO) linker conjugated RGD sequences are conjugated to embodiments of SA coatings. Without being limited by theory, the addition of a spacer/linker may improve the bio-availability of the peptide epitope by projecting the peptide epitope away from the SA coating. In addition, the hydrophilic nature of the ethylene oxide units in a PEO linker may reduce non-specific protein adsorption to the surface. The linker was added to the polypeptide by American Peptide Company in Vista, Calif.

All the peptides used in this EXAMPLE were synthesized at American Peptide Company, Inc., 1271 Avenida Chelsea, Vista, Calif. 92081 or CEM Corporation, P.O. Box 200, 3100 Smith Farm Road, Matthews, N.C. 28106.

The following peptides were conjugated to a swellable (meth)acrylate layer, Formulation SA1, as described in the EXAMPLES above. See Table 5 for cyclic structures.

(i) Ac-LysGlyGlyAsnGlyGluProArgGlyAspThrTyrArgAlaTyr-NH$_2$, "BSP"; (SEQ ID NO:4)

(ii) NH$_2$-PEO4-AsnGlyGluProArgGlyAspThrTyrArgAlaTyr-NH$_2$, "linker BSP"; (SEQ ID NO:5)

(iii) Ac-LysGlyGlyLys$^4$AsnGlyGluProArgGlyAspThrTyrArgAlaTyrAsp$^{17}$-NH$_2$, Lys$^4$-Asp$^{17}$ amide cycle, "cyclic BSP 17-mer"; (SEQ ID NO:6)

(iv) Ac-LysGlyGlyLys$^4$GluProArgGlyAspThrTyrArgAsp$^{13}$-NH$_2$, Lys$^4$-Asp$^{13}$ amide cycle, "cyclic BSP 13-mer"; (SEQ ID NO:7)

(v) Ac-LysGlyGlyCys$^4$AsnGlyGluProArgGlyAspThrTyrArgAlaTyrCys$^{17}$-NH$_2$, Cys$^4$-Cys$^{17}$ disulfide bonded cycle, "disulfide-BSP 17-mer" shown as FORMULA 4; and (SEQ ID NO:8)

(vi) Ac-LysGlyGlyCys$^4$GluProArgGlyAspThrTyrArgCys$^{17}$-NH$_2$, Cys$^4$-Cys$^{13}$ disulfide bonded cycle, "disulfide-BSP 13-mer". (SEQ ID NO:9)

TABLE 5

Figure 13:
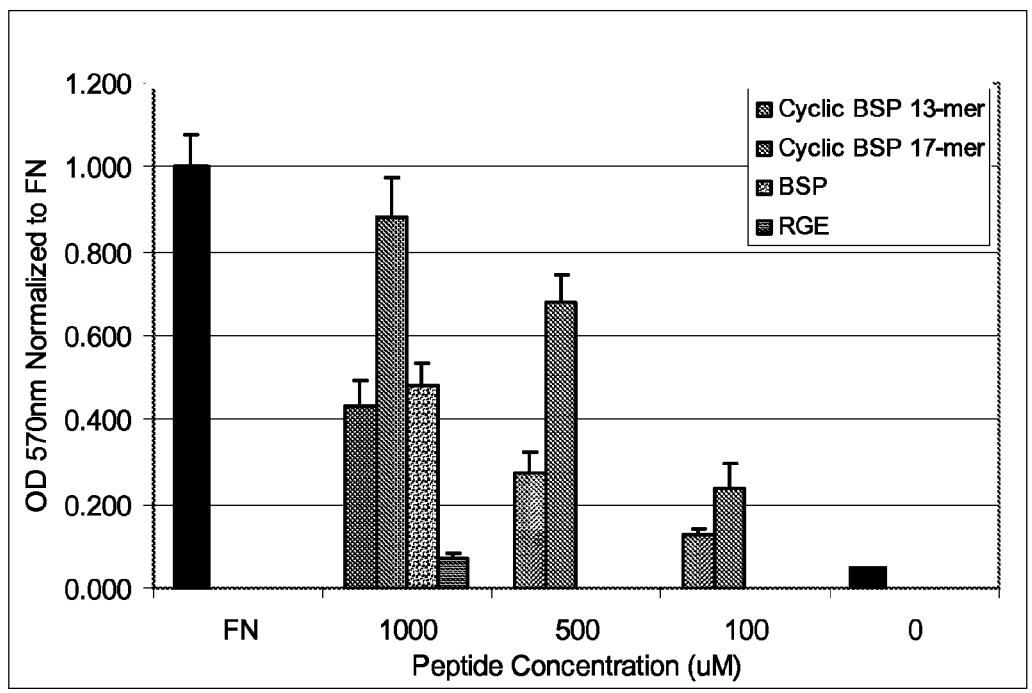
FIG. 13 is a bar graph showing relative HT-1080 attachment (via OD 570 nm) to amide bonded, cyclized polypeptides conjugated to a swellable (meth)acrylate layer.

(SEQ ID NO: 6)
Ac-LysGlyGlyLys$^4$AsnGlyGluProArgGlyAspThr TyrArgAlaTyrAsp$^{17}$-NH$_2$, Lys$^4$-Asp$^{17}$ "cyclic BSP 17-mer" amide cycle, (FIG. 13)

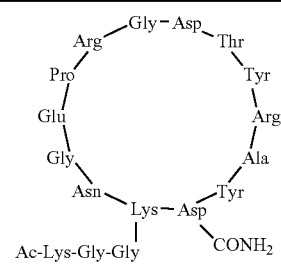

TABLE 5-continued

| | |
|---|---|
| (SEQ ID NO: 7)<br>Ac-LysGlyGlyLys⁴GluProArgGlyAspThrTyrArgAsp¹³-NH₂, Lys⁴-Asp¹³ amide cycle "cyclic BSP 13-mer"<br>(FIG. 13) | 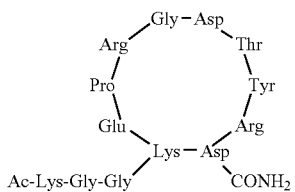 |
| (SEQ ID NO: 8)<br>Ac-LysGlyGlyCys⁴AsnGlyGluProArgGly<br>AspThrTyrArg AlaTyrCys¹⁷-NH₂, Cys⁴-Cys¹⁷<br>disulfide bonded cycle, "disulfide-BSP 17-mer"<br>(FIG. 12) | 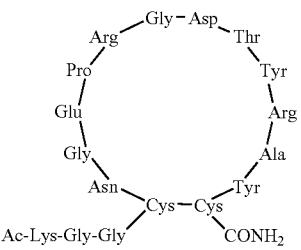 |
| (SEQ ID NO: 9)<br>Ac-LysGlyGlyCys⁴GluProArgGlyAsp<br>ThrTyrArgCys¹⁷-NH₂, Cys⁴-Cys¹³<br>disulfide bonded cycle, "disulfide-BSP 13-mer"<br>(FIG. 12) | 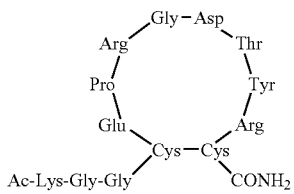 |

Two chemical strategies were utilized to synthesize cyclic peptides. The first strategy utilized an amide linkage created by cyclizing the free amino functionality on the lysine side chain and free carboxy functionality on the aspartic acid side chain. The second strategy utilized a di-sulfide linkage created between the free sulfhydryl side chains on the two cysteine amino acids in the peptide sequence (see WO1989005150). These cyclizations were performed by CEM Corporation in Matthews, N.C.

The 13-mer and 17-mer amide linked cyclic peptide resulted in cyclic RGDs that were 10 and 14 amino acids, respectively. Similarly, the 13-mer and 17-mer disulfide linked cyclic peptide resulted in cyclic RGDs that were 10 and 14 amino acids, respectively.

Figure 12:
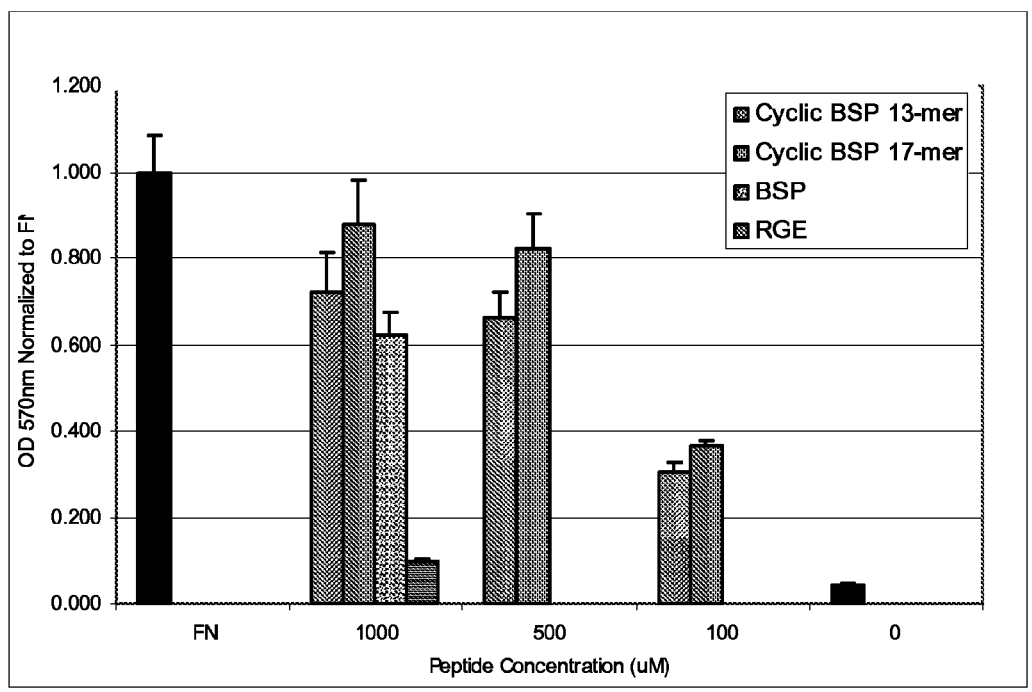
FIG. 12 is a bar graph showing relative HT-1080 attachment (via OD 570 nm) to di-sulfide bonded, cyclized polypeptides conjugated to a swellable (meth)acrylate layer.

FIG. 12 shows adhesion of HT-1080 to SAP-BSP(cyclic) where the BSP peptide was cyclized by disulfide bonds (SEQ ID NO:8) and (SEQ ID NO:9), Ac-LysGlyGlyAsnGlyGluProArgGlyAspThrTyrArgAlaTyr-NH₂ (SEQ ID NO:4) (1000 mM), and non adhesive peptide GRGESPIYK (SEQ ID NO:30) (RGE, 1000 mM) normalized to extracellular matrix protein fibronectin (FN, 5 mg/mL)-coated surfaces. (SEQ ID NO:8) and (SEQ ID NO:9) cyclic BSP disulfide peptide-conjugated (meth)acrylate surfaces supported HT-1080 adhesion similar to Ac-LysGlyGlyAsnGlyGluProArgGlyAspThrTyrArgAlaTyr-NH₂ (SEQ ID NO:4)-conjugated (meth)acrylate. FIG. 13 shows that (SEQ ID NO:6) (amide cyclic BSP 17mer) and (SEQ ID NO:7) (amid cyclic BSP 13mer), amide cyclized BSP peptide-conjugated (meth) acrylates also supported HT-1080 adhesion similarly to linear BSP-conjugated (meth)acrylates, Ac-LysGlyGlyAsnGlyGluProArgGly AspThrTyrArgAlaTyr-NH₂ (SEQ ID NO:4).

Figure 14:
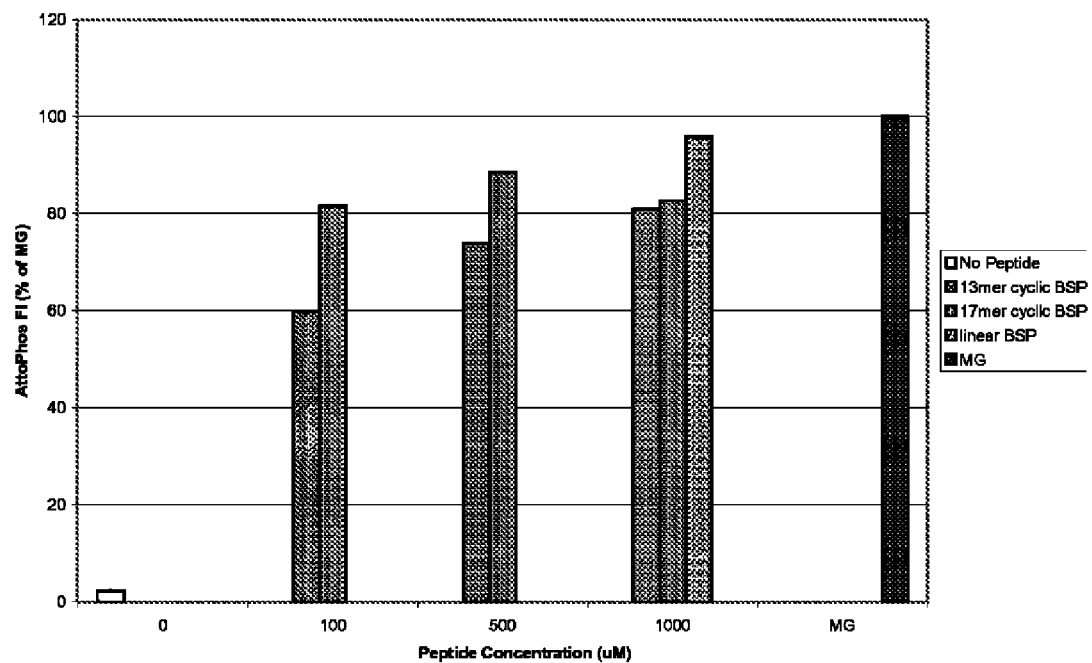
FIG. 14 is a bar graph illustrating the relative number of undifferentiated H7 hES cells (by AttoPhos fluorescence intensity) cultured on a swellable (meth)acrylate layer with conjugated amide bonded, cyclized polypeptides.

Results of AttoPhos staining of human embryonic stem cells (hESCs) cultured on a swellable (meth)acrylate layer with conjugated amide bonded, cyclized polypeptides are shown in FIG. 14. Briefly, H7 hESC were cultured on SA conjugated with linear or cyclic BSP peptide to form SAP-BSP or SAP-BSP(cyclic) surfaces. BSP was cyclized using amide bonding. After 48 hrs in culture on SAP-BSP (SEQ ID NO:4) surfaces and SA coatings conjugated to (SEQ ID NO:6) (amide cyclic BSP 17mer) and (SEQ ID NO:7) (amid cyclic BSP 13mer), cells subjected to AttoPhos assay. MATRIGEL™-coated substrate wells were used as positive control. As shown in FIG. 14, H7 cells showed similar adhesion/growth response on cyclic and linear BSP conjugated SA surfaces. No significant difference in cell response was observed between 13mer and 17mer versions of amide bond-cyclized SAP-BSP(cyclic) surfaces. The results suggest that both amide bonded, cyclized and liner BSP conjugated SA can support adhesion/growth of undifferentiated H7 hESC.

Figure 15:
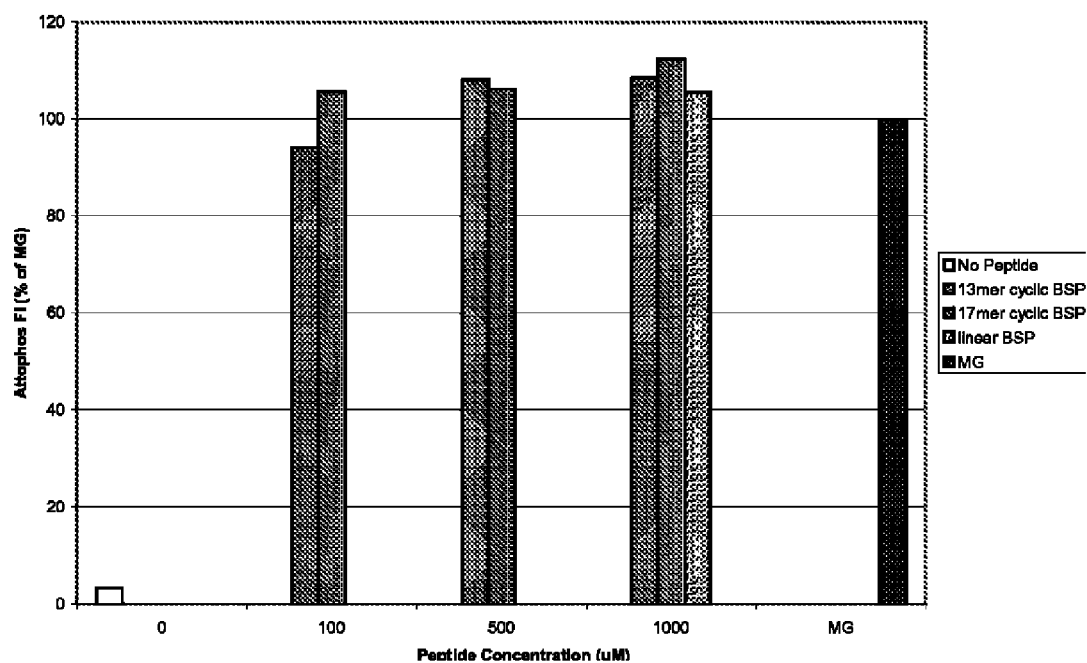
FIG. 15 is a bar graph illustrating the relative number of undifferentiated H7 hES cells (by AttoPhos fluorescence intensity) cultured on a swellable (meth)acrylate layer with conjugated di-sulfide bonded, cyclized polypeptides.

FIG. 15 shows results of AttoPhos staining of human embryonic stem cells (hESCs) cultured on a swellable (meth) acrylate layer with conjugated di-sulfide bonded, cyclized polypeptides (SEQ ID NO:8) (di-sulfide cyclic BSP 17mer) and (SEQ ID NO:9) (disulfide cyclic BSP 13mer) compared to SA-BSP (SEQ ID NO:4) and MATRIGEL™. Briefly, H7 hESC were cultured for 48 hours on SA conjugated with linear cyclic BSP peptides to form SAP-BSP or SAP-BSP (cyclic) surfaces. After 48 hrs in culture, cells were fixed and subjected to AttoPhos assay. As shown in FIG. 15, H7 cells showed similar adhesion/growth response on cyclic and linear BSP conjugated SA surfaces. No difference in cell response was observed between 13mer and 17mer versions of SAP-BSP(cyclic) surfaces. Interestingly, disulfide bonded SAP-BSP surfaces demonstrated higher cell AttoPhos response compared to linear SAP-BSP at lower (100 μM) concentration (compare AttoPhos FI for 100 uM peptide concentration in FIG. 15 and FIG. 8). The results suggest that, in embodiments, both disulfide bonded cyclic and liner BSP conjugated SA can support undifferentiated H7 adhesion/growth, with cyclic BSP showing higher cell response at lower peptide concentration.

In embodiments the present invention provides a cell culture article, comprising: a substrate having a surface; a swellable (meth)acrylate layer disposed on the surface of the substrate, wherein the swellable (meth)acrylate layer is formed from a composition comprising a carboxyl group-containing (meth)acrylate monomer, a cross-linking (meth)acrylate monomer, and a hydrophilic monomer capable of polymerizing with the carboxyl group-containing (meth)acrylate monomer and the cross-linking (meth)acrylate monomer; and a peptide conjugated to a carboxyl group resulting from the carboxyl group-containing monomer of the swellable (meth)acrylate layer. In embodiments, the swellable (meth)acrylate layer has an equilibrium water content in water of between about 5% and about 50% or between about 10% and about 40%. In embodiments, the carboxyl group-containing (meth)acrylate monomer is 2-carboxyethylacrylate. In embodiments, the cross-linking (meth)acrylate monomer is tetra(ethylene glycol) dimethacrylate or tetra(ethylene glycol) diacrylate. In embodiments the hydrophilic monomer is selected from the group consisting of hydroxyethyl methacrylate, hydroxypropyl methacrylate, 2-hydroxyethyl acrylate, 1-vinyl-2-pyrrolidone, di(ethylene glycol) ethyl ether methacrylate, acrylamide, ethylene glycol methyl ether methacrylate or 3-sulfopropyldimethyl-3-methacrylamidopropyl-ammonium. In embodiments, the ratio, by volume, of the cross-linking (meth)acrylate monomer to the carboxy group-containing meth(acrylate) monomer to the hydrophilic monomer is about 1-10 to about 10-40 to about 60-90. Or, in embodiments, the ratio by volume, of the cross-linking (meth)acrylate monomer to the carboxy group-containing meth(acrylate) monomer to the hydrophilic monomer is about 3 to 20 to 80. In embodiments, the swellable (meth)acrylate layer is free of polypeptide crosslinkers.

In embodiments, the peptide conjugated to a carboxyl group resulting from the carboxyl group-containing monomer of the swellable (meth)acrylate layer comprises an amino acid sequence of $Yaa_1Xaa_nArgGlyAspXaa_mYaa_1$ (SEQ ID NO:1), where n is an integer of 0 to 4, m is an integer of 0 to 5, 1 is 0 or 1 each Xaa is independently any native or biomimetic amino acid, and Yaa is independently any native or biomimetic amino acid With the proviso that peptide includes at least one amino acid having functionality that enables nucleophilic addition to a free carboxyl group of the swellable (meth)acrylate layer, wherein the free carboxyl group results from the carboxyl group-containing (meth)acrylate monomer. In embodiments, Yaa comprises lysine.

In additional embodiments, the peptide conjugated to a carboxyl group resulting from the carboxyl group-containing monomer of the swellable (meth)acrylate layer comprises an amino acid sequence of $Yaa_1Xaa_mZaa\ Xaa_nArgGlyAspXaa_m\text{-}Baa\ Xaa_mYaa_1$ (SEQ ID NO:3), where n is an integer of 0 to 4, m is an integer of 0 to 5, 1 is 0 or 1 each Xaa is independently any native or biomimetic amino acid, Zaa and Baa are each independently any native or biomimetic amino acid having covalent bonds formed between atoms of their respective side chains to form a cyclic portion of the polypeptide, and Yaa is independently any native or biomimetic amino acid; with the proviso that the polypeptide includes at least one native or biomimetic amino acid having functionality that enables nucleophilic addition to a free carboxyl group of the swellable (meth)acrylate layer, wherein the free carboxyl group results from the carboxyl group-containing (meth)acrylate monomer. In embodiments, Yaa comprises lysine.

In embodiments, the peptide conjugated to a carboxyl group resulting from the carboxyl group-containing monomer of the swellable (meth)acrylate layer comprises LysGlyGlyAsnGlyGluProArgGlyAspThrTyrArgAlaTyr (SEQ ID NO:4); AsnGlyGluProArgGlyAspThrTyrArgAlaTyr (SEQ ID NO:5) LysGlyGlyLys$^4$ AsnGlyGluProArgGlyAspThr-TyrArgAlaTyrAsp$^{17}$ (SEQ ID NO:6), where Lys$^4$ and Asp$^{17}$ together form an amide bond to cyclize a portion of the polypeptide; LysGlyGlyLys$^4$GluProArgGlyAspThrTryArgAsp$^{13}$ (SEQ ID NO:7), here Lys$^4$ and Asp$^{13}$ together form an amide bond to cyclize a portion of the polypeptide; LysGlyGly Cys$^4$AsnGlyGluProArgGlyAspThrTyrArgAlaTyrCys$^{17}$ (SEQ ID NO:8), where Cys$^4$ and Cys$^{17}$ together form a disulfide bond to cyclize a portion of the polypeptide; LysGlyGlyCys$^4$GluProArgGlyAspThrTryArgCys$^{13}$ (SEQ ID NO:9), where Cys$^4$ and Cys$^{13}$ together form a disulfide bond to cyclize a portion of the polypeptide; GlyArgGlyAspSerProLys (SEQ ID NO:11); and LysGlyGlyAlaValThrGlyArgGlyAspSerProAlaSerSer (SEQ ID NO:12).

In embodiments, the swellable (meth)acrylate layer has a uniform thickness. In embodiments, the swellable (methacrylate) layer is less than about 2 micrometers in thickness.

Example 10

Doubling Time

H7 human embryonic stem cells, cultured as described in Example 4 above, were passaged every 4-5 days (around 75% confluency) using enzymatic sub-cultivation procedure (collagenase IV treatment), followed by washing with DPBS, scraping and re-suspending in chemically defined culture medium. Cell colony morphology, cell number, viability and hESC-specific marker expression profile relative to cells cultured in parallel with Matrigel surface was assessed at each passage. The doubling time (DT) on each surface coating was assessed using the following formula where DT=doubling time in hours; T=total time in culture in hours; $D_0$=seeding cell density and D=harvesting cell density:

$$DT = T \times \log 2 / \log D - \log D_0 \qquad \text{FORMULA 2}$$

Figure 16:
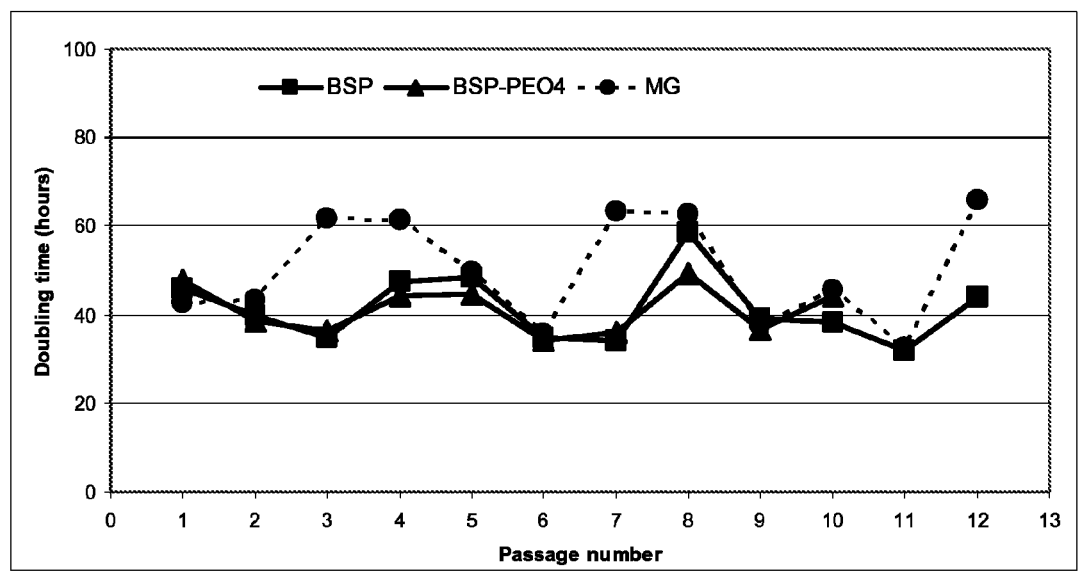
FIG. 16 is a graph showing the doubling time for undifferentiated H7 hESCs cultured under chemically-defined, animal produce free medium conditions on a MATRIGEL™ (MG) surface, a swellable (meth)acrylate layer with conjugated defined RGD-containing peptide (SEQ ID NO:4) (BSP), and a swellable (meth)acrylate layer with conjugated defined RGD-containing peptide with a linker (BSP-PE04).

FIG. 16 shows results of doubling time experiments for undifferentiated H7 hESCs cultured under chemically-defined, animal produce free medium conditions on a MATRIGEL™ (MG) surface, SA1 with conjugated defined RGD-containing peptide (BSP) (SEQ ID NO:4), and a SA1 conjugated RGD-containing peptide with a linker (BSP-PE0$_4$) NH$_2$-PE0$_4$-AsnGlyGluProArgGlyAspThrTyrArg AlaTyr (SEQ ID NO:5) Briefly, H7 hESC were cultured on SAP-BSP or BSP-PEO4 conjugated SA in 6-well plates for ten consecutive passages in chemically defined medium (Xvivo10+bFGF and TGFb1). Cells cultured on MATRIGEL™-coated substrate surface were used as positive control. At each passage, cell doubling time, cell viability and expression of Oct4 hESC marker (data not shown) was assessed. In embodiments, the culture of undifferentiated stem cells through 10 passages is considered "long term culture" of these cells. In embodiments, culture of cells for 5 passages, 7 passages, 10 passages, 11 passages, 12 passages, 13 passages, 14 passages, 15 passages, 16 passages, 17 passages, 18 passages, 19 passages, 20 passages or longer is considered long term culture. Those of skill in the art will recognize that, although a population of cells in culture may be or may become mixed cell types, a sufficient percentage of cells in the cell culture must remain in the undifferentiated state for the passage to be considered successful. In embodiments of the present invention, passages are successful passages which retain a sufficient percentage of cells in their undifferentiated state so as to be considered an undifferentiated population of cells.

In embodiments A method for culturing an isolated population of undifferentiated stem cells, comprising: providing a cell culture article having a substrate, a synthetic polymer layer disposed on the substrate, and a peptide conjugated to the synthetic polymer layer, wherein the peptide comprises and amino acid sequence of RGD; culturing the undifferentiated stem cells on the polypeptide conjugated to the synthetic polymer layer of the cell culture article in a chemically defined cell culture medium and maintaining the cells in culture for at least 5 passages, at least 10 passages or more passages. In embodiments, the chemically defined culture medium comprises basic fibroblast growth factor and transforming growth factor-β1. In embodiments, the stem cells are human stem cells or human embryonic stem cells, which may be H1 or H7 human embryonic stem cells.

In additional embodiments include a method for culturing an isolated population of cells, comprising: providing a cell culture article having a substrate, a swellable (meth)acrylate layer disposed on the substrate, and a peptide conjugated to the swellable (meth)acrylate layer, wherein swellable (meth)acrylate layer is formed from a composition comprising a carboxyl group-containing (meth)acrylate monomer, a cross-linking (meth)acrylate monomer, and a hydrophilic monomer capable of polymerizing with the carboxyl group-containing (meth)acrylate monomer and the cross-linking (meth)acrylate monomer, and wherein the peptide comprises and amino acid sequence of RGD; contacting the cells with the polypeptide conjugated to the swellable (meth)acrylate layer of the cell culture article; and culturing the cells in a chemically defined cell culture medium to maintain the cells in culture. In embodiments, the cells are undifferentiated stem cells, human embryonic stem cells, or H1 or H7 cells. In embodiments, the method further comprises passaging the cells five or more times on additional cell culture articles in chemically the defined cell culture medium, wherein 50% or more of the cells remain in an undifferentiated state following each of the five or more passages or ten or more times. In embodiments, the chemically defined culture medium comprises basic fibroblast growth factor and transforming growth factor-β1 which may be .about 80 ng/ml basic fibroblast growth factor and about 0.5 ng/ml transforming growth factor-β1.

As shown in FIG. 16, H7 hESC doubling time on SAP-BSP or SAP-BSP-PEO$_4$ surfaces was more consistent compared to the doubling time of cells cultured on MATRIGEL™-coated surface, which fluctuated dramatically from passage to passage. These fluctuations could be due to lot-to-lot and prep-to-prep inconsistency of MATRIGEL™-coated surface. Average cell doubling time on SAP-BSP and SAP-BSP-PEO$_4$ was 41(+/−6) hours, while on MATRIGEL™ average cell doubling time was 50(+/−12) hrs, reflecting higher level of inconsistency on MATRIGEL™ surface.

Average cell viability and Oct4-positive cell fraction was identical on SAP-BSP and MATRIGEL™ surfaces: 86(+/−2) % for viability, 92(+/−4) % for Oct4-positive cell fraction. The results suggest that, in embodiments, SAP-BSP and SAP-BSP-PEO$_4$ surfaces can support long term culture of undifferentiated H7 hESC, including multiple passaging, without affecting cell viability or undifferentiated status, but improving consistency of cell doubling time.

Example 11

Testing of Additional Cell Types

Human embryonic stem cells are difficult to culture. Therefore, they are a good model to use to show the applicability of embodiments of cell culture surfaces to provide relevant cell culture conditions for difficult-to-culture cells. However, many cell types are "anchorage dependent." That is, many cells require extra cellular matrix or serum to remain healthy in long term cell culture. Without being limited by theory, it may be that for adherent cells requiring serum containing media, the serum provides a variety of adhesion proteins in addition to mitogenic factors (such as various growth factors) needed for cell culture. Adhesion proteins (which may include fibronectin, laminin, collagen etc.) present in the serum may become absorbed on plastic cell culture ware to form attachment surfaces for adherent cells. This EXAMPLE shows that applications for embodiments of peptide conjugated (meth)acrylate coatings of the present invention are not limited to stem cells. The data reported in this EXAMPLE demonstrate that embodiments of synthetic peptide conjugated (meth)acrylate coatings of the present invention are capable of replacing the need for serum containing media or a biological coating.

In the following EXAMPLES, human adult mesenchymal stem cells (hMSC), cardiomyocytes (differentiated from H7 human embryonic stem cells), human fibrosarcoma (HT1080) cells and HepG2/C3A cells are tested against embodiments of the peptide-conjugated swellable (meth)acrylate cell culture substrates of the present invention.

For the results presented in EXAMPLES 12-17, cells were cultured on a surface formed from Formulation SA1 of EXAMPLE 1 and EXAMPLE 2 conjugated with Ac-LysGlyGlyAsnGlyGluProArgGly AspThrTyrArgAlaTyr-NH2 (SEQ ID NO:4) (BSP) according to EXAMPLE 2. The cell culture surfaces were prepared as described in EXAMPLE 1, unless indicated otherwise.

Example 12

Bone Marrow Derived hMSC Cells

Bone marrow derived hMSC (Lonza, cat # PT-2501) were expanded in 10% FBS containing standard culture medium (MSCGM from Lonza, cat # PT-3001) on a tissue culture treated T-75 flask for one passage. hMSC cells generally require 2-10% serum in their culture media. On day 8, cells were harvested at ~80-90% confluency with trypsin, washed twice with DPBS and seeded at the density of 7,000 cells/cm$^2$ on either TCT-PS 6 well-plates form Corning or 6 well plates coated with Ac-LysGlyGlyAsnGlyGluProArgGlyAspThrTyrArgAlaTyr-NH2 (SEQ ID NO:4)-conjugated swellable (meth)acrylate of formulation SA1. Both systems were studied with 3 different media conditions described below.

1) MSCGM, standard culture medium for hMSC culture supplemented with 10% fetal bovine serum (FBS) is the standard conditions used for in-vitro culture of hMSCs. Used in conjunction with cell culture treated culture ware.
2) StemPro MSC-SFM (Invitrogen, cat # A10332-01), serum-free medium designed for hMSC culture. These chemically defined media require use with CellStart humanized ECM matrix (Invitrogen, cat # A10142).
3) Xvivo10 (Lonza, cat #04-743Q)+GF (GF, growth factors ~20 ng/ml bFGF+0.5 ng/ml TGFb1)

Cells were re-fed with corresponding medium every 2-3 days. Cell adhesion/spreading, morphology and growth was monitored every day. On day 7 cells were harvested with trypsin and cell count was performed using TB and hemacytometer. MSCGM supplemented with 10% FBS is the standard media for in-vitro culture of hMSC on plastic culture ware and was the control for this study. StemPro MSC-SFM and the XVivo10+GF (Lonza) media were chosen as they are two well known chemically defined, serum free media used in the field. The StemPro MSC-SFM media is specifically designed for the culture of hMSCs and contains proprietary growth factors etc. SAP-BSP surfaces were compared with these standards using both serum containing and chemically defined media.

FIG. 17A-C are photomicrographs showing hMSC growth on embodiments of the present invention compared to TCT, in three different media conditions. In FIG. 17A, MSCM+10% FBS media was used to culture hMSCs on SAP-BSP surfaces (upper images) and TCT (lower images). MSCM+10% FBS represents the standard media condition used for commercial culture of hMSC for clinical applications. In the middle images, FIG. 17B, MSC+SFM is StemPro a specialized media marketed by Invitrogen Corp. for hMSC culture that contains proprietary cocktail of growth factors. In FIG. 17C, Xvivo+GF was used. This media combination incorporates Xvivo basal media, supplemented with bFGF and TGFb1 as described above in EXAMPLE 4.

FIG. 17A shows that in 10% FBS-supplemented MSCM media, hMSC cells appear similar on TCT surfaces and on embodiments of the SAP-BSP surfaces of the present invention. FIGS. 17B and C show that in the absence of FBS, SAP-BSP embodiments of the synthetic swellable (meth)acrylate surfaces of the present invention provide better cell growth than TCT surfaces. FIGS. 17 B and C show the morphology and cell number on all culture conditions on day 7. The cell number on BSP-acrylate surface is significantly higher than on TCT for both serum-free conditions, with cell number in Xvivo+GF condition exceeding cell number in 10% FBS condition. In addition, initial cell attachment and spreading (2-20 hrs) was more efficient in 10% FBS medium compared to serum-free conditions for both surfaces. At later time points (3-7 days) cell survival/proliferation on BSP-acrylate surface under serum-free conditions was higher than on TCT. Embodiments of the present invention can enable the culture of hMSCs in serum free media.

Figure 18:
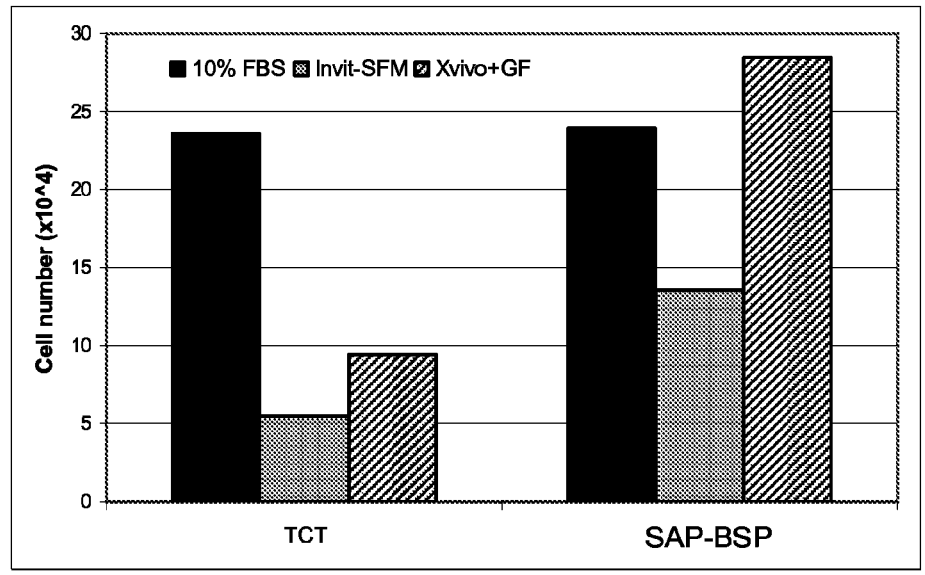
FIG. 18 is a bar graph showing a comparison of hMSC cell number on TCT and SAP-BSP after 7 days in culture under different media conditions including defined media.

FIG. 18 is a bar graph showing a comparison of hMSC cell number on TCT and BSP-(meth)acrylate after 7 days in different defined media conditions, as defined above. While both surfaces perform comparably in the presence of FBS, the SAP-BSP (BSP peptide acrylate) surface provides a significantly improved cell culture surface compared to TCT in the absence of FBS.

Example 13

H7 hESC Cells

Figure 19:
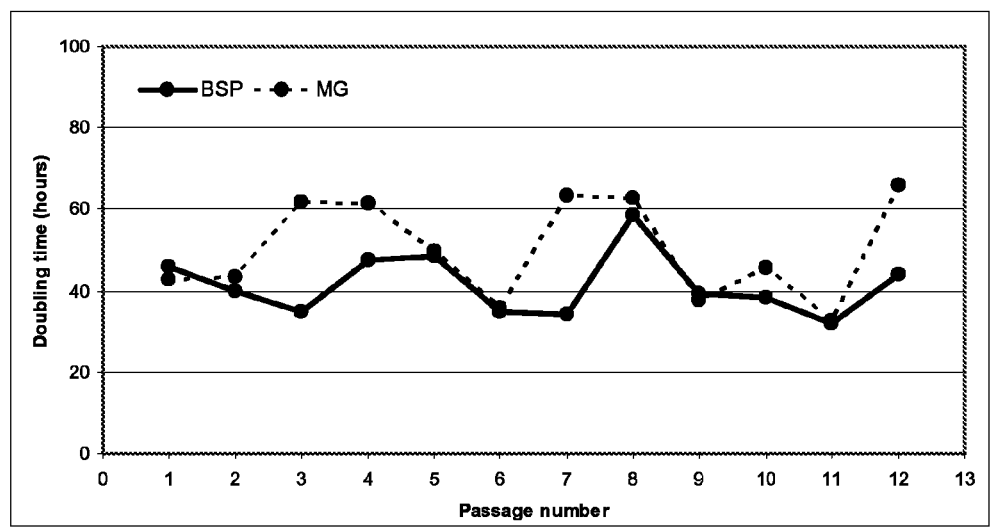
FIG. 19 is a graph showing a comparison of the H7 hESCs doubling time when cultured on an embodiment of the cell culture surface of the present invention compared to MATRIGEL™ coating across 10 passages.
Figure 20:
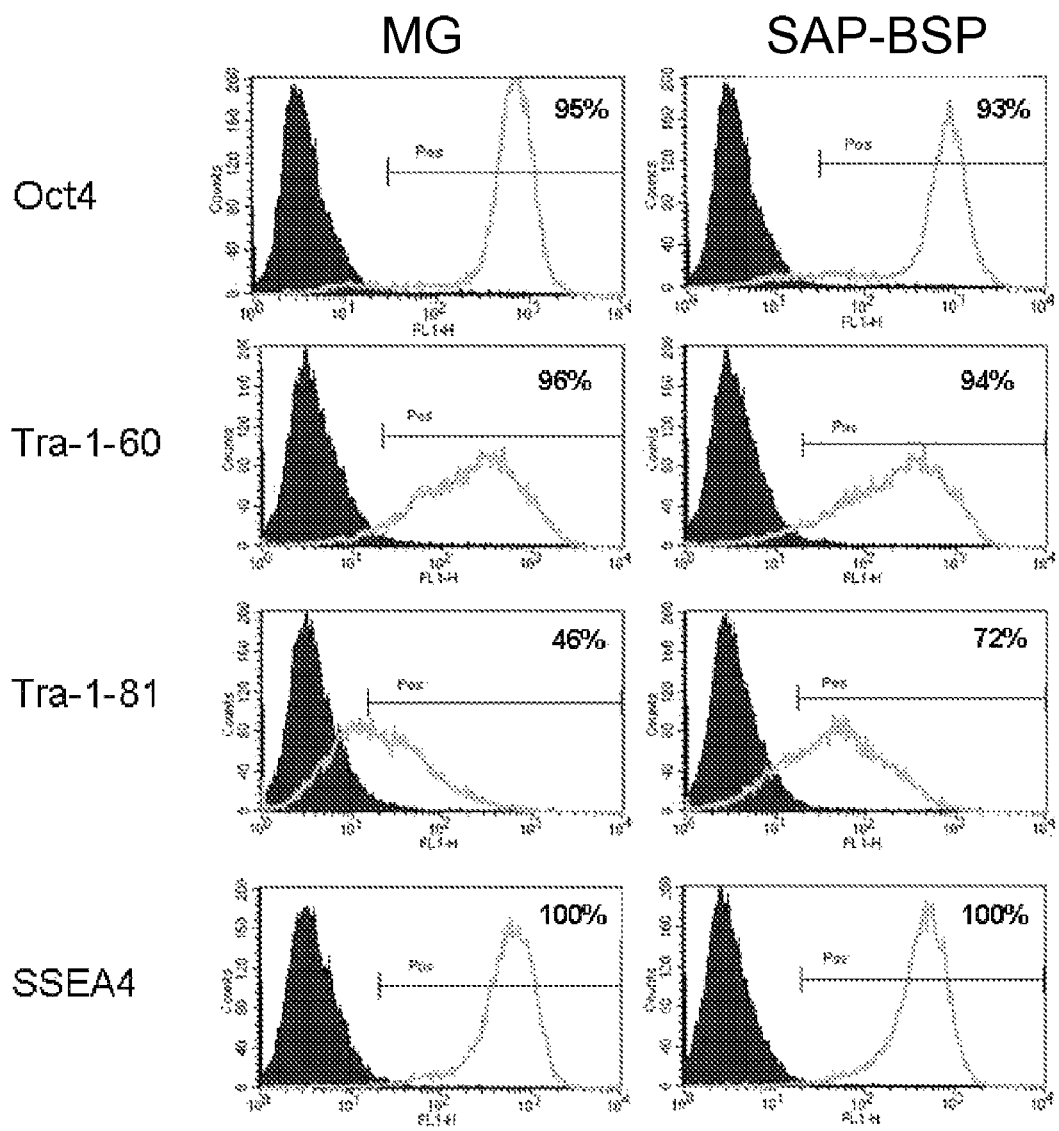
FIG. 20 shows the results of flow cytometry analyses of hESC-specific markers for H7 hESC cultured on MATRIGEL™ control or SAP-BSP surface for 10 passages.

In EXAMPLES above, the use of embodiments of swellable (meth)acrylate surfaces conjugated to peptides for in-vitro expansion of hESCs was described. In this EXAMPLE, additional data that demonstrates the use of embodiments of SAP surfaces for long-term in vitro expansion of hESC cells. While data is shown for H7 hESCs, H1 hESC cell lines have also been expanded on these surfaces with similar results. A representation of the comparison of doubling time for H7 cells on BSP conjugated and Matrigel coated surfaces in the media conditions presented in EXAMPLE 4 is presented in FIG. 19. The data indicates that the synthetic SAP surface is comparable or better in cell culture performance to Matrigel™ coating. In addition, cells cultured on BSP conjugated acrylate surface showed similar to MATRIGEL™ expression of hESC-specific markers as determined by flow cytometry analyses (FIG. 20).

Example 14

Flow Cytometry

At the end of each passage, H7 hES cells cultured on synthetic surfaces or MATRIGEL™ were analyzed for hESC marker expression using flow cytometry. The entire staining procedure was performed at 4° C. Briefly, for each sample $5\times10^5$ cells (fixed and permibialized for Oct4, live cells for Tra-1-60, Tra-1-81, and SSEA4 markers) were re-suspended in 50 microliter of blocking solution (10% HI goat serum in DPBS) and incubated for 15 min, followed by addition of 50 microliter of marker-specific primary antibody (0.5 microgram/sample) or corresponding isotype control (0.5 microgram/sample) in blocking buffer for 30 min. After washing with 2 ml Staining buffer (SB) from BD Biosciences), cells were incubated with corresponding secondary antibody (0.25 microgram/sample) in SB for 30 min protected from light. After washing with SB, cells were stained with PI (2 microgram/ml in SB) for 5 min, for viability assessment. 30,000 gated events (gating was set for PI-negative viable cell population) were acquired for each sample using the FACS Calibur (BD Biosciences). All analyses were done using CellQuest Pro software (BD). Results are shown in FIG. 20. Results showed that expression of hESC-specific markers were very similar on MATRIGEL™ and on the SAP-BSP synthetic surface.

Example 15

Differentiation of H7 hESCs to Cardiomyocytes

The culture of undifferentiated hESC on embodiments of BSP conjugated swellable (meth)acrylate was disclosed In EXAMPLE 13. In this EXAMPLE, the use of the same surface for the differentiation of these cells to cardiomyocytes is disclosed. Stem cell derived cardiomyocytes may be obtained by any suitable methods. One of ordinary skill would recognize that this class of peptide conjugated (meth)acrylates can also be used enable the differentiation of hESC cells into other lineages such as pancreatic islet cells, neural cells, osteogenic cells etc.

Laflamme et al., "Cardiomyocytes derived from human embryonic stem cells in pro-survival factors enhance function of infracted rats, *Nature Biotechnology*, 25: 1015-1024 (2007) describes a method for differentiating hESCs in culture. Briefly, undifferentiated human embryonic stem cells, such as those derived from the female H7 human embryonic stem cell line, may be seeded on MATRIGEL™-coated plates at a density of about 100,000 cells/cm² and re-fed daily with hES cell growth medium (KO DMEM+20% Serum replacement, 1 mM l-glutamine, 1% NEAA, 0.1 mM 2-ME plus hbFGF at 80 ng/ml and TGFb1 at 0.5 ng/ml). To induce differentiation, KO-SR may be replaced with RPMI-B27 medium (available from Invitrogen) supplemented with about 100 ng/ml human recombinant activin A (available from R&D Systems) for about 24 hours, followed by 10 ng/ml human recombinant BMP4 (available from R&D Systems) for 72 hours. Of course, any other suitable method may be employed.

After long term culture of hESC on synthetic SAP-BSP surfaces in chemically defined medium, cells still retain ability to differentiate into cell types of therapeutic interest. H7 cells were cultured on SAP-BSP surfaces for 10 passages and then were differentiated into cardiomyocytes (CM) using the same SAP-BSP surface. Direct differentiation protocol of LaFlamme (Supra.) was used. Briefly, H7 cells were first preconditioned for 10-14 days in "knock-out serum-replacement" media (KO-SR) [KO-DMEM (Invitrogen, #10829018); 20% KO-SR (Invitrogen #10828-028); 1% Non-essential Amino Acids (Invitrogen #11140-050); 1 mM L-Glutamine; 0.1 mM Beta-Mercaptoethanol; 80 ng/ml hbFGF and 0.5 ng/ml hTGF-β1 (R&D Systems; #234-FSE/CF and #240-B). Upon formation of post-confluent cell monolayers, CM differentiation was induced by sequential addition of the following recombinant growth factors in RPMI 1640 medium (Invitrogen #11875) supplemented with B27 (Invitrogen #17504044): human Activin A-100 ng/ml (R&D Systems #338-AC-CF) for 24 hrs followed by human BMP4 (bone morphongenic protein 4)-10 ng/ml (R&D Systems #314-BP-CF) for 72 hrs. The cells were then allowed to recover for an additional 2-week period in RPMI 1640-B27 medium. Medium was exchanged every 2-3 days until beating CM were observed in cultures.

Example 16

Cardiomyocytes (Differentiated from H7 Human Embryonic Stem Cells)

Based on information and belief, all published reports on hESC differentiation into physiologically relevant (functional) cardiomyocytes require substrates that are coated with Matrigel™ or other ECM proteins. The data reported in the present EXAMPLE demonstrate that embodiments of the SAP surfaces of the present invention, including SAP-BSP synthetic RGD-containing polypeptide conjugated swellable (meth)acrylate surfaces are capable of replacing the need for 2D/3D scaffolds coated with biological coatings.

Figure 21:
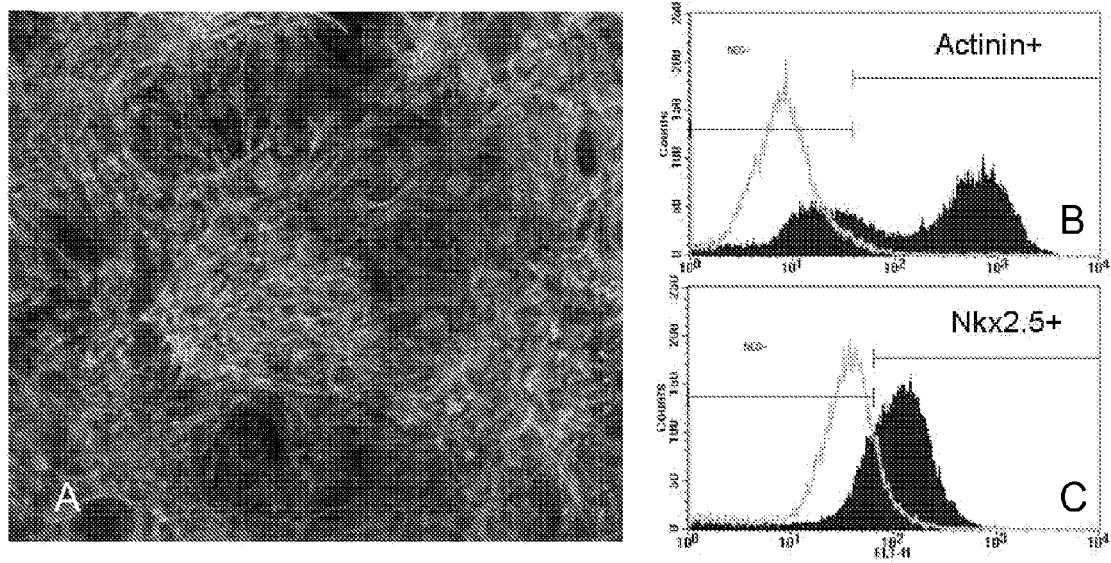
FIG. 21A is a fluorescence image showing actinin and Nkx2.5+ staining for cardiomyocytes differentiated on SAP-BSP peptide conjugated acrylate surfaces.
FIG. 21B shows flow cytometry data for αActinin and FIG. 21C shows flow cytometry data for Nkx2.5 cardiomyocytes differentiated from H7 hESC on an embodiment of the cell culture surface of the present invention.

For CM marker assessment, differentiated cells were either fixed on 6-well plates and processed for Nkx2.5/α-actinin double immunostaining (shown on FIG. 21A) or harvested, fixed and processed for α-actinin (FIG. 21B) or Nkx2.5 (FIG. 21C) flow cytometric analysis. These results show that after long-term culture (10+ passages) of undifferentiated H7 hESC on SAP-BSP synthetic surface in chemically defined medium, cells can still be differentiated into cardiomyocytes. The differentiation efficiency was very similar to that seen on MATRIGEL™ surface (data not shown). Also the data suggest that SAP-BSP surface can be used to substitute currently used MATRIGEL™ for direct differentiation of hESC into cardiomyocytes.

Example 17

HT1080 Cells

Using HT1080 cells, we demonstrate in this EXAMPLE that this class of synthetic peptide conjugated (meth)acrylate coatings can provide suitable cell culture surfaces for any cell type that requires biological coatings or serum containing media.

The culture of human fibrosarcoma (HT 1080) cells were chosen to demonstrate the universality of the peptide conjugated acrylate surfaces. HT 1080 cells are routinely grown in serum containing media. The ATCC recommended protocol for growth of this cell type requires ATCC-formulated Eagle's Minimum Essential Medium, (Catalog No. 30-2003) supplemented with 10% fetal bovine serum. It is believed that adhesion proteins within the serum facilitate the attachment of these cells to the plastic surface.

Figure 22:
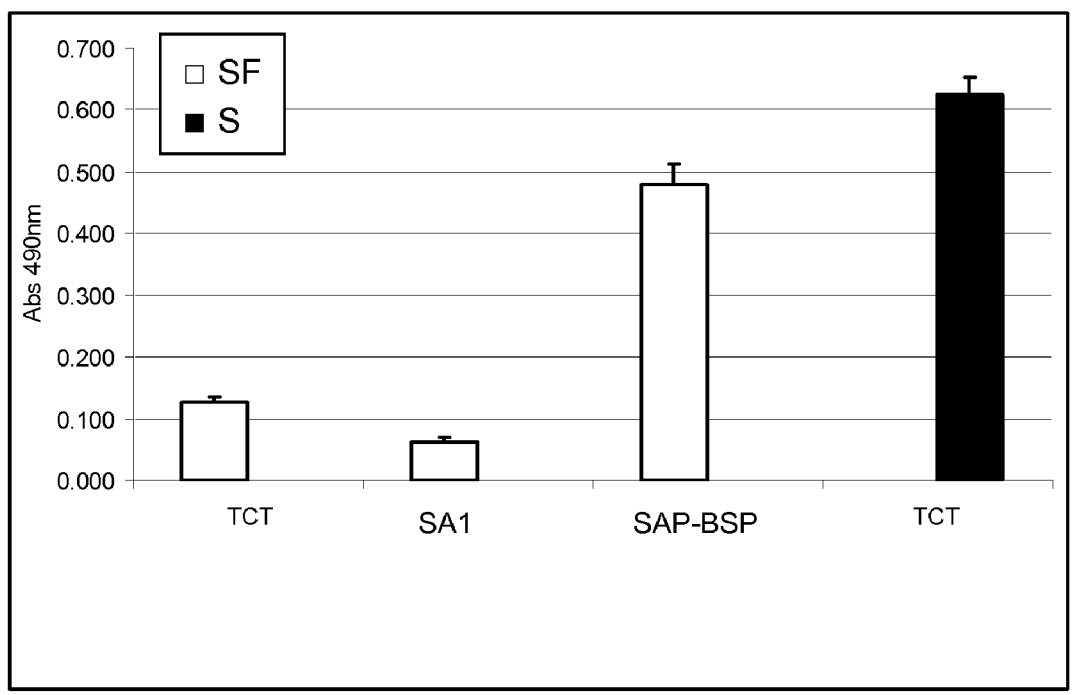
FIG. 22 is a bar graph comparing HT1080 cell proliferation (via absorbance at 490 nm) data of HT-108-cells on TCT, SAP-BSP surface, in the presence and absence of serum.
Figure 23:
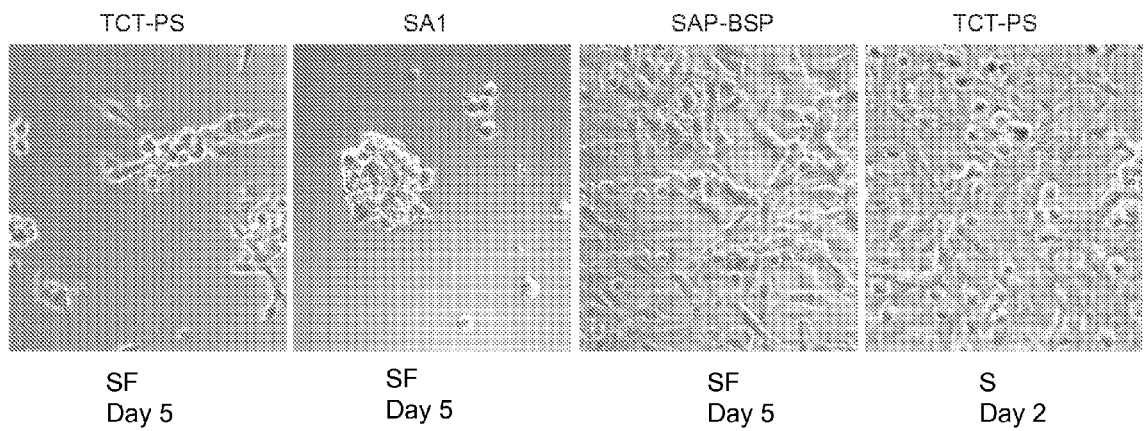
FIG. 23 are images comparing the morphology of HT-1080 cells on TCT and (meth)acrylate coating and BSP conjugated coatings in the presence and absence of serum.

For this EXAMPLE, HT-1080 (ATCC# CCL-121) cells were grown to 70% confluency in Iscove's Modified Dulbecco's Medium (IMDM, Lonza, 12-722Q) containing 10% fetal bovine serum (FBS, Lonza, 14-502F) in a tissue-cultured treated T150 flask (TCT, Corning, 430825). Cell media was replenished at 70% confluency with either serum-containing (IMDM+10% FBS) or serum-free (IMDM) media for one day prior to cell harvest. Cells were harvested at 100% confluency with 0.05% trypsin-EDTA (Gibco/Invitrogen, 25300) and washed twice with Dulbecco's Phosphate-buffered saline (DPBS, Gibco/Invitrogen, 14190). Cells were seeded at the density of 25,000 cells/cm$^2$ in either serum containing or serum free IMDM (+16 ng/mL Recombinant Human FGF basic (R&D Systems 234-FSE/CF) and +0.5 ng/mL Recombinant Human TGF-B1 (R&D Systems, 240-B-002)) onto the following 96 well plates: TCT-PolyStyrene (TCT-PS, Corning, 3603), swellable (meth)acrylate (SA1) coated Xenor, and SAP-BSP coated Xenor. Cells were re-fed with corresponding medium every 2-3 days. Cell adhesion/spreading, morphology and growth was monitored every day. A cell proliferation assay (CellTiter 96® AQueous One Solution Cell Proliferation Assay, Promega, G358B) was used to assess relative cell number on each surface at cell confluency—day 2 (serum containing) and day 5 (serum-free), according to the manufacturer's protocol. FIG. 22 is a bar graph comparing cell titer data of HT-1080-cells on TCT, SA1 (meth)acrylate-coated and SAP-BSP conjugated coating, in the presence of serum (S, black bar) and in the absence (SF, white bars) of serum. FIG. 23 shows photomicrograph comparing the morphology of HT-1080 cells on TCT and (meth)acrylate coating and BSP conjugated coatings in the presence and absence of serum. The data from the CellTiter assay is shown in FIG. 22 and a comparison of cell morphology is shown in FIG. 23. TCT-PS is plasma treated TCT surface. SA1 is the SA1 formulation from Table 1. SAP-BSP is the BSP-peptide conjugated (SEQ ID NO: 4) SA1 formulation. The first three images are serum-free conditions (SF, Day 5) and the last panel is in the presence of serum, at day 2. This data shows the feasibility of using the RGD polypeptide conjugated swellable (meth)acrylate coatings for cell culture of HT-1080 cells. HT-1080 cells provide a representative of engineered cell lines that require the use of serum for attachment purposes.

Example 18

Attachment of HepG2/C3A Cells to Sap Layers with Conjugated Laminin Polypeptides HepG2/C3A cells (ATCC # CRL-10741) were plated at 25,000 cells per well in 100 μl media in triplicate on SAP surfaces, BD BioCoat™ Collagen I and Corning CellBind® treated Topas™ in a 96 well format and cultured at in Eagle's Minimum Essential Medium (ATCC #30-2003) supplemented with 1% penicillin-streptomycin (Invitrogen #15140-155). The culture medium was not supplemented with fetal bovine serum (as recommended by the cell line supplier) nor was the SAP surface exposed to fetal bovine serum. The culture plates were incubated at 37° C., in 5% CO$_2$ and 95% relative humidity for 24 hours. The cell culture plates having the SA surfaces were prepared as described in EXAMPLE 1. Peptides were conjugated according to EXAMPLE 2. The polypeptides conjugated to the SA layer are listed in Table 5. Polypeptides exhibiting results better than 75% attachment compared to Collagen I (see FIG. 24) are marked with an asterix in Table 6. The line in FIG. 24 indicates 75% performance of cells on Collagen 1.

TABLE 6

Polypeptides conjugated to SA layer

| Sequence | Source | CLS No |
|---|---|---|
| KGGGQKCIVQTTSWSQCSKS (SEQ ID NO:13) | Cyr61 res 224-240 | *CLS 01005 |
| KYGLALERKDHSG (SEQ ID NO:14) | TSP1 res 87-96 | CLS 01010 |
| KGGSINNNRWHSIYITRFGNMGS (SEQ ID NO:15) | mLMα1 res 2179-2198 | CSL 01015 |
| KGGTWYKIAFQRNRK (SEQ ID NO:16) | mLMα1 res 2370-2381 | *CLS 01020 |
| KGGTSIKIRGTYSER (SEQ ID NO:17) | mLMγ1 res 650-261 | CLS 01025 |
| KYGTDIRVTLNRLNTF (SEQ ID NO:18) | mLMγ1 res 245-257 | CLS 01030 |
| KYGSETTVKYIFRLHE (SEQ ID NO:19) | mLMγ1 res 615-627 | *CLS 01035 |
| KYGKAFDITYVRLKF (SEQ ID NO:21) | mLMγ1 res 139-150 | *CLS 01050 |
| KYGAASIKVAVSADR (SEQ ID NO:20) | mLMα1 res 2122-2132 | CLS 01040 |
| Ac-KGGNGEPRGDTYRAY (SEQ ID NO:4) | BSP | CLS 01045 |
| Ac-KGGNGEPRGDTRAY (SEQ ID NO:31) | BSP-Y | CLS 01080 |
| KYGRKRLQVQLSIRT (SEQ ID NO:22) | mLMα1 res 2719-2730 | CLS 01055 |
| KGGRNIAEIIKDI (SEQ ID NO:23) | LMβ1 | CLS 01060 |
| Ac-KGGPQVTRGDVFTMP-NH2 (SEQ ID NO:29) | VN | CLS 01075 |
| GRGDSPK (SEQ ID NO:11) | Short FN | CLS 01065 |
| Ac-KGGAVTGRGDSPASS-NH$_2$ (SEQ ID NO:12) | Long FN | CLS 01070 |

The attachment of the HepG2/C3A cells was determined using a Cytotoxicity Assay (Promega CytoTox 96® Non-Radioactive Cytotoxicity Assay # G1780) which estimates the number of living cells attached to the culture surfaces. After 24 hours of in culture, the cells were vigorously washed with phosphate buffer, lysed via the introduction of the lysis buffer solution and incubation at 37 C for 1 hour to release lactate dehydrogenase (LDH) enzyme from the viable cells that remain attached to the culture surfaces. The biological activity of the released lactate dehydrogenase enzyme was measured via absorbance at 490 nm using a plate reader (Victor 3 from PerkinElmer).

Figure 24:
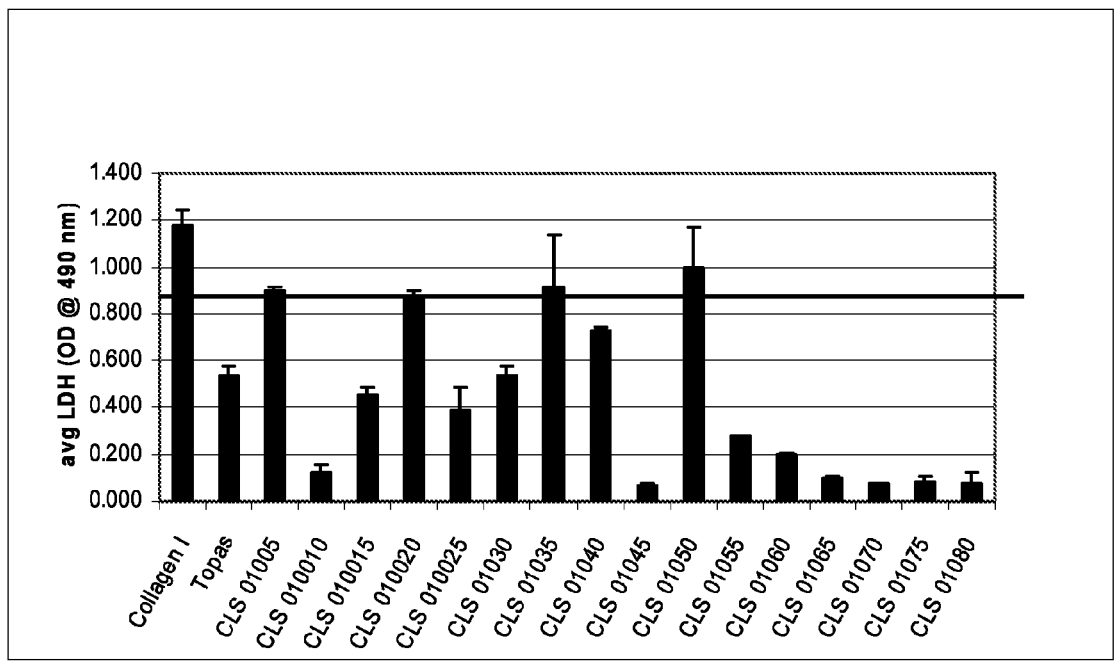
FIG. 24 is a bar graph comparison of the estimated number of viable cells (absorbance of LDH activity) on SA-Ps, Collagen I and CellBind® treated Topas™.

The comparison of the estimated number of viable cells (absorbance of LDH activity) on SAPs, Collagen I and Cell-Bind® treated Topas™ is shown in FIG. 24. Comparison of the cell culture surfaces demonstrated that Corning SAPs with laminin peptide sequences KGGGQK-CIVQTTSWSQCSKS (SEQ ID NO:13), KGGTWYKI-AFQRNRK (SEQ ID NO:16), KYGSETTVKYIFRLHE (SEQ ID NO:19), and KYGKAFDITYVRLKF (SEQ ID NO:21 support serum-free attachment of HepG2/C3A cells ≧75% of Collagen I and greater than CellBind® treated Topas™. In addition, the HepG2/C3A cells cultured on the Corning SAPs exhibited similar cell morphology as the cells cultured on Collagen I.

Thus, embodiments of SYNTHETIC SURFACES FOR CULTURING CELLS IN CHEMICALLY DEFINED MEDIA are disclosed. One skilled in the art will appreciate that the arrays, compositions, kits and methods described herein can be practiced with embodiments other than those disclosed. The disclosed embodiments are presented for purposes of illustration and not limitation.

SEQUENCE LISTING

```
<160> NUMBER OF SEQ ID NOS: 31

<210> SEQ ID NO 1
<211> LENGTH: 5
<212> TYPE: PRT
<213> ORGANISM: Artificial Sequence
<220> FEATURE:
<223> OTHER INFORMATION: RGD-containing polypeptide
<220> FEATURE:
<221> NAME/KEY: MISC_FEATURE
<222> LOCATION: (1)..(1)
<223> OTHER INFORMATION: Xaa is Yaa(l) Xaa(n), where n is 0 to 4, l is 0
      or 1, each Xaa is independently any amino acid, Yaa is any amino
      acid
<220> FEATURE:
<221> NAME/KEY: MISC_FEATURE
<222> LOCATION: (5)..(5)
<223> OTHER INFORMATION: Xaa is Xaa(m)Yaa(l) , where m is 0 to 5, l is 0
      or 1, each Xaa is independently any amino acid, Yaa is any amino
      acid

<400> SEQUENCE: 1

Xaa Arg Gly Asp Xaa
1               5
```

```
<210> SEQ ID NO 2
<211> LENGTH: 5
<212> TYPE: PRT
<213> ORGANISM: Artificial Sequence
<220> FEATURE:
<223> OTHER INFORMATION: cyclic RGD-containing polypeptide
<220> FEATURE:
<221> NAME/KEY: MISC_FEATURE
<222> LOCATION: (1)..(1)
<223> OTHER INFORMATION: Xaa is ZaaXaa(n), where n is 0 to 4, each Xaa
      is independently any amino acid, and Zaa together with Baa form a
      covalent bond to cyclize the polypeptide
<220> FEATURE:
<221> NAME/KEY: MISC_FEATURE
<222> LOCATION: (5)..(5)
<223> OTHER INFORMATION: Xaa is Xaa(m)Baa, where m is 0 to 5, each Xaa
      is independently any amino acid, and Baa together with Zaa form a
      covalent bond to cyclize the polypeptide

<400> SEQUENCE: 2

Xaa Arg Gly Asp Xaa
1               5

<210> SEQ ID NO 3
<211> LENGTH: 5
<212> TYPE: PRT
<213> ORGANISM: Artificial Sequence
<220> FEATURE:
<223> OTHER INFORMATION: cyclic RGD-containing peptide with conjugation
      site
<220> FEATURE:
<221> NAME/KEY: MISC_FEATURE
<222> LOCATION: (1)..(1)
<223> OTHER INFORMATION: Xaa is Yaa(l)Xaa(m)ZaaXaa(n), where l is 0 or
      1, m is 0 to 5, n is 0 to 4, each Xaa is independently any amino
      acid, Yaa is any amino acid, and Zaa togehter with Baa form a
      covalent bond to cyclize the polypeptide
<220> FEATURE:
<221> NAME/KEY: MISC_FEATURE
<222> LOCATION: (5)..(5)
<223> OTHER INFORMATION: Xaa is Xaa(m)BaaXaa(m)Yaa(l), where l is 0 or
      1, m is 0 to 5, each Xaa is independently any amino acid, Yaa is
      any amino acid, and Baa togehter with Zaa form a covalent bond to
      cyclize the polypeptide

<400> SEQUENCE: 3

Xaa Arg Gly Asp Xaa
1               5

<210> SEQ ID NO 4
<211> LENGTH: 15
<212> TYPE: PRT
<213> ORGANISM: Artificial Sequence
<220> FEATURE:
<223> OTHER INFORMATION: Synthetic polypeptide including sequence
      derived from mouse bonesialo protein

<400> SEQUENCE: 4

Lys Gly Gly Asn Gly Glu Pro Arg Gly Asp Thr Tyr Arg Ala Tyr
1               5                   10                  15

<210> SEQ ID NO 5
<211> LENGTH: 12
<212> TYPE: PRT
<213> ORGANISM: Artificial Sequence
<220> FEATURE:
<223> OTHER INFORMATION: Synthetic polypeptide including sequence
      derived from mouse bonesialo protein

<400> SEQUENCE: 5

Asn Gly Glu Pro Arg Gly Asp Thr Tyr Arg Ala Tyr
```

```
<210> SEQ ID NO 6
<211> LENGTH: 17
<212> TYPE: PRT
<213> ORGANISM: Artificial Sequence
<220> FEATURE:
<223> OTHER INFORMATION: Synthetic polypeptide including sequence
      derived from mouse bonesialo protein
<220> FEATURE:
<221> NAME/KEY: MISC_FEATURE
<222> LOCATION: (4)..(4)
<223> OTHER INFORMATION: Lys at residue 4 froms amide bond with Asp at
      residue 17 to cyclize the polypeptide
<220> FEATURE:
<221> NAME/KEY: MISC_FEATURE
<222> LOCATION: (17)..(17)
<223> OTHER INFORMATION: Asp at residue 17 froms amide bond with Lysat
      residue 4 to cyclize the polypeptide

<400> SEQUENCE: 6

Lys Gly Gly Lys Asn Gly Glu Pro Arg Gly Asp Thr Tyr Arg Ala Tyr
1               5                   10                  15

Asp

<210> SEQ ID NO 7
<211> LENGTH: 13
<212> TYPE: PRT
<213> ORGANISM: Artificial Sequence
<220> FEATURE:
<223> OTHER INFORMATION: Synthetic polypeptide including sequence
      derived from mouse bonesialo protein
<220> FEATURE:
<221> NAME/KEY: MISC_FEATURE
<222> LOCATION: (4)..(4)
<223> OTHER INFORMATION: Lys at residue 4 forms amide bond with Asp at
      residue 13 to cyclize the polypeptide
<220> FEATURE:
<221> NAME/KEY: MISC_FEATURE
<222> LOCATION: (13)..(13)
<223> OTHER INFORMATION: Asp at residue 13 forms amide bond with Lys at
      residue 4 to cyclize the polypeptide

<400> SEQUENCE: 7

Lys Gly Gly Lys Glu Pro Arg Gly Asp Thr Tyr Arg Asp
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Synthetic polypeptide including sequence
      derived from mouse bonesialo protein
<220> FEATURE:
<221> NAME/KEY: MISC_FEATURE
<222> LOCATION: (4)..(4)
<223> OTHER INFORMATION: Cys at residue 4 forms a disulfide bond with
      Cys at residue 17 to cyclize the polypeptide
<220> FEATURE:
<221> NAME/KEY: MISC_FEATURE
<222> LOCATION: (17)..(17)
<223> OTHER INFORMATION: Cys at residue 17 forms a disulfide bond with
      Cys at residue 4 to cyclize the polypeptide

<400> SEQUENCE: 8

Lys Gly Gly Cys Asn Gly Glu Pro Arg Gly Asp Thr Tyr Arg Ala Tyr
1               5                   10                  15

Cys

<210> SEQ ID NO 9
```

```
<211> LENGTH: 13
<212> TYPE: PRT
<213> ORGANISM: Artificial Sequence
<220> FEATURE:
<223> OTHER INFORMATION: Synthetic polypeptide including sequence
      derived from mouse bonesialo protein
<220> FEATURE:
<221> NAME/KEY: MISC_FEATURE
<222> LOCATION: (4)..(4)
<223> OTHER INFORMATION: Cys at residue 4 forms disulfide bond with Cys
      at residue 13 to cyclize polypeptide
<220> FEATURE:
<221> NAME/KEY: MISC_FEATURE
<222> LOCATION: (13)..(13)
<223> OTHER INFORMATION: Cys at residue 13 forms disulfide bond with Cys
      at residue 4 to cyclize polypeptide

<400> SEQUENCE: 9

Lys Gly Gly Cys Glu Pro Arg Gly Asp Thr Tyr Arg Cys
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Synthetic polypeptide including sequence
      derived from mouse bonesialo protein
<220> FEATURE:
<221> NAME/KEY: MISC_FEATURE
<222> LOCATION: (1)..(1)
<223> OTHER INFORMATION: Xaa is any amino acid

<400> SEQUENCE: 10

Xaa Gly Gly Asn Gly Glu Pro Arg Gly Asp Thr Tyr Arg Ala Tyr
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: Synthetic polypeptide including sequence
      derived from human fibronectin

<400> SEQUENCE: 11

Gly Arg Gly Asp Ser Pro Lys
1               5

<210> SEQ ID NO 12
<211> LENGTH: 15
<212> TYPE: PRT
<213> ORGANISM: Artificial Sequence
<220> FEATURE:
<223> OTHER INFORMATION: Synthetic polypeptide including sequence
      derived from human fibronectin

<400> SEQUENCE: 12

Lys Gly Gly Ala Val Thr Gly Arg Gly Asp Ser Pro Ala Ser Ser
1               5                   10                  15

<210> SEQ ID NO 13
<211> LENGTH: 20
<212> TYPE: PRT
<213> ORGANISM: Artificial Sequence
<220> FEATURE:
<223> OTHER INFORMATION: Synthetic polypeptide including sequence
      derived from mouse laminin (CYR61)

<400> SEQUENCE: 13

Lys Gly Gly Gly Gln Lys Cys Ile Val Gln Thr Thr Ser Trp Ser Gln
```

```
                  1               5                  10                  15

Cys Ser Lys Ser
                 20

<210> SEQ ID NO 14
<211> LENGTH: 13
<212> TYPE: PRT
<213> ORGANISM: Artificial Sequence
<220> FEATURE:
<223> OTHER INFORMATION: Synthetic polypeptide including sequence
      derived from human thrombospondin 1

<400> SEQUENCE: 14

Lys Tyr Gly Leu Ala Leu Glu Arg Lys Asp His Ser Gly
1               5                  10

<210> SEQ ID NO 15
<211> LENGTH: 23
<212> TYPE: PRT
<213> ORGANISM: Artificial Sequence
<220> FEATURE:
<223> OTHER INFORMATION: Synthetic polypeptide including sequence
      derived from mouse laminin (SN)

<400> SEQUENCE: 15

Lys Gly Gly Ser Ile Asn Asn Asn Arg Trp His Ser Ile Tyr Ile Thr
1               5                  10                  15

Arg Phe Gly Asn Met Gly Ser
                 20

<210> SEQ ID NO 16
<211> LENGTH: 15
<212> TYPE: PRT
<213> ORGANISM: Artificial Sequence
<220> FEATURE:
<223> OTHER INFORMATION: Synthetic polypeptide including sequence
      derived from mouse laminin (AG32)

<400> SEQUENCE: 16

Lys Gly Gly Thr Trp Tyr Lys Ile Ala Phe Gln Arg Asn Arg Lys
1               5                  10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic polypeptide including sequence
      derived from mouse laminin (C68)

<400> SEQUENCE: 17

Lys Gly Gly Thr Ser Ile Lys Ile Arg Gly Thr Tyr Ser Glu Arg
1               5                  10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic polypeptide including sequence
      derived from mouse laminin (C28)

<400> SEQUENCE: 18

Lys Tyr Gly Thr Asp Ile Arg Val Thr Leu Asn Arg Leu Asn Thr Phe
1               5                  10                  15

<210> SEQ ID NO 19
```

```
<211> LENGTH: 16
<212> TYPE: PRT
<213> ORGANISM: Artificial Sequence
<220> FEATURE:
<223> OTHER INFORMATION: Synthetic polypeptide including sequence
      derived from mouse laminin (C64)

<400> SEQUENCE: 19

Lys Tyr Gly Ser Glu Thr Thr Val Lys Tyr Ile Phe Arg Leu His Glu
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic polypeptide including sequence
      derived from mouse laminin (A208)

<400> SEQUENCE: 20

Lys Tyr Gly Ala Ala Ser Ile Lys Val Ala Val Ser Ala Asp Arg
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic polypeptide including sequence
      derived from mouse laminin (C16)

<400> SEQUENCE: 21

Lys Tyr Gly Lys Ala Phe Asp Ile Thr Tyr Val Arg Leu Lys Phe
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic polypeptide (AG73 with KYG linker)

<400> SEQUENCE: 22

Lys Tyr Gly Arg Lys Arg Leu Gln Val Gln Leu Ser Ile Arg Thr
1               5                   10                  15

<210> SEQ ID NO 23
<211> LENGTH: 13
<212> TYPE: PRT
<213> ORGANISM: Artificial Sequence
<220> FEATURE:
<223> OTHER INFORMATION: Synthetic polypeptide (RNIA with linker)

<400> SEQUENCE: 23

Lys Gly Gly Arg Asn Ile Ala Glu Ile Ile Lys Asp Ile
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic polypeptide (AG-73)

<400> SEQUENCE: 24

Arg Lys Arg Leu Gln Val Gln Leu Ser Ile Arg Thr
1               5                   10
```

```
<210> SEQ ID NO 25
<211> LENGTH: 10
<212> TYPE: PRT
<213> ORGANISM: Artificial Sequence
<220> FEATURE:
<223> OTHER INFORMATION: Synthetic polypeptide (RNIA)

<400> SEQUENCE: 25

Arg Asn Ile Ala Glu Ile Ile Lys Asp Ile
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic polypeptide including sequence
      derived from mouse laminin (C16)

<400> SEQUENCE: 26

Lys Ala Phe Asp Ile Thr Tyr Val Arg Leu Lys Phe
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 27

Arg Gly Gly Ser Asp Pro Ile Tyr Lys
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic polypeptide containing RGD

<400> SEQUENCE: 28

Gly Arg Gly Asp Ser Pro Ile Ile Lys
1               5

<210> SEQ ID NO 29
<211> LENGTH: 15
<212> TYPE: PRT
<213> ORGANISM: Artificial Sequence
<220> FEATURE:
<223> OTHER INFORMATION: Synthetic polypeptide including sequence
      derived from human vitronectin

<400> SEQUENCE: 29

Lys Gly Gly Pro Gln Val Thr Arg Gly Asp Val Phe Thr Met Pro
1               5                   10                  15

<210> SEQ ID NO 30
<211> LENGTH: 9
<212> TYPE: PRT
<213> ORGANISM: Artificial Sequence
<220> FEATURE:
<223> OTHER INFORMATION: Synthetic polypeptide containing RGE

<400> SEQUENCE: 30

Gly Arg Gly Glu Ser Pro Ile Tyr Lys
1               5
```

```
<210> SEQ ID NO 31
<211> LENGTH: 14
<212> TYPE: PRT
<213> ORGANISM: Artificial Sequence
<220> FEATURE:
<223> OTHER INFORMATION: Synthetic polypeptide including sequence
      derived from mouse bonesialo protein

<400> SEQUENCE: 31

Lys Gly Gly Asn Gly Glu Pro Arg Gly Asp Thr Arg Ala Tyr
1               5                   10
```

What is claimed is:

1. A cell culture article, comprising:
a substrate having a surface;
a swellable (meth)acrylate layer disposed on the surface of the substrate, wherein the swellable (meth)acrylate layer is formed from a composition comprising a carboxyl group-containing (meth)acrylate monomer, a cross-linking (meth)acrylate monomer, and a hydrophilic monomer capable of polymerizing with the carboxyl gtow-containing (meth)acrylate monomer and the cross-linking (meth)acrylate monomer, and
a peptide conjugated to a carboxyl group of the carboxyl group-containing monomer of the swellable (meth) acrylate layer,
wherein the peptide comprises an amino acid sequence selected from the group consisting of:
LysGlyGlyAsnGlyGluProArgGlyAspThrTyrArgAlaTyr (SEQ ID NO:4);
AsnGlyGluProArgGlyAspThrTyaArgAlaTyr (SEQ ID NO:5)
LysGlyGlyLys$^4$AsnGlyGluProArgGlyAspThrTyrArgAlaTyrAsp$^{17}$ (SEQ ID NO:6), where Lys$^4$ and Asp$^{17}$ together form an amide bond to cyclize a portion of the polypeptide;
LysGlyGlyLys$^4$GluProArgGlyAspThrTryArgAsp$^{13}$ (SEQ ID NO:7), where Lys$^4$ and Asp$^{13}$ together form an amide bond to cyclize a portion of the polypeptide;
LysGlyGlyCys$^4$AsnGlyGluProArgGlyAspThrTyrArgAlaTyrCys$^{17}$ (SEQ ID NO:8), where Cys$^4$ and Cys$^{17}$ together form a disulfide bond to cyclize a portion of the polypeptide;
LysGlyGlyCys$^4$GluProArgGlyAspThrTryArgCys$^{13}$ (SEQ ID NO:9), where Cys$^4$ and Cys$^{13}$ together form a disulfide bond to cyclize a portion of the polypeptide;
GlyArgGlyAspSerProLys (SEQ ID NO:11); and
LysGlyGlyAlaValThrGlyArgGlyAspSerProAlaSerSer (SEQ ID NO:12).

2. The cell culture article of claim 1, wherein the swellable (meth)acrylate layer has an equilibrium water content (EWC) calculated from the formula:

EWC (%)=[(Wgel−Wdry)/(Wgel)]* 100, in water, of between about 5% and about 50%.

3. The cell culture article of claim 1, wherein the swellable (meth)acrylate layer has an equilibrium water content in water of between about 10% and about 40%.

4. The cell culture article of claim 1, wherein the carboxyl group-containing (meth)acrylate monomer is 2-carboxyethylacrylate.

5. The cell culture article of claim 1, wherein the cross-linking (meth)acrylate monomer is tetra(ethylene glycol) dimethacrylate or tetra(ethylene glycol) diacrylate.

6. The cell culture article of claim 1, wherein the hydrophilic monomer is selected from the group consisting of hydroxyethyl methacrylate, hydroxypropyl methacrylate, 2-hydroxyethyl acrylate, di(ethylene glycol) ethyl ether methacrylate, ethylene glycol methyl ether methacrylate.

7. The cell culture article of claim 1, wherein the ratio, by volume, of the cross-linking (meth)acrylate monomer to the carboxy group-containing meth(acrylate) monomer to the hydrophilic monomer is about 1-10 to about 10-40 to about 60-90.

8. The cell culture article of claim 1, wherein the ratio by volume, of the cross-linking (meth)acrylate monomer to the carboxy group-containing meth(acrylate) monomer to the hydrophilic monomer is about 3 to 20 to 80.

9. The article of claim 1, wherein the swellable (meth) acrylate layer is free of polypeptide crosslinkers.

10. The article of claim 1, wherein the swellable (meth) acrylate layer has a uniform thickness and wherein the swellable (methacrylate) layer is less than about 2 micrometers in thickness.

* * * * *

UNITED STATES PATENT AND TRADEMARK OFFICE
CERTIFICATE OF CORRECTION

PATENT NO. : 8,354,274 B2  
APPLICATION NO. : 12/362924  
DATED : January 15, 2013  
INVENTOR(S) : Andrei Gennadyevich Fadeev et al.

Page 1 of 1

It is certified that error appears in the above-identified patent and that said Letters Patent is hereby corrected as shown below:

|  | Col. | Line | *In the Claims* |
|---|---|---|---|
| Claim 1 | 59 | 23 | Reads – gtow-containing meth(acrylate) monomer;<br>Should read – group-containing meth(acrylate) monomer. |

Signed and Sealed this  
Fourth Day of June, 2013

Teresa Stanek Rea  
*Acting Director of the United States Patent and Trademark Office*